US012606562B2

(12) United States Patent
Bruno et al.

(10) Patent No.: US 12,606,562 B2
(45) Date of Patent: Apr. 21, 2026

(54) PYRIDOPYRIMIDINES DERIVATIVES AS P2X3 INHIBITORS

(71) Applicant: CHIESI FARMACEUTICI S.p.A., Parma (IT)

(72) Inventors: Paolo Bruno, Parma (IT); Matteo Biagetti, Parma (IT); Claudio Fiorelli, Parma (IT); Charles Baker-Glenn, Parma (IT); Hervè Van De Poel, Parma (IT); Stephen David Penrose, Parma (IT); Roberta Lanaro, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 902 days.

(21) Appl. No.: 17/615,012

(22) PCT Filed: May 28, 2020

(86) PCT No.: PCT/EP2020/064915
§ 371 (c)(1),
(2) Date: Nov. 29, 2021

(87) PCT Pub. No.: WO2020/239953
PCT Pub. Date: Dec. 3, 2020

(65) Prior Publication Data

US 2022/0235060 A1 Jul. 28, 2022
US 2023/0212169 A9 Jul. 6, 2023

(30) Foreign Application Priority Data

May 31, 2019 (EP) .................................... 19177610
Oct. 2, 2019 (EP) .................................... 19201165

(51) Int. Cl.
*C07D 487/04* (2006.01)
*C07D 471/04* (2006.01)

(52) U.S. Cl.
CPC ......... *C07D 487/04* (2013.01); *C07D 471/04* (2013.01)

(58) Field of Classification Search
CPC ... C07D 487/04; C07D 471/04; C07D 475/06
See application file for complete search history.

(56) References Cited

U.S. PATENT DOCUMENTS

| | | | |
|---|---|---|---|
| 5,707,998 A | 1/1998 | Takase et al. | |
| 2011/0319414 A1 | 12/2011 | Kai et al. | |
| 2012/0122838 A1 | 5/2012 | Ren et al. | |
| 2018/0311240 A1 | 11/2018 | Broka et al. | |
| 2021/0300922 A1* | 9/2021 | Hernández Herrero | C07D 471/04 |
| 2023/0092892 A1* | 3/2023 | Bruno | C07F 5/02 514/210.21 |

FOREIGN PATENT DOCUMENTS

| | | | |
|---|---|---|---|
| CN | 106565684 | A | 4/2017 |
| CN | 109721554 | A | 5/2019 |
| JP | 4342007 | B2 | 10/2009 |
| JP | 2009537588 | A | 10/2009 |
| RU | 2422441 | C2 | 6/2011 |
| RU | 2551845 | C2 | 5/2015 |
| WO | WO-2005095359 | A1 | 10/2005 |
| WO | WO-2007134986 | A1 | 11/2007 |
| WO | WO-2008000645 | A1 | 1/2008 |
| WO | WO-2008077651 | A1 | 7/2008 |
| WO | WO-2008123963 | A1 | 10/2008 |
| WO | WO-2008130481 | A1 | 10/2008 |
| WO | WO-2009110985 | A2 | 9/2009 |
| WO | WO-2010033168 | A2 | 3/2010 |
| WO | WO-2010038060 | A1 | 4/2010 |
| WO | WO-2011041655 | A1 | 4/2011 |
| WO | WO-2014102233 | A1 | 7/2014 |
| WO | WO-2016053794 | A1 | 4/2016 |
| WO | WO-2016084922 | A1 | 6/2016 |
| WO | WO-2016088838 | A1 | 6/2016 |
| WO | WO-2016091776 | A1 | 6/2016 |
| WO | WO-2017011729 | A1 | 1/2017 |
| WO | WO-2017058645 | A1 | 4/2017 |
| WO | WO-2017091661 | A1 | 6/2017 |
| WO | WO-2018005435 | A1 | 1/2018 |
| WO | WO-2018134685 | A2 | 7/2018 |

(Continued)

OTHER PUBLICATIONS

PubChem CID 617686, National Center for Biotechnology Information. PubChem Compound Summary for CID 617686, 6-Bromoquinazoline-2,4(1H,3H)-dione. https://pubchem.ncbi.nlm.nih.gov/compound/6-Bromoquinazoline-2_4_1H_3H_-dione. Accessed Aug. 30, 2024, create date Mar. 27, 2005. (Year: 2005).*
Chemical Abstracts Registry No. 303120-19-6, indexed in the Registry file on STN CAS Online on Nov. 17, 2000. (Year: 2000).*
Chemical Abstracts Registry No. 448204-55-5 {indexed in the Registry file on STN CAS Online on Sep. 9, 2002. (Year: 2002).*
Leal et al., International Journal of Molecular Sciences (Mar. 6, 2015), 16(3), 5235-5253. (Year: 2015).*
A machine generated English translation of CN 106565684 A, Wan et al., 2017. (Year: 2017).*

(Continued)

*Primary Examiner* — Laura L Stockton
(74) *Attorney, Agent, or Firm* — STERNE, KESSLER, GOLDSTEIN & FOX P.L.L.C.

(57) ABSTRACT

The present invention relates to compounds of formula I inhibiting P2X purinoceptor 3 (hereinafter $P2X_3$ inhibitors); particularly the invention relates to compounds that are pyridopyrimidines derivatives, methods of preparing such compounds, pharmaceutical compositions containing them and therapeutic use thereof. The compounds of the invention may be useful in the treatment of many disorders associated with $P2X_3$ receptors mechanisms, such as respiratory diseases including cough, asthma, idiopathic pulmonary fibrosis (IPF) and chronic obstructive pulmonary disease (COPD).

14 Claims, No Drawings

(56) References Cited

FOREIGN PATENT DOCUMENTS

| | | | |
|---|---|---|---|
| WO | WO-2018204775 | A1 | 11/2018 |
| WO | WO-2020020939 | A1 | 1/2020 |
| WO | WO-2020239951 | A1 | 12/2020 |
| WO | WO-2020239952 | A1 | 12/2020 |
| WO | WO-2020239953 | A1 | 12/2020 |

OTHER PUBLICATIONS

Chemical Abstracts Registry No. 2062041-82-9, indexed in the Registry file on STN CAS Online on Jan. 31, 2017. (Year: 2017).*
Chemical Abstracts Registry No. 2061172-14-1, indexed in the Registry file on STN CAS Online on Jan. 29, 2017. (Year: 2017).*
Chemical Abstracts Registry No. 2060589-75-3, indexed in the Registry file on STN CAS Online on Jan. 27, 2017. (Year: 2017).*
Iwaki, T., et al., "Discovery and in vivo effects of novel human natriuretic peptide receptor A (NPR-A) agonists with improved activity for rat NPR-A," Bioorg Med Chem 25(24):6680-6694, Elsevier Ltd., United Kingdom (Dec. 2017).
Hou, J., et al., "Design, synthesis, anti-tumor activity, and molecular modeling of quinazoline and pyridol[2,3-d]pyrimidine derivatives targeting epidermal growth factor receptor," Eur J Med Chem 118:276-89, Elsevier, Netherlands (Aug. 2016).
Mott, B., et al., "Evaluation of substituted 6-arylquinazolin-4-amines as potent and selective inhibitors of cdc2-like kinases (Clk)," Bioorg Med Chem Lett. 19(23):6700-6705, Elsevier, Netherlands (Dec. 2009).
Rosenthal, A.S., et al., "Potent and selective small molecule inhibitors of specific isoforms of Cdc2-like kinases (Clk) and dual specificity tyrosine-phosphorylation-regulated kinases (Dyrk)," Bioorg Med Chem Lett 21(10):3152-58, Elsevier, Netherlands (May 2011).
Scarborough, H.C., et al., "Pyrrolidines. VI. Synthesis of 4-(1-Substituted 3-Pyrrolidinylmethylamino)- and 4-(1-Substituted 3-Pyrrolidinylmethoxy)quinazolines," J Org Chem 27(3):957-961, American Chemical Society, United States (Mar. 1962).
Abdulqawi, R., et al., "P2X3 receptor antagonist (AF-219) in refractory chronic cough: a randomised, double-blind, placebo-controlled phase 2 study," Lancet 385(9974):1198-205, Elsevier Ltd., United Kingdom (2015).
Basoglu, O. K., et al., "Effects of aerosolized adenosine 5'-triphosphate vs adenosine 5'-monophosphate on dyspnea and airway caliber in healthy nonsmokers and patients with asthma," Chest 128(4):1905-1909, Elsevier, Netherlands (2005).
Bo, X., et al., "Localization of ATP-gated P2X2 and P2X3 receptor immunoreactive nerves in rat taste buds," NeuroReport 10(5):1107-11, Lippincott Williams and Wilkins Ltd., United States (1999).
Canda, A. E., et al., "Physiology and pharmacology of the human ureter: basis for current and future treatments," Urol Int 78(4):289-298, S. Karger AG, Switzerland (2007).
Cheung, K.-K., and Burnstock, G., "Localization of P2X3 receptors and coexpression with P2X2 receptors during rat embryonic neurogenesis," J Comp Neurol 443(4):368-386, Wiley-Liss, United States (2002).
Finlay, H. J., et al., "Discovery of 5-Phenyl-N-(pyridin-2-ylmethyl)-2-(pyrimidin-5-y1)quinazolin-4-amine as a Potent I Kur Inhibitor," ACS Med Chem Lett 7(9):831-834, American Chemical Society, United States (2016).
Ford, A. P., "In pursuit of P2X3 antagonists: novel therapeutics for chronic pain and afferent sensitization," Purinergic Signal 8(Suppl 1):3-26, Springer, Netherlands (2012).
Ford, A. P., and Undem, B. J., "The therapeutic promise of ATP antagonism at P2X3 receptors in respiratory and urological disorders," Front Cell Neurosci 7:267, 10 pages, Frontiers Media S.A., Switzerland (2013).
Garcia-Guzman, M., et al., "Molecular characterization and pharmacological properties of the human P2X3 purinoceptor," Brain Res Mol Brain Res 47(1-2):59-66, Elsevier, Netherlands (1997).
Guo, J., et al., "Contributions of purinergic P2X3 receptors within the midbrain periaqueductal gray to diabetes-induced neuropathic pain," J Physiol Sci 65(1):99-104, BioMed Central Ltd., United Kingdom (2015).
Haffner, C. D., et al., "Discovery, Synthesis, and Biological Evaluation of Thiazoloquin(az)olin(on)es as Potent CD38 Inhibitors," J Med Chem 58(8):3548-3571, American Chemical Society, United States (2015).
Huang, H.-C., et al., "A novel one-pot conversion of methyl sulfones to sulfonamides," Tetrahedron Letters 35(39):7201-7204, Elsevier, Netherlands (1994).
Kaczmarek-Hajek, K., et al., "Molecular and functional properties of P2X receptors—recent progress and persisting challenges," Purinergic Signal 8(3):375-417, Springer, Netherlands (2012).
Kamei, J., and Takahashi, Y., "Involvement of ionotropic purinergic receptors in the histamine-induced enhancement of the cough reflex sensitivity in guinea pigs," Eur J Pharmacol 547(1-3):160-164, Elsevier, Netherlands (2006).
Li, C.-L., et al., "Effects of intracavernous injection of P2X3 and NK1 receptor antagonists on erectile dysfunction induced by spinal cord transection in rats," Andrologia 47(1):25-29, Wiley-Blackwell Publishing Ltd., United Kingdom (2015).
Lloyd, R. F., et al., "4-(Substituted)pteridines, analogues of kinetin," Canadian Journal of Chemistry 45(19):2213-2216, 4 pages, NRC Research Press, Canada (1967).
Maynard, J. P., et al., "P2X3 purinergic receptor overexpression is associated with poor recurrence-free survival in hepatocellular carcinoma patients," Oncotarget 6(38):41162-41179, Impact Journals LLC, United States (2015).
North, R. A., "Molecular physiology of P2X receptors," Physiol Rev 82(4):1013-1067, The American Physiological Society, United States (2002).
North, R. A., and Jarvis, M. F., "P2X receptors as drug targets," Mol Pharmacol 83(4):759-69, American Society for Pharmacology and Experimental Therapeutics, United States (2013).
Pan, Y., et al., "Pharmacophore and 3D-QSAR characterization of 6-arylquinazolin-4-amines as Cdc2-like kinase 4 (Clk4) and dual specificity tyrosine-phosphorylation-regulated kinase 1A (Dyrk1A) inhibitors ," J Chem Inf Model 53(4):938-947, American Chemical Society, United States (2013).
Registry Nov. 16, 1984 (Nov. 16, 1984), Database accession No. RN 74173-76-5, RN 26850-60-2, RN 20028-68-6 Retrieved from the Internet: URL:Chemical Abstracts Service, Columbus, Ohio, US XP002796884.
Registry May 26, 1986 (May 26, 1986), Database accession No. RN 102393-82-8 Retrieved from the Internet: URL:Chemical Abstracts Service, Columbus, Ohio, US XP002796887.
Registry Dec. 17, 2007 (Dec. 17, 2007), Database accession No. RN 958360-30-0 Retrieved from the Internet: URL:Chemical Abstracts Service, Columbus, Ohio, US XP002796883.
Registry Jul. 28, 2008 (Jul. 28, 2008), Database accession No. RN 1036738-12-1 Retrieved from the Internet: URL:Chemical Abstracts Service, Columbus, Ohio, US XP002796882.
Registry Apr. 27, 2010 (Apr. 27, 2010), Database accession No. RN 1220518-09-1 Retrieved from the Internet: URL:Chemical Abstracts Service, Columbus, Ohio, US XP002796881.
Registry Aug. 3, 2010 (Aug. 3, 2010), Database accession No. RN 1234616-70-6 Retrieved from the Internet: URL:Chemical Abstracts Service, Columbus, Ohio, US XP002796880.
Registry Jan. 27, 2011 (Jan. 27, 2011), Database accession No. RN 1260665-43-7 Retrieved from the Internet: URL:Chemical Abstracts Service, Columbus, Ohio, US XP002796879.
Registry Nov. 17, 2017 (Nov. 17, 2017), Database accession No. RN 2143878-49-1 Retrieved from the Internet: URL:Chemical Abstracts Service, Columbus, Ohio, US XP002796469.
Registry Jun. 28, 1991 (Jun. 28, 1991), Database accession No. RN 2379641-82-2 Retrieved from the Internet: URL:Chemical Abstracts Service, Columbus, Ohio, US XP002796886.
Registry Oct. 21, 2014 (Oct. 21, 2014), Database accession No. RN 2387320-34-3 Retrieved from the Internet: URL:Chemical Abstracts Service, Columbus, Ohio, US XP002796885.

(56) References Cited

OTHER PUBLICATIONS

Spulák, M., et al., "Novel bronchodilatory quinazolines and quinoxalines: synthesis and biological evaluation," Eur J Med Chem 74:65-72, Elsevier, Netherlands (2014).
Szántó, G., et al., "New P2X3 receptor antagonists. Part 2: Identification and SAR of quinazolinones," Bioorg Med Chem Lett 26(16):3905-3912, Elsevier, Netherlands (2016).
Teixeira, J. M., et al., "P2X3 and P2X2/3 Receptors Play a Crucial Role in Articular Hyperalgesia Development Through Inflammatory Mechanisms in the Knee Joint Experimental Synovitis," Mol Neurobiol 54(8):6174-6186, Springer Science+Business Media, Germany (2017).
Undem, B. J., and Nassenstein, C., "Airway nerves and dyspnea associated with inflammatory airway disease," Respir Physiol Neurobiol 167(1):36-44, Elsevier, Netherlands (2009).
Vandenbeuch, A., et al., "Role of the ectonucleotidase NTPDase2 in taste bud function," Proc Natl Acad Sci USA 110(36):14789-94, National Academy of Sciences, United States (2013).
Zhang, Q., et al., "Design, synthesis and biological evaluation of novel histone deacetylase inhibitors incorporating 4-aminoquinazolinyl systems as capping groups," Bioorg Med Chem Lett 27(21):4885-4888, Elsevier, Netherlands (2017).
International Search Report and Written Opinion for International Application No. PCT/EP2020/064915, European Patent Office, Netherlands, mailed on Jun. 23, 2020, 13 pages.
Co-pending Application, U.S. Appl. No. 17/615,056, inventors Bruno, P., et al., international filing date: May 28, 2020 (Not yet Published).
Co-pending Application, U.S. Appl. No. 17/615,017, inventors Bruno, P., et al., international filing date: May 28, 2020 (Not yet Published).
Registry May 7, 2015 (May 7, 2015), Database accession No. RN 1700636-78-7 Retrieved from the Internet: URL:Chemical Abstracts Service, Columbus, Ohio, US XP002796590.
Registry Jul. 24, 2014 (Jul. 24, 2014), Database accession No. RN 1616828-53-5 Retrieved from the Internet: URL:Chemical Abstracts Service, Columbus, Ohio, US XP002796899.
Registry May 11, 2014 (May 11, 2014), Database accession No. RN 1602300-56-0 Retrieved from the Internet: URL:Chemical Abstracts Service, Columbus, Ohio, US XP002796900.
Registry Mar. 12, 2014 (Mar. 12, 2014), Database accession No. RN 1566729-83-6 Retrieved from the Internet: URL:Chemical Abstracts Service, Columbus, Ohio, US XP002796901.
Registry Mar. 11, 2014 (Mar. 11, 2014), Database accession No. RN 1566199-66-3 Retrieved from the Internet: URL:Chemical Abstracts Service, Columbus, Ohio, US XP002796902.
Registry Jan. 24, 1987 (Jan. 24, 1987), Database accession No. RN 106319-77-1, RN 106319-93-1 Retrieved from the Internet: URL:Chemical Abstracts Service, Columbus, Ohio, US XP002796903.
Registry Mar. 22, 1986 (Mar. 22, 1986), Database accession No. RN 100949-33-5, RN 100948-96-7 Retrieved from the Internet: URL:Chemical Abstracts Service, Columbus, Ohio, US XP002796904.
Registry Nov. 16, 1984 (Nov. 16, 1984), Database accession No. RN 19815-13-5 Retrieved from the Internet: URL:Chemical Abstracts Service, Columbus, Ohio, US XP002796905.

* cited by examiner

PYRIDOPYRIMIDINES DERIVATIVES AS P2X3 INHIBITORS

FIELD OF THE INVENTION

The present invention relates to compounds inhibiting P2X purinoceptor 3 (hereinafter $P2X_3$ inhibitors); particularly the invention relates to compounds that are pyridopyrimidines derivatives, methods of preparing such compounds, pharmaceutical compositions containing them and therapeutic use thereof.

The compounds of the invention may be useful in the treatment of many disorders associated with $P2X_3$ receptors mechanisms, such as respiratory diseases including cough, asthma, idiopathic pulmonary fibrosis (IPF) and chronic obstructive pulmonary disease (COPD).

BACKGROUND OF THE INVENTION

P2X receptors are cell surface ion channels activated by extracellular Adenosine 5-TriPhosphate (ATP). P2X receptor family are trimeric assemblies composed of seven distinct subunit subtypes ($P2X_1$-7) that assemble as homomeric and heteromeric channels. All subunits share a common topology containing intracellular termini, two transmembrane helices forming the ion channels and a large extracellular domain containing the ATP binding site. Homomeric $P2X_1$, $P2X_2$, $P2X_3$, $P2X_4$, $P2X_5$, and $P2X_7$ channels and heteromeric $P2X_{2/3}$ and $P2X_{1/5}$ channels have been fully characterized following heterologous expression. P2X receptors are abundantly distributed, and functional responses are seen in neurons, glia, epithelia, endothelia, bone, muscle, and hemopoietic tissues. On smooth muscles, P2X receptors respond to ATP released from sympathetic motor nerves (e.g., in ejaculation). On sensory nerves, they are involved in the initiation of afferent signals in several viscera (e.g., bladder, intestine) and play a key role in sensing tissue-damaging and inflammatory stimuli. Paracrine roles for ATP signaling through P2X receptors are likely in neurohypophysis, ducted glands, airway epithelia, kidney, bone and hemopoietic tissues. (RA. North: Molecular Physiology of P2X Receptors; Physiol Rev, Vol 82, October 2002). All P2X receptors are non-selective cation channels permeable to Na+ and Ca+ ions and are activated by ATP; however, the pharmacology of the receptor subtypes varies with respect to sensitivity to ATP and to small molecules antagonists. (K Kaczmarek-Hajek et al: Molecular and functional properties of P2X receptors—recent progress and persisting challenges; Purinergic Signalling 8:375-417, 2012)

In humans, the $P2X_3$ receptor has been reported in heart and spinal cord at the mRNA level and in DRG, intestine (myenteric plexus neurons), urinary bladder (urothelium and suburothelium), and dental pulp at the protein level (Garcia-Guzman M et al: Molecular characterization and pharmacological properties of the human $P2X_3$ purinoceptor: Brain Res Mol Brain Res. 1997; 47(1-2):59-66).

The neurophysiological role of $P2X_3$ receptors in sensory nerve function in the airways is similar to that mediating somatic nociception (Undem B J and Nassenstein C: Airway nerves and dyspnea associated with inflammatory airway disease, Respir Physiol Nerobiol 167: 36-44, 2009). This similarity has driven hypotheses concerning the involvement of $P2X_3$ receptors in the symptoms of airway dysfunction including cough and bronchial hyper-reactivity (Ford A P: In pursuit of $P2X_3$ antagonists: novel therapeutics for chronic pain and and afferent sensitization, Purinergic signal 8 (suppl 1):3-26, 2012; North R A, Jarvis M F P2X Receptors as Drug Targets; Mol Pharmacol, 83:759-769, 2013). $P2X_3$ subunits are also co-localized in many neurons, particularly within DRG, nodose ganglia, nucleus tractus solitarius, and taste buds (Cheung K K, Burnstock G: Localization of $P2X_3$ receptors and coexpression with $P2X_2$ receptors during rat embryonic neurogenesis. J Comp Neurol 443(4):368-382 2002)

$P2X_3$ antagonists have been proposed for the treatment of diabetic neuropathic pain (Guo J et al: Contributions of purinergic $P2X_3$ receptors within the midbrain periaqueductal gray to diabetes-induced neuropathic pain, J Physiol Sci January; 65(1):99-104 2015).

$P2X_3$ and $P2X_{2/3}$ channels play an important role in the development of articular hyperalgesia of arthritic joints (Teixeira J M et al: $P2X_3$ and $P2X_{2/3}$ Receptors Play a Crucial Role in Articular Hyperalgesia Development Through Inflammatory Mechanisms in the Knee Joint Experimental Synovitis, Mol Neurobiol October; 54(8): 6174-6186, 2017).

$P2X_3$ are also a potential target for therapeutic treatment of bladder pain. They were also proposed to be analgesic targets to treat ureteral colicky pain and to facilitate ureteral stone passage (Canda A E et al: Physiology and pharmacology of the human ureter: basis for current and future treatments, Urol Int. 78(4):289-98, 2007).

$P2X_3$ over-expression is involved in poor recurrence-free survival in hepatocellular carcinoma patients and identifies the $P2X_3$ as a potential therapeutic target (Maynard J P et al: $P2X_3$ purinergic receptor overexpression is associated with poor recurrence-free survival in hepatocellular carcinoma patients Oncotarget December 1; 6(38):41162-79, 2015).

It has been suggested that $P2X_3$ antagonists may improve recovery of erectile function (Li C L et al: Effects of intracavernous injection of $P2X_3$ and NK1 receptor antagonists on erectile dysfunction induced by spinal cord transection in rats, Andrologia February; 47(1):25-9, 2015).

ATP enhances citric acid-evoked and histamine-evoked cough in preclinical models, effects that can be attenuated by $P2X_3$ selective antagonists (Kamei J and Takahashi Y: Involvement of ionotropic purinergic receptors in the histamine-induced enhancement of the cough reflex sensitivity in guinea pigs, October 10; 547(1-3):160-4, 2006).

In humans, local delivery of ATP initiates cough and bronchospasm (Basoglu O K et al: Effects of aerosolized adenosine 5'-triphosphate vs adenosine 5'-monophosphate on dyspnea and airway caliber in healthy nonsmokers and patients with asthma, Chest. October; 128(4):1905-9, 2005).

The therapeutic promise of $P2X_3$ antagonists for the treatment of chronic cough was first recognized by Ford and Undem (Ford A P, Undem B J: The therapeutic promise of ATP antagonism at $P2X_3$ receptors in respiratory and urological disorders, Front Cell Neurosci, December 19; 7:267, 2013). $P2X_3$ are expressed by airway afferent nerves and mediate hypersensitivity of the cough reflex, which is dramatically reduced by the oral $P2X_3$ antagonist, AF-219 (Abdulgawi et al: $P2X_3$ receptor antagonist (AF-219) in refractory chronic cough: a randomised, double-blind, placebo-controlled phase 2 study, Lancet 385, 1198-205, 2015).

ATP is a key neurotransmitter in the taste system, acting largely via $P2X_{2/3}$ heteromultimer receptors. Consequently, disruption of taste function may be an unintentional consequence of therapeutic trials of pain, chronic cough and other conditions using purinergic $P2X_3$ antagonists (Vandenbeuch A et al: Role of the ectonucleotidase NTPDase2 in taste bud function, Proc Natl Acad Sci USA, September 3; 110(36): 14789-94, 2013. Bo X et al: Localization of ATP-gated $P2X_2$ and $P2X_3$ receptor immunoreactive nerves in rat taste buds, Neuroreport, 10(5):1107-11, 1999).

Various compounds have been described in the literature as $P2X_3$ and/or $P2X_{2/3}$ Inhibitors.

WO2017058645 (Afferent Pharmaceuticals INC) discloses the use of diaminopyrimidine $P2X_3/P2X_{2/3}$ antagonists for the treatment of disorders including cough, chronic cough and urge to cough, including cough associated with a respiratory disease or disorder, administering an efficacious amount of the compound disclosed. However, pyridopyrimidines derivatives are not disclosed.

WO2017011729 (Patara Pharma LLC), discloses the use of cromolyn or a pharmaceutically acceptable salt thereof and $P2X_3$ and/or a $P2X_{2/3}$ receptor antagonist as antitussive agent, for the treatment of lung diseases and conditions.

WO2016091776, (Evotec AG), discloses 1,3-thiazol-2-yl substituted benzamide compounds that inhibit $P2X_3$ receptor and to pharmaceutical compositions containing such compounds, and the use of compounds for the treatment os several disorders, including the respiratory diseases.

WO2016088838 (Shionogi), discloses purine derivatives compounds having a novel $P2X_3$ and/or $P2X_{2/3}$ receptor antagonizing effect.

WO2016084922, (Shionogi), discloses triazine derivatives compounds having a novel $P2X_3$ and/or $P2X_{2/3}$ receptor antagonizing effect WO2008123963 (Renovis) relates to fused heterocyclic compounds of the class tetrahydropyrido [4,3-d]pyrimidines and pharmaceutical compositions comprising such compounds. Also provided are methods for preventing and/or treating several disorders, such as neurodegenerative disorders, pain, asthma, autoimmune disorders administering the disclosed comoounds.

WO2008130481 (Renovis) discloses 2-cyanophenyl fused heterocyclic compounds of the class tetrahydropyrido [4,3-d]pyrimidines and pharmaceutical compositions comprising such compounds.

WO2010033168 (Renovis) discloses a series of benzamides substituted with phenyl or pyridyl which are stated to be useful for treatment of diseases associated with P2X purinergic receptors, and more particularly to $P2X_3$ receptor and/or $P2X_{2/3}$ receptor antagonists. However, pyridopyrimidines derivatives are not disclosed.

WO2009110985 (Renovis) relates to phenyl- and pyridyl-substituted benzamide compounds and pharmaceutical compositions comprising such compounds, but not thiazole-substituted benzamides, rendering said compounds different from the compounds of the present invention.

WO2008000645 (Roche) discloses tetrazole substituted arylamides compounds antagonists of $P2X_3$ and/or $P2X_{2/3}$ receptors, useful for the treatment of genitourinary, pain, gastrointestinal and respiratory diseases, conditions and disorders.

There remains a potential for developing novel and pharmacologically improved $P2X_3$ and/or $P2X_{2/3}$ inhibitors in many therapeutic areas such as in particular the respiratory diseases.

Despite the above cited prior art, there is still the need of novel pyridopyrimidines compounds for treatment of diseases associated with $P2X_3$ receptors in many therapeutic areas such as in particular the respiratory diseases, preferably having a selective action on the $P2X_3$ receptor.

Of note, the state of the art does not describe or suggest pyridopyrimidines derivatives compounds of general formula (I) of the present invention which represent a solution to the aforementioned need.

SUMMARY OF THE INVENTION

The present invention refers to compounds of formula (I)

(I)

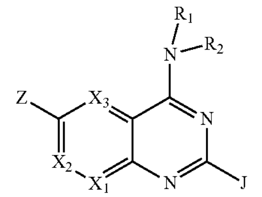

wherein $X_1$, $X_2$ and $X_3$ are independently CH or N,

Z is H or selected from the group consisting of $(C_1-C_4)$alkyl-, heteroaryl, aryl, wherein any of such heteroaryl and aryl may be optionally substituted by one or more groups selected from $(C_1-C_3)$alkyl, halo, CN, $(R^AR^B)NC(O)$—;

$R_1$ is H;

$R_2$ is selected from the group consisting of heteroaryl $(C_1-C_4)$alkyl-, $(C_3-C_8)$heterocycloalkyl-$(C_1-C_6)$alkyl-, wherein any of such alkyl, heteroaryl and heterocycloalkyl may be optionally substituted by one or more groups selected from $(C_1-C_3)$alkyl, halo, $R^AO(C_1-C_4)$alkylene-, $(C_1-C_6)$ haloalkyl, $R^AO$—;

$R^A$ and $R^B$ are at each occurrence independently H or $(C_1-C_4)$alkyl-, or $R^A$ and $R^B$ may form together with the nitrogen atom to which they are attached a 6-membered saturated heterocyclic monocyclic ring system optionally containing a further heteroatom which is nitrogen, which may be optionally substituted by $R^C(O)C$—; $R^C$ is $(C_1-C_6)$alkyl;

J is H or $(R^AR^B)N$—.

In a second aspect, the invention refers to a pharmaceutical composition comprising a compound of formula (I) or pharmaceutically acceptable salt thereof, either alone or in combination with another one or more active ingredient, in admixture with one or more pharmaceutically acceptable carrier or excipient.

In a third aspect, the invention provides a compound of formula (I) for the use as a medicament.

In a further aspect, the invention provides the use of a compound of formula (I) for use in treatment of any disease wherein the $P2X_3$ receptors are involved.

In a further aspect, the invention refers to a compound of formula (I) for use in the prevention and/or treatment of respiratory diseases including cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm.

In a further aspect, the invention refers to a compound of formula IIIa (IIIa)

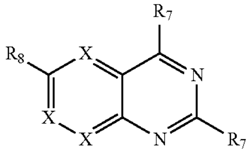

wherein X is N or CH, $R_7$ is OH and/or Cl;

$R_8$ is halo.

In a further aspect, the invention refers to the use of compound of formula (IIIa) as intermediate in the preparation of compounds of formula (I).

DETAILED DESCRIPTION OF THE INVENTION

The invention relates to a compound of formula (I)

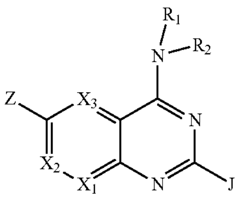

(I)

wherein $X_1$, $X_2$ and $X_3$ are independently CH or N,

Z is H or selected from the group consisting of ($C_1$-$C_4$) alkyl-, heteroaryl, aryl, wherein any of such heteroaryl and aryl may be optionally substituted by one or more groups selected from ($C_1$-$C_3$)alkyl, halo, CN, ($R^AR^B$)NC(O)—;

$R^1$ is H;

$R_2$ is selected from the group consisting of heteroaryl($C_1$-$C_4$)alkyl-, ($C_3$-$C_8$)heterocycloalkyl-($C_1$-$C_6$)alkyl-, wherein any of such alkyl, heteroaryl and heterocycloalkyl may be optionally substituted by one or more groups selected from ($C_1$-$C_3$)alkyl, halo, $R^AO$($C_1$-$C_4$) alkylene-, ($C_1$-$C_6$) haloalkyl, $R^AO$—;

$R^A$ and $R^B$ are at each occurrence independently H or ($C_1$-$C_4$)alkyl-, or $R^A$ and $R^B$ may form together with the nitrogen atom to which they are attached a 6-membered saturated heterocyclic monocyclic ring system optionally containing a further heteroatom which is nitrogen, which may be optionally substituted by $R^C$(O)C—;

$R^C$ is ($C_1$-$C_6$)alkyl;

J is H or selected from the group consisting of ($R^AR^B$)N—.

Definitions

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "halogen" or "halogen atoms" as used herein includes fluorine, chlorine, bromine, and iodine atom, preferably chlorine or fluorine.

The term "($C_x$-$C_y$) alkyl" wherein x and y are integers, refers to a straight or branched chain alkyl radical having from x to y carbon atoms. Thus, when x is 1 and y is 6, for example, the term includes methyl, ethyl, n-propyl, isopropyl, n-butyl, isobutyl, sec-butyl, t-butyl, n-pentyl and n-hexyl.

As used herein, the term "($C_x$-$C_y$)alkylene" wherein x and y are integers, refers to a $C_x$-$C_y$alkyl radical having in total two unsatisfied valencies, such as a divalent methylene radical.

The expressions "($C_x$-$C_y$) haloalkyl" wherein x and y are integers, refer to the above defined "$C_x$-$C_y$alkyl" groups wherein one or more hydrogen atoms are replaced by one or more halogen atoms, which can be the same or different.

Examples of said "($C_x$-$C_y$) haloalkyl" groups may thus include halogenated, poly-halogenated and fully halogenated alkyl groups wherein all of the hydrogen atoms are replaced by halogen atoms, e.g. trifluoromethyl or difluoro methyl, trifluoroethyl groups.

By way of analogy, the terms "($C_1$-$C_6$) hydroxyalkyl" or "($C_1$-$C_6$) aminoalkyl" refer to the above defined "($C_1$-$C_6$) alkyl" groups wherein one or more hydrogen atoms are replaced by one or more hydroxy (OH) or amino group respectively. Examples include respectively hydroxymethyl, aminomethyl, dimethylaminopropyl and the like.

In the present description, unless otherwise provided, the aminoalkyl encompasses alkyl groups (i.e. "($C_1$-$C_6$) alkyl" groups) substituted by one or more amino group (—$NR^AR^B$). Thus, an example of aminoalkyl is a mono-aminoalkyl group such as $R^AR^BN$—($C_1$-$C_6$) alkyl.

With reference to the substituent $R^A$ and $R^B$ as defined above and below, when $R^A$ and $R^B$ are taken together with the nitrogen atom they are linked to form 5 to 6 membered heterocyclic radical, at least one further ring carbon atom in the said heterocyclic radical is optionally replaced by at least one heteroatom (e.g. N, S or O) and/or may bear-oxo (═O) substituent groups. It is understood that the said heterocyclic radical might be further optionally substituted on any available position in the ring, namely on a carbon atom, or on any heteroatom available for substitution. Substitution on a carbon atom includes spiro disubstitution as well as substitution on two adjacent carbon atoms, in both cases thus form an additional 5 to 6 membered heterocyclic ring. Examples of said heterocycle radicals are 1-pyrrolidinyl, 1-piperidinyl, 1-piperazinyl, 4-methylpiperazinyl, piperazin-4yl-2-one, 4-morpholinyl, morpholinyl-3-one, 1-(piperazin-1-yl)ethenone.

The term "($C_x$-$C_y$) cycloalkyl" wherein x and y are integers, refers to saturated cyclic hydrocarbon groups containing the indicated number of ring carbon atoms. Examples include cyclopropyl, cyclobutyl, cyclopentyl, cyclohexyl, cycloheptyl.

The term "aryl" refers to mono cyclic carbon ring systems which have 6 ring atoms wherein the ring is aromatic. Examples of suitable aryl monocyclic ring systems include, for instance, phenyl.

The term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are fused through a common bond. Examples of suitable 5,6-membered heteroaryl are:

are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, tetrazolyl and triazinyl.

The term "heterocyclyl" or "heterocyclic" relate to a saturated mono-, bi- or tri-cyclic non-aromatic radical containing one or more heteroatoms selected from S, N and O. In the case of bicyclic heterocyclic systems, included within the scope of the term are fused, spiro and bridged bicyclic systems.

The term "($C_x$-$C_y$) heterocycloalkyl" wherein x and y are integers, refers to saturated or partially unsaturated monocyclic ($C_x$-$C_y$) cycloalkyl groups in which at least one ring carbon atom is replaced by at least one heteroatom (e.g. N, S or O) or may bear an -oxo (=O) substituent group. Said heterocycloalkyl (i.e. heterocyclic radical or group) may be further optionally substituted on the available positions in the ring, namely on a carbon atom, or on an heteroatom available for substitution. Substitution on a carbon atom includes spiro disubstitution as well as substitution on two adjacent carbon atoms, in both cases thus form additional condensed 5 to 6 membered heterocyclic ring. Examples of ($C_x$-$C_y$) heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydrothiophenyl, azetidinyl, oxetanyl, tetrahydropyranyl, pyranyl, 2H- or 4H-pyranyl, dihydro- or tetrahydrofuranyl, dihydroisoxazolyl, pyrrolidin-2-one-yl, dihydropyrrolyl radicals and the like.

Specific examples of said heterocycle radicals are tetrahydrothiophene 1,1-dioxide, 3,3-difluoropyrrolidinyl, 1-pyrrolidinyl, 1-methyl-2-pyrrolidinyl, 1-piperidinyl, 1-piperazinyl, 4-morpholinyl.

The expressions "Aryloxyl" and "Aryl ($C_1$-$C_6$) alkoxyl" likewise "heteroAryloxyl" and "Heteroaryl ($C_1$-$C_6$) alkoxyl" refer to Aryl or Heteroaryl groups attached through an oxygen bridge and chained Aryl-alkoxyl or HeteroAryl-alkoxyl groups. Examples of such groups are phenyloxy, benzyloxy and pyridinyloxy respectively.

The term "aryl ($C_1$-$C_6$) alkyl" refers to an aryl ring linked to a straight-chained or branched alkyl groups wherein the number of carbon atoms is from 1 to 6, e.g. phenylmethyl (i.e. benzyl), phenylethyl or phenylpropyl.

The term ($C_z$-$C_k$)heterocycloalkyl-($C_x$-$C_y$)alkyl wherein z and k are integers, refers to an heterocyclic ring linked to a straight-chained or branched alkyl groups having from x to y carbon atoms.

Likewise, the term "heteroaryl ($C_x$-$C_y$)alkyl" or "aryl ($C_x$-$C_y$)alkyl" refers to an heteroaryl or aryl ring linked to a straight-chained or branched alkyl groups having from x to y carbon atoms.

The expression "ring system" refers to mono- or bicyclic or polycyclic ring systems which may be saturated, partially unsaturated or unsaturated, such as aryl, ($C_3$-$C_{10}$) cycloalkyl, ($C_3$-$C_6$)heterocycloalkyl or heteroaryl.

The terms "group", "radical" or "fragment" or "substituent" are synonymous and are intended to indicate functional groups or fragments of molecules attachable to a bond or other fragments or molecules. Thus, as an example, a "heterocyclic radical" herein refers to a mono- or bi-cyclic saturated or partially saturated heterocyclic moiety (group, radical), preferably a 4 to 11 membered monocyclic radical, at least one further ring carbon atom in the said heterocyclic radical is optionally replaced by at least one further heteroatom independently selected from N, S or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring. Examples of said heterocycle radicals are 1-pyrrolidinyl, 1-piperidinyl, 1-piperazinyl, 4-morpholinyl and the like.

A dash ("-") that is not between two letters or symbols is meant to represent the point of attachment for a substituent. When graphically represented the point of attachment in a cyclic functional group is indicated with a dot ("·") localized in one of the available ring atoms where the functional group is attachable to a bond or other fragment of molecules.

An oxo moiety is represented by (O) as an alternative to the other common representation, e.g. (=O). Thus, in terms of general formula, the carbonyl group is herein represented as —C(O)—. In general, the bracketed group is a lateral group, not included into the chain, and brackets are used, when deemed useful, to help disambiguating linear chemical formulas; e.g. the sulfonyl group $—SO_2—$ might be also represented as $—S(O)_2—$ to disambiguate e.g. with respect to the sulfinic group —S(O)O—.

Whenever basic amino or quaternary ammonium groups are present in the compounds of formula I, physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups such as COOH groups, corresponding physiological cation salts may be present as well, for instance including alkaline or alkaline earth metal ions.

It will be apparent that compounds of formula (I) when contain one or more stereogenic center, may exist as optical stereoisomers.

Where the compounds according to the invention have at least one stereogenic center, they may accordingly exist as enantiomers. Where the compounds according to the invention possess two or more stereogenic centers, they may additionally exist as diastereoisomers. All such single enantiomers, diastereoisomers and mixtures thereof in any proportion are encompassed within the scope of the present invention. The absolute configuration (R) or (S) for carbon bearing a stereogenic center is assigned on the basis of Cahn-Ingold-Prelog nomenclature rules based on groups' priorities.

The invention further concerns the corresponding deuterated derivatives of compounds of formula (I).

All preferred groups or embodiments described above and herebelow for compounds of formula I may be combined among each other and apply as well mutatis mutandis.

In a preferred embodiment, the invention is directed to compounds of formula (I) as defined above, wherein $X_1$, $X_2$ and $X_3$ are independently CH or N, Z is selected from the group consisting of heteroaryl, preferably pyridinyl, thiazolyl and thienyl, and aryl, preferably phenyl, wherein any of such heteroaryl and aryl may be optionally substituted by one or more groups selected from ($C_1$-$C_3$)alkyl and halo, preferably from methyl, fluorine and chlorine;

$R^1$ is H;

$R_2$ is a heteroaryl($C_1$-$C_4$)alkyl-, preferably (pyridazyl) methyl, (pyridazyl)ethyl (pyridinyl)methyl, (pyrimidinyl)ethyl, (oxadiazolyl)ethyl, wherein any of such heteroaryl may be optionally substituted by one or more groups selected from ($C_1$-$C_3$)alkyl, halo and ($C_1$-$C_6$) haloalkyl, preferably from methyl, fluorine and trifluoromethyl; and J is H.

According to preferred embodiments, the invention refers to at least one of the compounds listed in the table 1 below and pharmaceutical acceptable salts thereof.

TABLE 1

List of preferred compounds having Formula (I)

| Ex. No. | Structure | Chemical name |
|---|---|---|
| Example 3 | 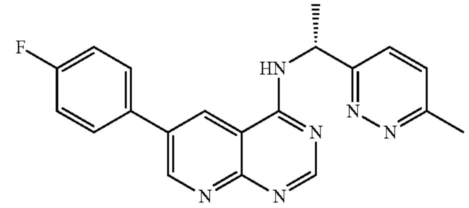 [SMILES: Cc1ccc([C@@H](C)Nc2ncnc3ncc(-c4ccc(F)cc4)cc23)nn1] | (R)-6-(4-fluorophenyl)-N-(1-(6-methylpyridazin-3-yl)ethyl)pyrido[2,3-d]pyrimidin-4-amine |
| Example 7 | 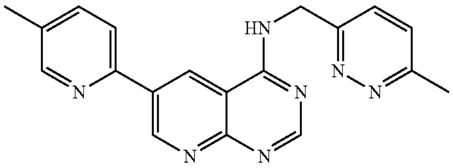 | N-((6-Methylpyridazin-3-yl)methyl)-6-(5-methylpyridin-2-yl)pyrido[2,3-d]pyrimidin-4-amine |
| Example 9 | 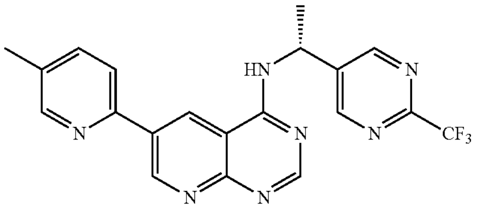 [SMILES: Cc1ccc(-c2cnc3ncnc(N[C@H](C)c4cnc(C(F)(F)F)nc4)c3c2)nc1] | (R)-6-(5-Methylpyridin-2-yl)-N-(1-(2-(trifluoromethyl)pyrimidin-5-yl)ethyl)pyrido[2,3-d]pyrimidin-4-amine |
| Example 11 | 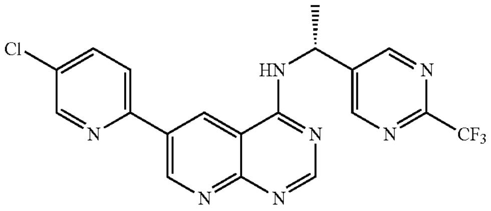 [SMILES: C[C@@H](Nc1ncnc2ncc(-c3ccc(Cl)cn3)cc12)c1cnc(C(F)(F)F)nc1] | (R)-6-(5-Chloropyridin-2-yl)-N-(1-(2-(trifluoromethyl)pyrimidin-5-yl)ethyl)pyrido[2,3-d]pyrimidin-4-amine |
| Example 13 | 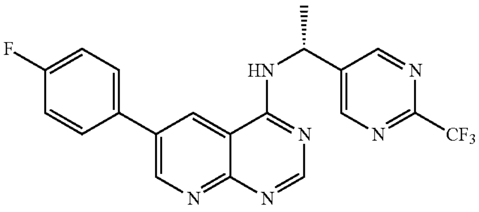 [SMILES: C[C@@H](Nc1ncnc2ncc(-c3ccc(F)cc3)cc12)c1cnc(C(F)(F)F)nc1] | (R)-6-(4-Fluorophenyl)-N-(1-(2-(trifluoromethyl)pyrimidin-5-yl)ethyl)pyrido[2,3-d]pyrimidin-4-amine |
| Example 14 | 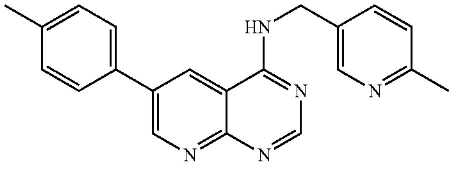 | N-((6-methylpyridin-3-yl)methyl)-6-(p-tolyl)pyrido[2,3-d]pyrimidin-4-amine |
| Example 15 | 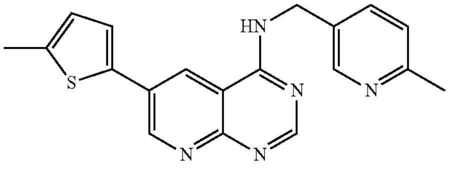 | N-((6-methylpyridin-3-yl)methyl)-6-(5-methylthiophen-2-yl)pyrido[2,3-d]pyrimidin-4-amine |

TABLE 1-continued

| List of preferred compounds having Formula (I) | | |
|---|---|---|
| Ex. No. | Structure | Chemical name |
| Example 19 | 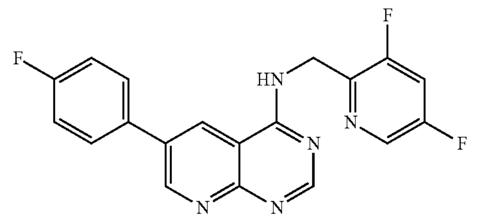 [SMILES: Fc1ccc(-c2cnc3ncnc(NCc4ncc(F)cc4F)c3c2)cc1] | N-((3,5-difluoropyridin-2-yl)methyl)-6-(4-fluorophenyl)pyrido[2,3-d]pyrimidin-4-amine |
| Example 27 | 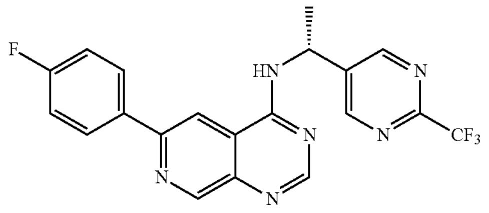 | 6-(4-Fluorophenyl)-N-[(1R)-1-[2-(trifluoromethyl)pyrimidin-5-yl]ethyl]pyrido[3,4-d]pyrimidin-4-amine |
| Example 32 | 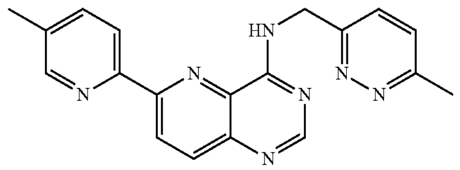 | N-((6-methylpyridazin-3-yl)methyl)-6-(5-methylpyridin-2-yl)pyrido[3,2-d]-pyrimidin-4-amine |
| Example 34 | 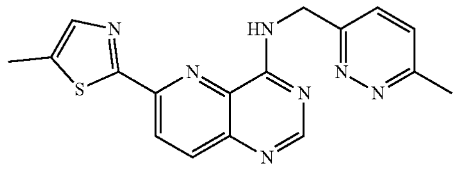 | N-[(6-methylpyridazin-3-yl)methyl]-6-(5-methylthiazol-2-yl)pyrido[3,2-d]pyrimidin-4-amine |
| Example 42 | 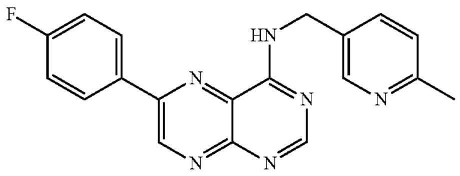 [SMILES: Cc1ccc(CNc2ncnc3ncc(-c4ccc(F)cc4)nc23)cn1] | 6-(4-Fluorophenyl)-N-((6-methylpyridin-3-yl)methyl)pteridin-4-amine |
| Example 45 | 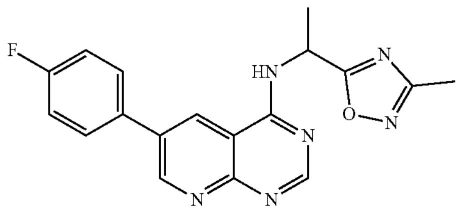 [SMILES: Cc1noc(C(C)Nc2ncnc3ncc(-c4ccc(F)cc4)cc23)n1] | Single enantiomer 1 of 6-(4-fluorophenyl)-N-[1-(3-methyl-1,2,4-oxadiazol-5-yl)ethyl]pyrido[2,3-d]pyrimidin-4-amine |
| Example 46 | 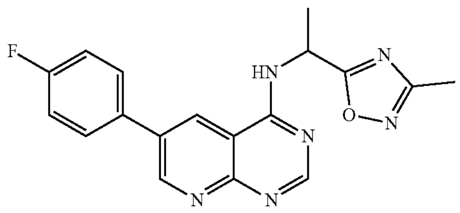 [SMILES: Cc1noc(C(C)Nc2ncnc3ncc(-c4ccc(F)cc4)cc23)n1] | Single enantiomer 2 of 6-(4-fluorophenyl)-N-[1-(3-methyl-1,2,4-oxadiazol-5-yl)ethyl]pyrido[2,3-d]pyrimidin-4-amine |

TABLE 1-continued

| List of preferred compounds having Formula (I) | | |
|---|---|---|
| Ex. No. | Structure | Chemical name |
| Example 49 | 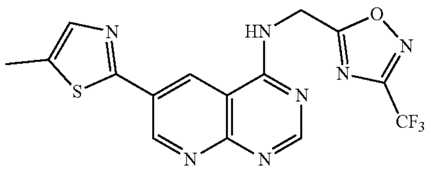 [SMILES: Cc1cnc(-c2cnc3ncnc(NCc4nc(C(F)(F)F)no4)c3c2)s1] | 6-(5-methylthiazol-2-yl)-N-[[3-(trifluoromethyl)-1,2,4-oxadiazol-5-yl]methyl]pyrido[2,3-d]pyrimidin-4-amine |
| Example 50 | 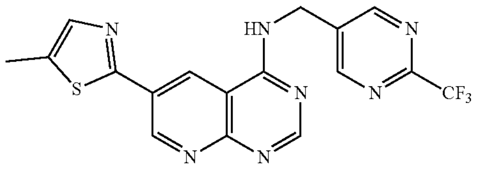 [SMILES: Cc1cnc(-c2cnc3ncnc(NCc4cnc(C(F)(F)F)nc4)c3c2)s1] | 6-(5-methylthiazol-2-yl)-N-[[2-(trifluoromethyl)pyrimidin-5-yl]methyl]pyrido[2,3-d]pyrimidin-4-amine |
| Example 51 | 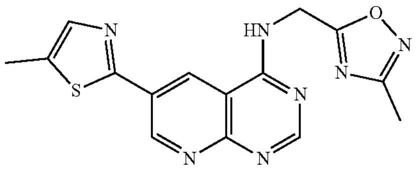 [SMILES: Cc1noc(CNc2ncnc3ncc(-c4ncc(C)s4)cc23)n1] | N-[(3-methyl-1,2,4-oxadiazol-5-yl)methyl]-6-(5-methylthiazol-2-yl)pyrido[2,3-d]pyrimidin-4-amine |
| Example 52 | 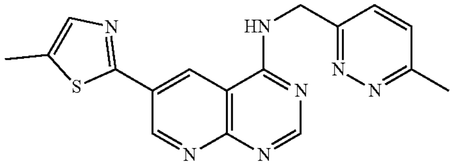 | N-[(6-methylpyridazin-3-yl)methyl]-6-(5-methylthiazol-2-yl)pyrido[2,3-d]pyrimidin-4-amine |
| Example 63 | 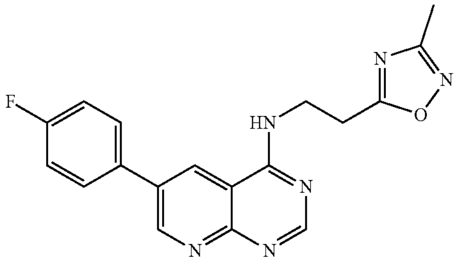 [SMILES: Cc1noc(CCNc2ncnc3ncc(-c4ccc(F)cc4)cc23)n1] | 6-(4-fluorophenyl)-N-(2-(3-methyl-1,2,4-oxadiazol-5-yl)ethyl)pyrido[2,3-d]pyrimidin-4-amine |
| Example 65 | 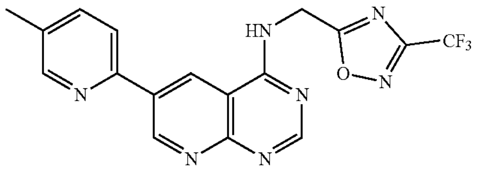 [SMILES: Cc1ccc(-c2cnc3ncnc(NCc4nc(C(F)(F)F)no4)c3c2)nc1] | 6-(5-methylpyridin-2-yl)-N-((3-(trifluoromethyl)-1,2,4-oxadiazol-5-yl)methyl)pyrido[2,3-d]pyrimidin-4-amine |
| Example 66 | 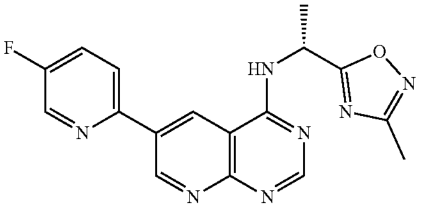 [SMILES: Cc1noc([C@@H](C)Nc2ncnc3ncc(-c4ccc(F)cn4)cc23)n1] | (6-(5-Fluoro-2-pyridyl)-N-[(1R)-1-(3-methyl-1,2,4-oxadiazol-5-yl)ethyl]pyrido[2,3-d]pyrimidin-4-amine |

TABLE 1-continued

List of preferred compounds having Formula (I)

| Ex. No. | Structure | Chemical name |
|---|---|---|
| Example 67 | 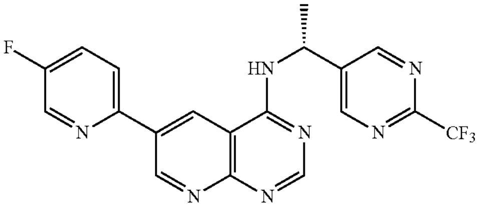 [SMILES: C[C@@H](Nc1ncnc2ncc(-c3ccc(F)cn3)cc12)c1cnc(C(F)(F)F)nc1] | (R)-6-(5-fluoropyridin-2-yl)-N-(1-(2-(trifluoromethyl)pyrimidin-5-yl)ethyl)pyrido[2,3-d]pyrimidin-4-amine |
| Example 68 | 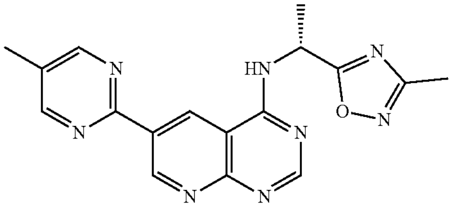 | N-[(1R)-1-(3-methyl-1,2,4-oxadiazol-5-yl)ethyl]-6-(5-methylpyrimidin-2-yl)pyrido[2,3-d]pyrimidin-4-amine |
| Example 69 | 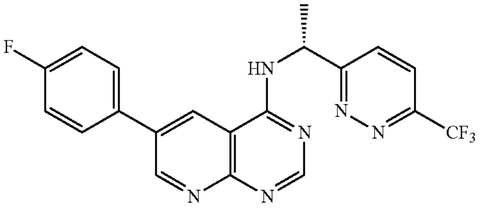 [SMILES: C[C@@H](Nc1ncnc2ncc(-c3ccc(F)cc3)cc12)c1ccc(C(F)(F)F)nn1] | 6-(4-fluorophenyl)-N-[(1R)-1-[6-(trifluoromethyl)pyridazin-3-yl]ethyl]pyrido[2,3-d]pyrimidin-4-amine |
| Example 70 | 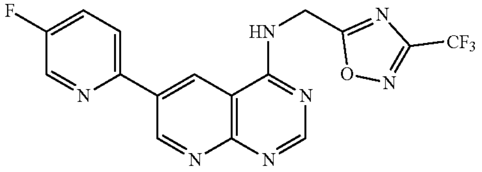 [SMILES: Fc1ccc(-c2cnc3ncnc(NCc4nc(C(F)(F)F)no4)c3c2)nc1] | 6-(5-fluoropyridin-2-yl)-N-((3-(trifluoromethyl)-1,2,4-oxadiazol-5-yl)methyl)pyrido[2,3-d]pyrimidin-4-amine |
| Example 71 | 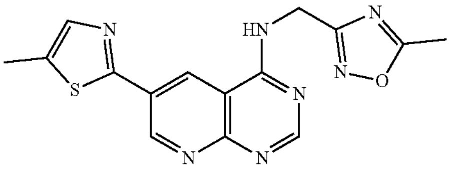 | N-[(5-methyl-1,2,4-oxadiazol-3-yl)methyl]-6-(5-methylthiazol-2-yl)pyrido[2,3-d]pyrimidin-4-amine |
| Example 72 | 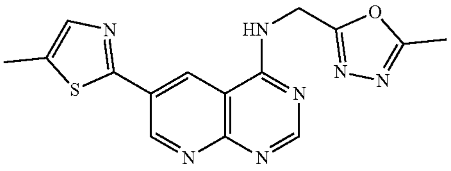 | N-[(5-methyl-1,3,4-oxadiazol-2-yl)methyl]-6-(5-methylthiazol-2-yl)pyrido[2,3-d]pyrimidin-4-amine |
| Example 73 | 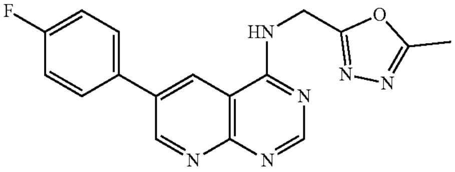 [SMILES: Cc1nnc(CNc2ncnc3ncc(-c4ccc(F)cc4)cc23)o1] | 6-(4-fluorophenyl)-N-[(5-methyl-1,3,4-oxadiazol-2-yl)methyl]pyrido[2,3-d]pyrimidin-4-amine |
| Example 75 | 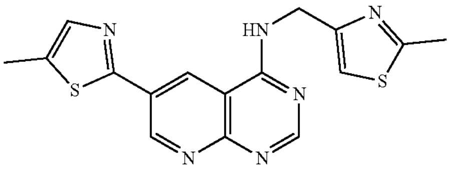 | 6-(5-methylthiazol-2-yl)-N-[(2-methylthiazol-4-yl)methyl]pyrido[2,3-d]pyrimidin-4-amine |

TABLE 1-continued

| List of preferred compounds having Formula (I) | | |
|---|---|---|
| Ex. No. | Structure | Chemical name |
| Example 76 | 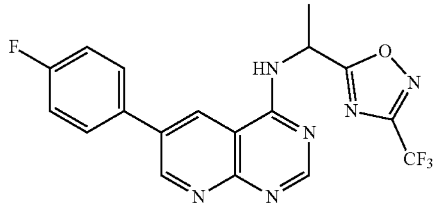 [SMILES: CC(Nc1ncnc2ncc(-c3ccc(F)cc3)cc12)c1nc(C(F)(F)F)no1] | 6-(4-fluorophenyl)-N-[1-[3-(trifluoromethyl)-1,2,4-oxadiazol-5-yl]ethyl]pyrido[2,3-d]pyrimidin-4-amine |
| Example 77 | 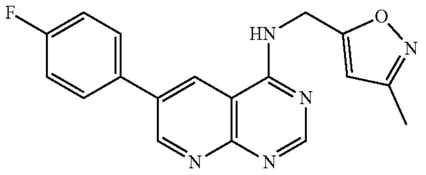 [SMILES: Cc1cc(CNc2ncnc3ncc(-c4ccc(F)cc4)cc23)on1] | 6-(4-fluorophenyl)-N-[(3-methylisoxazol-5-yl)methyl]pyrido[2,3-d]pyrimidin-4-amine |
| Example 78 | 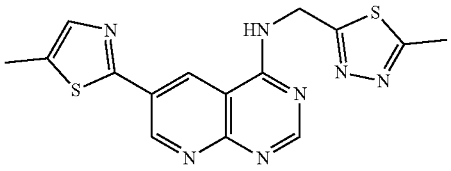 | N-[(5-methyl-1,3,4-thiadiazol-2-yl)methyl]-6-(5-methylthiazol-2-yl)pyrido[2,3-d]pyrimidin-4-amine |
| Example 79 | 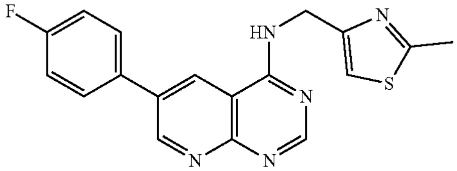 [SMILES: Cc1nc(CNc2ncnc3ncc(-c4ccc(F)cc4)cc23)cs1] | 6-(4-fluorophenyl)-N-[(2-methylthiazol-4-yl)methyl]pyrido[2,3-d]pyrimidin-4-amine |
| Example 80 | 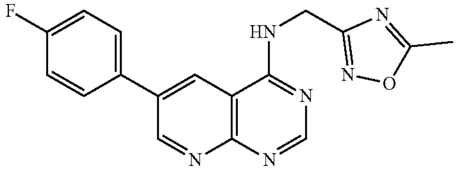 [SMILES: Cc1nc(CNc2ncnc3ncc(-c4ccc(F)cc4)cc23)no1] | 6-(4-fluorophenyl)-N-[(5-methyl-1,2,4-oxadiazol-3-yl)methyl]pyrido[2,3-d]pyrimidin-4-amine |
| Example 82 | 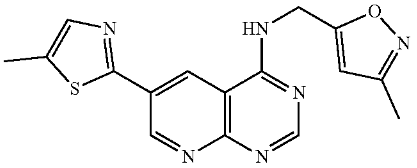 [SMILES: Cc1cc(CNc2ncnc3ncc(-c4ncc(C)s4)cc23)on1] | N-[(3-methylisoxazol-5-yl)methyl]-6-(5-methylthiazol-2-yl)pyrido[2,3-d]pyrimidin-4-amine |
| Example 83 | 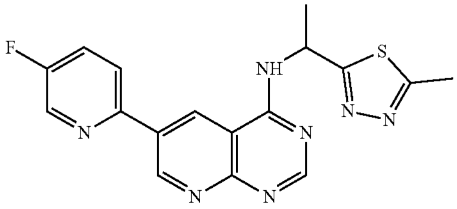 [SMILES: Cc1nnc(C(C)Nc2ncnc3ncc(-c4ccc(F)cn4)cc23)s1] | Single enantiomer 1 of 6-(5-fluoro-2-pyridyl)-N-[1-(5-methyl-1,3,4-thiadiazol-2-yl)ethyl]pyrido[2,3-d]pyrimidin-4-amine |

TABLE 1-continued

| List of preferred compounds having Formula (I) | | |
|---|---|---|
| Ex. No. | Structure | Chemical name |
| (Example 84, | 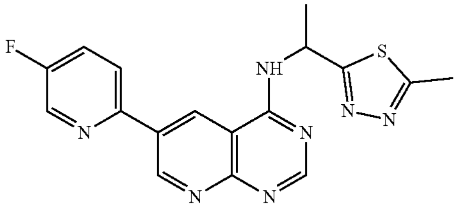 [SMILES: Cc1nnc(C(C)Nc2ncnc3ncc(-c4ccc(F)cn4)cc23)s1] | Single enantiomer 2 of 6-(5-fluoro-2-pyridyl)-N-[1-(5-methyl-1,3,4-thiadiazol-2-yl)ethyl]pyrido[2,3-d]pyrimidin-4-amine |
| Example 87 | 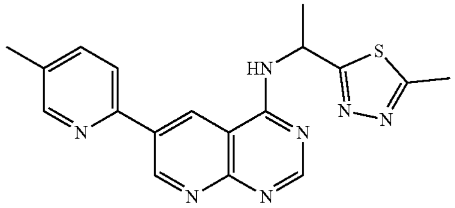 | Single enantiomer 1 of N-(1-(5-methyl-1,3,4-thiadiazol-2-yl)ethyl)-6-(5-methylpyridin-2-yl)pyrido[2,3-d]pyrimidin-4-amine |
| Example 88 | 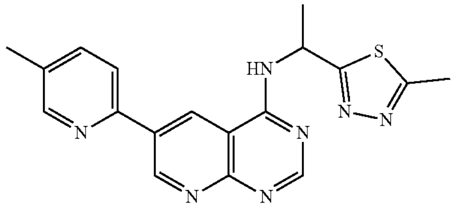 | Single enantiomer 2 of N-(1-(5-methyl-1,3,4-thiadiazol-2-yl)ethyl)-6-(5-methylpyridin-2-yl)pyrido[2,3-d]pyrimidin-4-amine |
| Example 91 | 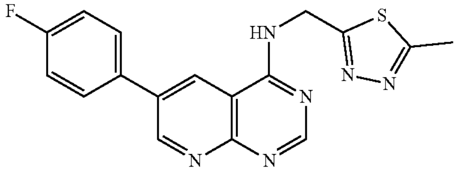 [SMILES: Cc1nnc(CNc2ncnc3ncc(-c4ccc(F)cc4)cc23)s1] | 6-(4-Fluorophenyl)-N-[(5-methyl-1,3,4-thiadiazol-2-yl)methyl]pyrido[2,3-d]pyrimidin-4-amine |
| Example 92 | 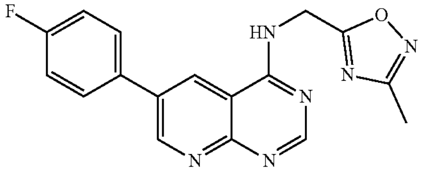 [SMILES: Cc1noc(CNc2ncnc3ncc(-c4ccc(F)cc4)cc23)n1] | 6-(4-fluorophenyl)-N-[(3-methyl-1,2,4-oxadiazol-5-yl)methyl]pyrido[2,3-d]pyrimidin-4-amine |
| Example 93 | 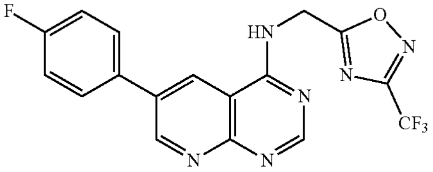 [SMILES: Fc1ccc(-c2cnc3ncnc(NCc4nc(C(F)(F)F)no4)c3c2)cc1] | 6-(4-fluorophenyl)-N-[[3-(trifluoromethyl)-1,2,4-oxadiazol-5-yl]methyl]pyrido[2,3-d]pyrimidin-4-amine |
| Example 94 | 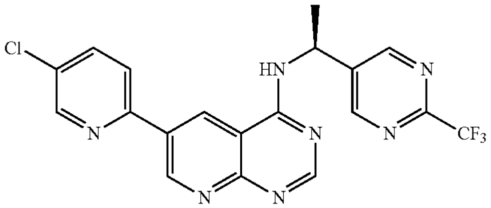 [SMILES: C[C@H](Nc1ncnc2ncc(-c3ccc(Cl)cn3)cc12)c1cnc(C(F)(F)F)nc1] | 6-(5-chloro-2-pyridyl)-N-[(1S)-1-[2-(trifluoromethyl)pyrimidin-5-yl]ethyl]pyrido[2,3-d]pyrimidin-4-amine |

TABLE 1-continued

List of preferred compounds having Formula (I)

| Ex. No. | Structure | Chemical name |
| --- | --- | --- |
| Example 95 | 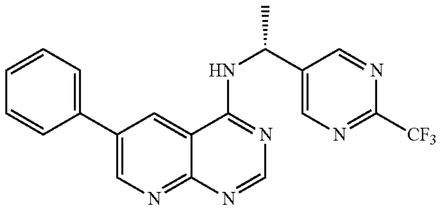 [SMILES: C[C@@H](Nc1ncnc2ncc(-c3ccccc3)cc12)c1cnc(C(F)(F)F)nc1] | 6-phenyl-N-[(1R)-1-[2-(trifluoromethyl)pyrimidin-5-yl]ethyl]pyrido[2,3-d]pyrimidin-4-amine |
| Example 102 | 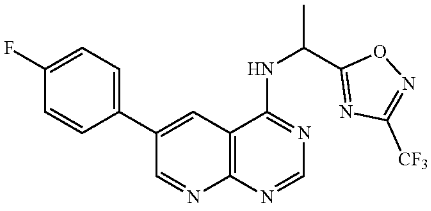 [SMILES: CC(Nc1ncnc2ncc(-c3ccc(F)cc3)cc12)c1nc(C(F)(F)F)no1] | Single enantiomer 1 of 6-(4-fluorophenyl)-N-[1-[3-(trifluoromethyl)-1,2,4-oxadiazol-5-yl]ethyl]pyrido[2,3-d]pyrimidin-4-amine |
| Example 103 | 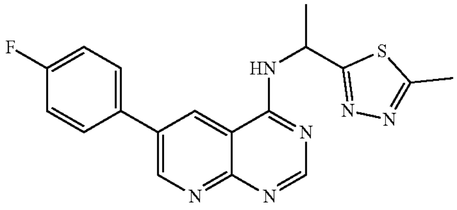 [SMILES: Cc1nnc(C(C)Nc2ncnc3ncc(-c4ccc(F)cc4)cc23)s1] | Single enantiomer 1 of 6-(4-fluorophenyl)-N-(1-(5-methyl-1,3,4-thiadiazol-2-yl)ethyl)pyrido[2,3-d]pyrimidin-4-amine |
| Example 104 | 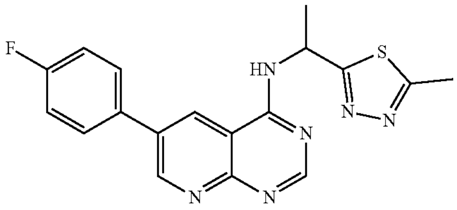 [SMILES: Cc1nnc(C(C)Nc2ncnc3ncc(-c4ccc(F)cc4)cc23)s1] | Single enantiomer 2 of 6-(4-fluorophenyl)-N-(1-(5-methyl-1,3,4-thiadiazol-2-yl)ethyl)pyrido[2,3-d]pyrimidin-4-amine |
| Example 105 | 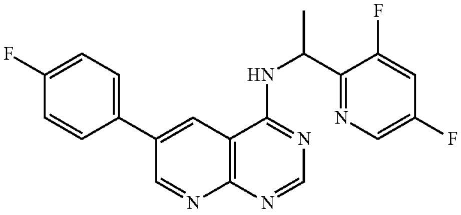 [SMILES: CC(Nc1ncnc2ncc(-c3ccc(F)cc3)cc12)c1ncc(F)cc1F] | Single enantiomer 1 of N-[1-(3,5-difluoro-2-pyridyl)ethyl]-6-(4-fluorophenyl)pyrido[2,3-d]pyrimidin-4-amine |
| Example 106 | 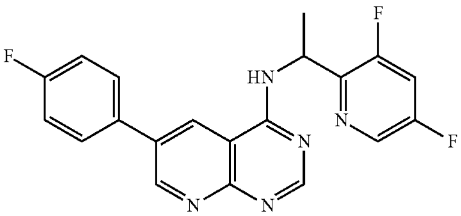 [SMILES: CC(Nc1ncnc2ncc(-c3ccc(F)cc3)cc12)c1ncc(F)cc1F] | Single enantiomer 2 of N-[1-(3,5-difluoro-2-pyridyl)ethyl]-6-(4-fluorophenyl)pyrido[2,3-d]pyrimidin-4-amine |
| Example 63a | 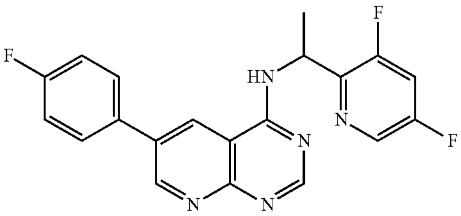 [SMILES: CC(Nc1ncnc2ncc(-c3ccc(F)cc3)cc12)c1ncc(F)cc1F] | N-[1-(3,5-difluoro-2-pyridyl)ethyl]-6-(4-fluorophenyl)pyrido[2,3-d]pyrimidin-4-amine |

TABLE 1-continued

| List of preferred compounds having Formula (I) | | |
|---|---|---|
| Ex. No. | Structure | Chemical name |
| Example 107 | 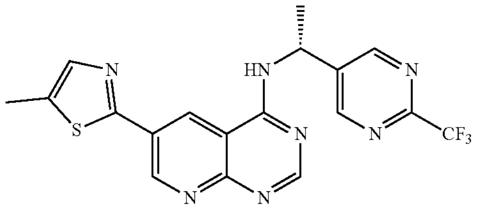 [SMILES: Cc1cnc(-c2cnc3ncnc(N[C@H](C)c4cnc(C(F)(F)F)nc4)c3c2)s1] | 6-(5-methylthiazol-2-yl)-N-[(1R)-1-[2-(trifluoromethyl)pyrimidin-5-yl]ethyl]pyrido[2,3-d]pyrimidin-4-amine |

In a preferred embodiment, the invention is directed to compounds of formula (I) as defined above, wherein $X_1$ is N, $X_2$ and $X_3$ are CH, represented by the formula (Ia)

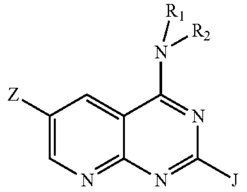
(Ia)

Z is H or selected from the group consisting of ($C_1$-$C_4$) alkyl-, heteroaryl, aryl, wherein any of such heteroaryl and aryl may be optionally substituted by one or more groups selected from ($C_1$-$C_3$)alkyl, halo, CN, ($R^AR^B$) NC(O)—;

R1 is H;

R2 is selected from the group consisting of heteroaryl ($C_1$-$C_4$)alkyl-, ($C_3$-$C_8$)heterocycloalkyl-($C_1$-$C_6$)alkyl, wherein any of such alkyl, heteroaryl may be optionally substituted by one or more groups selected from ($C_1$-$C_3$)alkyl, halo, $R^AO$($C_1$-$C_4$)alkylene-, ($C_1$-$C_6$) haloalkyl, $R^AO$—;

$R^A$ and $R^B$ are at each occurrence independently H or ($C_1$-$C_4$)alkyl-, or $R^A$ and $R^B$ may form together with the nitrogen atom to which they are attached a 6 membered saturated heterocyclic monocyclic ring system optionally containing a further heteroatom which is nitrogen, which may be optionally substituted by $R^C$(O)C—;

$R^C$ is ($C_1$-$C_6$)alkyl;

J is H or ($R^AR^B$)N—.

In a further preferred embodiment, the invention refers to compound of formula (Ia) wherein Z is H or selected from the group consisting of ($C_1$-$C_4$)alkyl-, preferably methyl, ($R^AR^B$)N—, wherein $R^A$ is H and $R^B$ is phenyl, said phenyl optionally further substituted by one or more fluorine;

heteroaryl, which is pyridinyl, thiazolyl, thiophenyl, each of said heteroaryl is further optionally substituted by one or more groups selected from methyl or chlorine;

aryl preferably phenyl, each of said aryl is further optionally substituted by one or more groups selected from methyl, fluorine, CN and ($R^AR^B$)NC (O)— where $R^A$ and $R^B$ are H;

$R_1$ is H;

R2 is selected from the group consisting of heteroaryl($C_1$-$C_4$)alkyl-, preferably (pyridazyl)methyl, (pyridazyl)ethyl (pyridinyl)methyl, (pyridinyl)ethyl, (pyrimidyl)ethyl, (oxadiazolyl)ethyl, heteroaryl ($C_1$-$C_6$) alkoxyl, preferably pyridinyloxy, heteroaryl-($C_1$-$C_6$)hydroxyalkyl, preferably (pyridinyl) ethanol, ($C_3$-$C_8$)heterocycloalkyl-($C_1$-$C_6$)alkyl, preferably (morpholinyl)ethyl, each of said heteroaryl is optionally substituted by one or more groups selected from methyl, fluorine, trifluoromethyl, $R^AO$— wherein $R^A$ is methyl;

J is H or ($R^AR^B$)N— wherein $R^A$ and $R^B$ form together with the nitrogen atom to which they are attached a 6 membered saturated heterocyclic monocyclic ring system optionally containing a further heteroatom which is nitrogen, said heterocyclic radical is in its turn optionally further substituted by $R^C$(O)C— wherein $R^C$ is methyl.

According to preferred embodiments, the invention refers to at least one of the compounds listed in the table 2 below and pharmaceutical acceptable salts thereof.

TABLE 2

| List of preferred compounds having Formula (Ia) | | |
|---|---|---|
| Ex. No. | Structure | Chemical name |
| Example 1 | 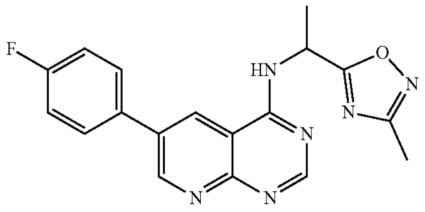 [SMILES: Cc1noc(C(C)Nc2ncnc3ncc(-c4ccc(F)cc4)cc23)n1] | 6-(4-Fluorophenyl)-N-[1-(3-methyl-1,2,4-oxadiazol-5-yl)ethyl]pyrido[2,3-d]pyrimidin-4-amine |

TABLE 2-continued

| List of preferred compounds having Formula (Ia) | | |
|---|---|---|
| Ex. No. | Structure | Chemical name |
| Example 2 | 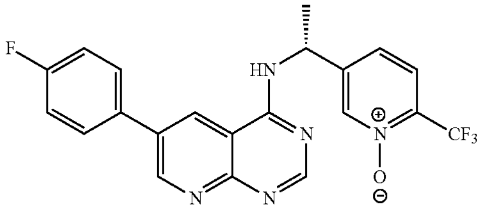 [SMILES: C[C@@H](Nc1ncnc2ncc(-c3ccc(F)cc3)cc12)c1ccc(C(F)(F)F)[n+]([O-])c1] | (R)-5-(1-((6-(4-fluorophenyl)pyrido[2,3-d]pyrimidin-4-yl)amino)ethyl)-2-(trifluoromethyl)pyridine 1-oxide |
| Example 3 | 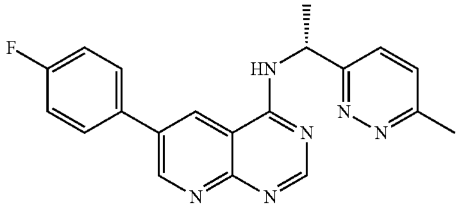 [SMILES: Cc1ccc([C@@H](C)Nc2ncnc3ncc(-c4ccc(F)cc4)cc23)nn1] | (R)-6-(4-fluorophenyl)-N-(1-(6-methylpyridazin-3-yl)ethyl)pyrido[2,3-d]pyrimidin-4-amine |
| Example 4 | 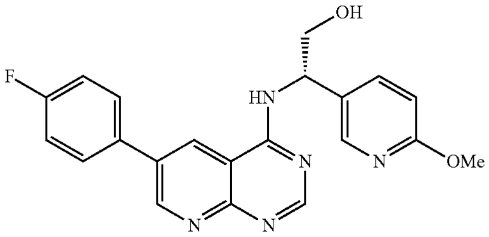 [SMILES: COc1ccc([C@@H](CO)Nc2ncnc3ncc(-c4ccc(F)cc4)cc23)cn1] | (S)-2-((6-(4-fluorophenyl)pyrido[2,3-d]pyrimidin-4-yl)amino)-2-(6-methoxypyridin-3-yl)ethan-1-ol |
| Example 5 | 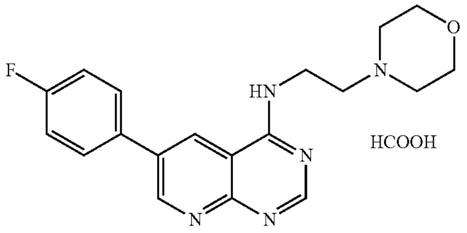 [SMILES: Fc1ccc(-c2cnc3ncnc(NCCN4CCOCC4)c3c2)cc1 ; "HCOOH"] | 6-(4-fluorophenyl)-N-(2-morpholinoethyl)pyrido[2,3-d]pyrimidin-4-amine formate |
| Example 6 | 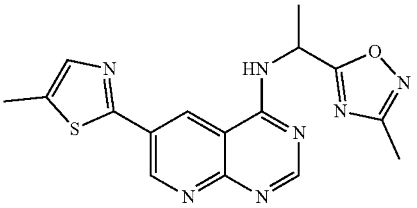 [SMILES: Cc1noc(C(C)Nc2ncnc3ncc(-c4ncc(C)s4)cc23)n1] | N-(1-(3-Methyl-1,2,4-oxadiazol-5-yl)ethyl)-6-(5-methylthiazol-2-yl)pyrido[2,3-d]-pyrimidin-4-amine |
| Example 7 | 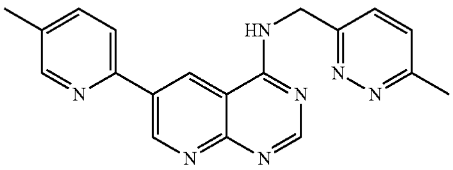 | N-((6-Methylpyridazin-3-yl)methyl)-6-(5-methylpyridin-2-yl)pyrido[2,3-d]pyrimidin-4-amine |
| Example 8 | 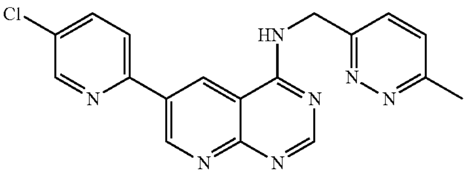 [SMILES: Cc1ccc(CNc2ncnc3ncc(-c4ccc(Cl)cn4)cc23)nn1] | 6-(5-Chloropyridin-2-yl)-N-((6-methylpyridazin-3-yl)methyl)pyrido[2,3-d]pyrimidin-4-amine |

TABLE 2-continued

List of preferred compounds having Formula (Ia)

| Ex. No. | Structure | Chemical name |
| --- | --- | --- |
| Example 9 | 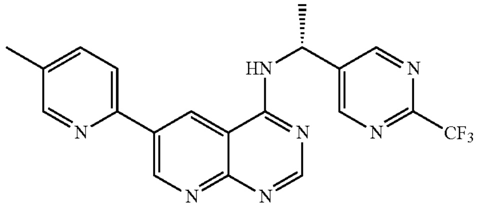 [SMILES: Cc1ccc(-c2cnc3ncnc(N[C@H](C)c4cnc(C(F)(F)F)nc4)c3c2)nc1] | (R)-6-(5-Methylpyridin-2-yl)-N-(1-(2-(trifluoromethyl)pyrimidin-5-yl)ethyl)pyrido[2,3-d]pyrimidin-4-amine |
| Example 10 | 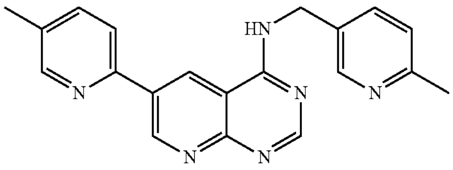 | 6-(5-methylpyridin-2-yl)-N-((6-methylpyridin-3-yl)methyl)pyrido[2,3-d]pyrimidin-4-amine |
| Example 11 | 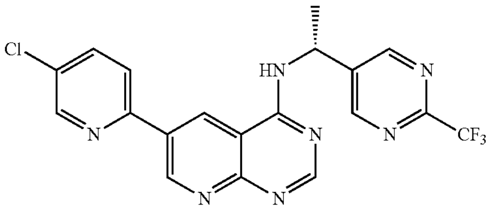 [SMILES: C[C@@H](Nc1ncnc2ncc(-c3ccc(Cl)cn3)cc12)c1cnc(C(F)(F)F)nc1] | (R)-6-(5-Chloropyridin-2-yl)-N-(1-(2-(trifluoromethyl)pyrimidin-5-yl)ethyl)pyrido[2,3-d]pyrimidin-4-amine |
| Example 12 | 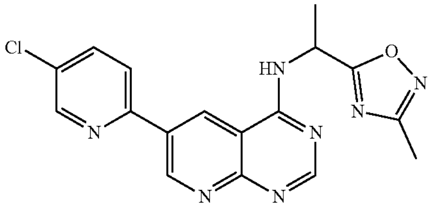 [SMILES: Cc1noc(C(C)Nc2ncnc3ncc(-c4ccc(Cl)cn4)cc23)n1] | 6-(5-Chloropyridin-2-yl)-N-(1-(3-methyl-1,2,4-oxadiazol-5-yl)ethyl)pyrido[2,3-d]pyrimidin-4-amine |
| Example 13 | 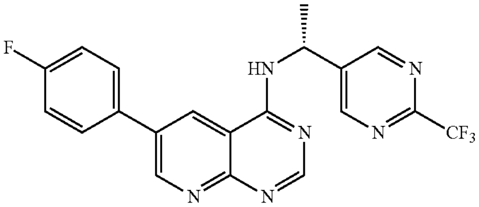 | (R)-6-(4-Fluorophenyl)-N-(1-(2-(trifluoromethyl)pyrimidin-5-yl)ethyl)pyrido[2,3-d]pyrimidin-4-amine |
| Example 14 | 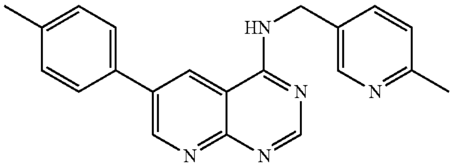 | N-((6-methylpyridin-3-yl)methyl)-6-(p-tolyl)pyrido[2,3-d]pyrimidin-4-amine |
| Example 15 | 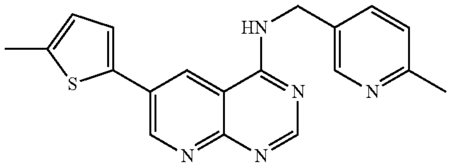 | N-((6-methylpyridin-3-yl)methyl)-6-(5-methylthiophen-2-yl)pyrido[2,3-d]pyrimidin-4-amine |

TABLE 2-continued

| List of preferred compounds having Formula (Ia) | | |
|---|---|---|
| Ex. No. | Structure | Chemical name |
| Example 16 | 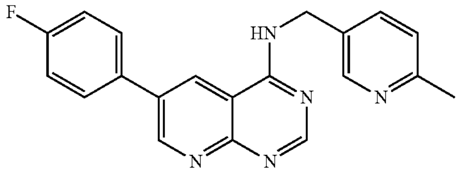 [SMILES: Cc1ccc(CNc2ncnc3ncc(-c4ccc(F)cc4)cc23)cn1] | 6-(4-fluorophenyl)-N-((6-methylpyridin-3-yl)methyl)pyrido[2,3-d]pyrimidin-4-amine |
| Example 17 | 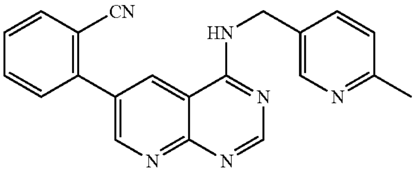 [SMILES: Cc1ccc(CNc2ncnc3ncc(-c4ccccc4C#N)cc23)cn1] | 2-(4-(((6-methylpyridin-3-yl)methyl)amino)pyrido[2,3-d]pyrimidin-6-yl)benzonitrile |
| Example 18 | 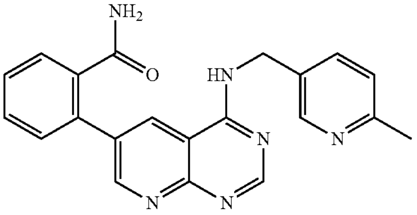 [SMILES: Cc1ccc(CNc2ncnc3ncc(-c4ccccc4C(N)=O)cc23)cn1] | 2-(4-(((6-methylpyridin-3-yl)methyl)amino)pyrido[2,3-d]pyrimidin-6-yl)benzamide |
| Example 19 | 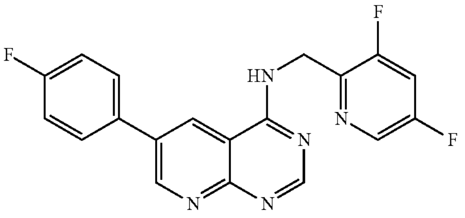 [SMILES: Fc1ccc(-c2cnc3ncnc(NCc4ncc(F)cc4F)c3c2)cc1] | N-((3,5-difluoropyridin-2-yl)methyl)-6-(4-fluorophenyl)pyrido[2,3-d]pyrimidin-4-amine |
| Example 20 | 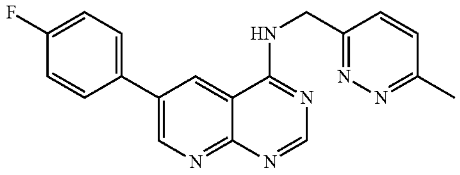 [SMILES: Cc1ccc(CNc2ncnc3ncc(-c4ccc(F)cc4)cc23)nn1] | 6-(4-fluorophenyl)-N-((6-methylpyridazin-3-yl)methyl)pyrido[2,3-d]pyrimidin-4-amine |
| Example 21 | 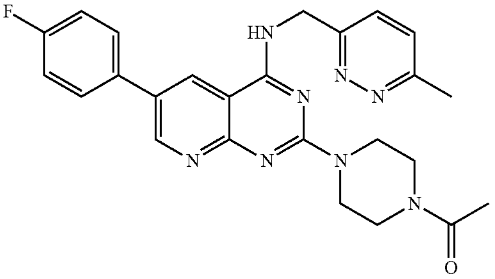 [SMILES: CC(=O)N1CCN(c2nc(NCc3ccc(C)nn3)c3cc(-c4ccc(F)cc4)cnc3n2)CC1] | 1-(4-(6-(4-fluorophenyl)-4-(((6-methylpyridazin-3-yl)methyl)amino)pyrido[2,3-d]pyrimidin-2-yl)piperazin-1-yl)ethan-l-one |
| Example 22 | 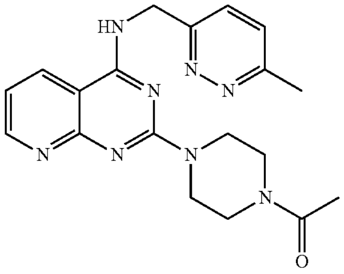 [SMILES: CC(=O)N1CCN(c2nc(NCc3ccc(C)nn3)c3cccnc3n2)CC1] | 1-(4-(4-(((6-methylpyridazin-3-yl)methyl)amino)pyrido[2,3-d]pyrimidin-2-yl)piperazin-1-yl)ethan-l-one |

TABLE 2-continued

List of preferred compounds having Formula (Ia)

| Ex. No. | Structure | Chemical name |
| --- | --- | --- |
| Example 23 | 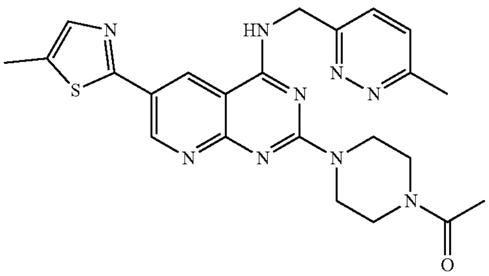 [SMILES: CC(=O)N1CCN(c2nc(NCc3ccc(C)nn3)c3cc(-c4ncc(C)s4)cnc3n2)CC1] | 1-(4-(4-(((6-Methylpyridazin-3-yl)methyl)amino)-6-(5-methylthiazol-2-yl)pyrido[2,3-d]pyrimidin-2-yl)piperazin-1-yl)ethan-l-one |
| Example 24 | 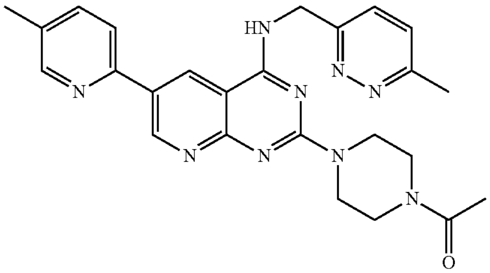 [SMILES: CC(=O)N1CCN(c2nc(NCc3ccc(C)nn3)c3cc(-c4ccc(C)cn4)cnc3n2)CC1] | 1-(4-(4-(((6-Methylpyridazin-3-yl)methyl)amino)-6-(5-methylpyridin-2-yl)pyrido[2,3-d]pyrimidin-2-yl)piperazin-1-yl)ethan-1-one |
| Example 25 | 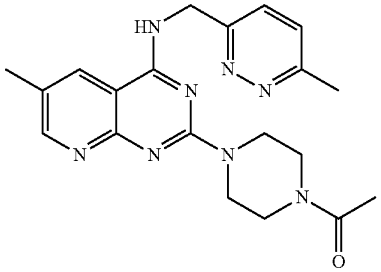 [SMILES: CC(=O)N1CCN(c2nc(NCc3ccc(C)nn3)c3cc(C)cnc3n2)CC1] | 1-(4-(6-Methyl-4-(((6-methylpyridazin-3-yl)methyl)amino)pyrido[2,3-d]pyrimidin-2-yl)piperazin-1-yl)ethan-1-one |
| Example 49 | 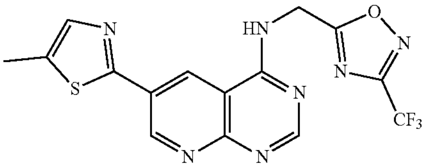 [SMILES: Cc1cnc(-c2cnc3ncnc(NCc4nc(C(F)(F)F)no4)c3c2)s1] | 6-(5-methylthiazol-2-yl)-N-[[3-(trifluoromethyl)-1,2,4-oxadiazol-5-yl]methyl]pyrido[2,3-d]pyrimidin-4-amine |
| Example 50 | 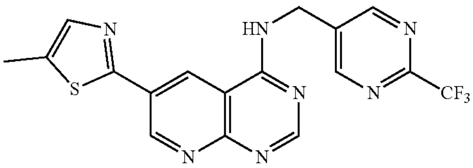 [SMILES: Cc1cnc(-c2cnc3ncnc(NCc4cnc(C(F)(F)F)nc4)c3c2)s1] | 6-(5-methylthiazol-2-yl)-N-[[2-(trifluoromethyl)pyrimidin-5-yl]methyl]pyrido[2,3-d]pyrimidin-4-amine |
| Example 51 | 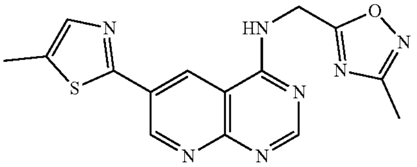 [SMILES: Cc1noc(CNc2ncnc3ncc(-c4ncc(C)s4)cc23)n1] | N-[(3-methyl-1,2,4-oxadiazol-5-yl)methyl]-6-(5-methylthiazol-2-yl)pyrido[2,3-d]pyrimidin-4-amine |
| Example 52 | 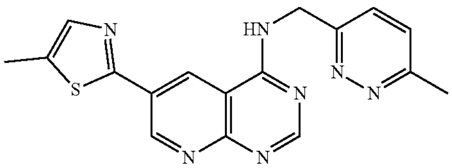 | N-[(6-methylpyridazin-3-yl)methyl]-6-(5-methylthiazol-2-yl)pyrido[2,3-d]pyrimidin-4-amine |

TABLE 2-continued

List of preferred compounds having Formula (Ia)

| Ex. No. | Structure | Chemical name |
| --- | --- | --- |
| Example 54 | 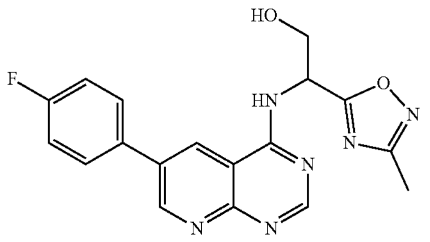 [SMILES: Cc1noc(C(CO)Nc2ncnc3ncc(-c4ccc(F)cc4)cc23)n1] | 2-((6-(4-fluorophenyl)pyrido[2,3-d]pyrimidin-4-yl)amino)-2-(5-methyl-1,2,4-oxadiazol-3-yl)ethan-1-ol |
| Example 55 | 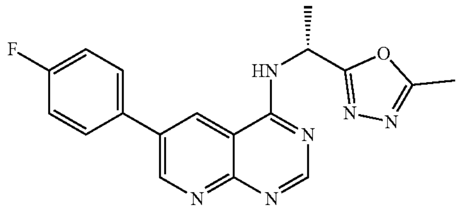 [SMILES: Cc1nnc([C@@H](C)Nc2ncnc3ncc(-c4ccc(F)cc4)cc23)o1] | (R)-6-(4-fluorophenyl)-N-(1-(5-methyl-1,3,4-oxadiazol-2-yl)ethyl)pyrido[2,3-d]pyrimidin-4-amine |
| Example 56 | 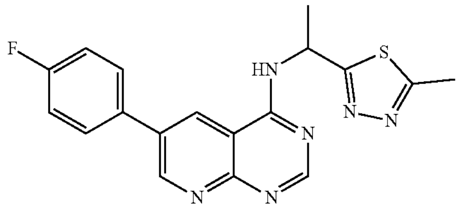 [SMILES: Cc1nnc(C(C)Nc2ncnc3ncc(-c4ccc(F)cc4)cc23)s1] | 6-(4-fluorophenyl)-N-(1-(5-methyl-1,3,4-thiadiazol-2-yl)ethyl)pyrido[2,3-d]pyrimidin-4-amine |
| Example 58 | 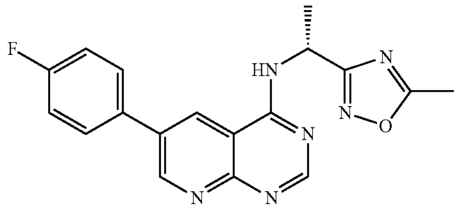 [SMILES: Cc1nc([C@@H](C)Nc2ncnc3ncc(-c4ccc(F)cc4)cc23)no1] | (R)-6-(4-fluorophenyl)-N-(1-(5-methyl-1,2,4-oxadiazol-3-yl)ethyl)pyrido[2,3-d]pyrimidin-4-amine |
| Example 59 | 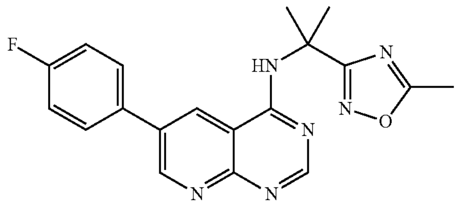 [SMILES: Cc1nc(C(C)(C)Nc2ncnc3ncc(-c4ccc(F)cc4)cc23)no1] | 6-(4-fluorophenyl)-N-(2-(3-methyl-1,2,4-oxadiazol-5-yl)propan-2-yl)pyrido[2,3-d]pyrimidin-4-amine |
| Example 60 | 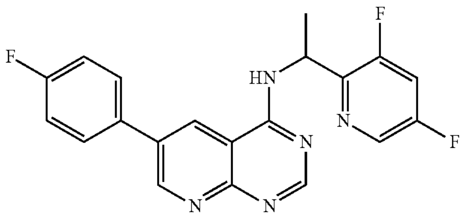 [SMILES: CC(Nc1ncnc2ncc(-c3ccc(F)cc3)cc12)c1ncc(F)cc1F] | N-(1-(3,5-difluoropyridin-2-yl)ethyl)-6-(4-fluorophenyl)pyrido[2,3-d]pyrimidin-4-amine |

TABLE 2-continued

List of preferred compounds having Formula (Ia)

| Ex. No. | Structure | Chemical name |
|---|---|---|
| Example 63 | 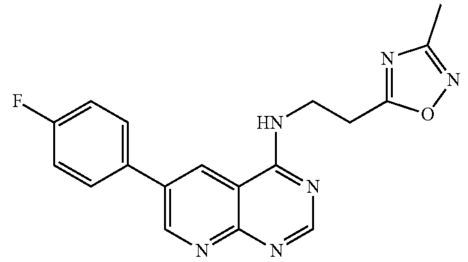 [SMILES: Cc1noc(CCNc2ncnc3ncc(-c4ccc(F)cc4)cc23)n1] | 6-(4-fluorophenyl)-N-(2-(3-methyl-1,2,4-oxadiazol-5-yl)ethyl)pyrido[2,3-d]pyrimidin-4-amine |
| Example 65 | 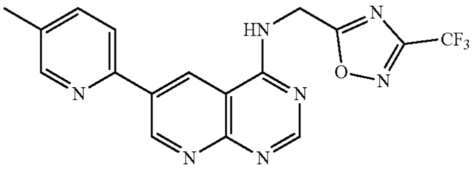 [SMILES: Cc1ccc(-c2cnc3ncnc(NCc4nc(C(F)(F)F)no4)c3c2)nc1] | 6-(5-methylpyridin-2-yl)-N-((3-(trifluoromethyl)-1,2,4-oxadiazol-5-yl)methyl)pyrido[2,3-d]pyrimidin-4-amine |
| Example 66 | 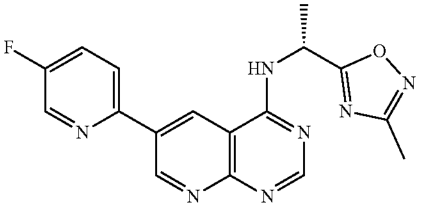 [SMILES: Cc1noc([C@@H](C)Nc2ncnc3ncc(-c4ccc(F)cn4)cc23)n1] | (6-(5-Fluoro-2-pyridyl)-N-[(1R)-1-(3-methyl-1,2,4-oxadiazol-5-yl)ethyl]pyrido[2,3-d]pyrimidin-4-amine |
| Example 67 | 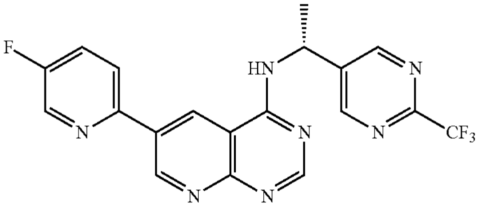 [SMILES: C[C@@H](Nc1ncnc2ncc(-c3ccc(F)cn3)cc12)c1cnc(C(F)(F)F)nc1] | (R)-6-(5-fluoropyridin-2-yl)-N-(1-(2-(trifluoromethyl)pyrimidin-5-yl)ethyl)pyrido[2,3-d]pyrimidin-4-amine |
| Example 68 | 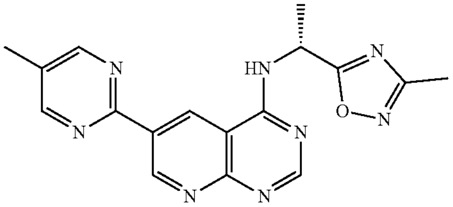 | N-[(1R)-1-(3-methyl-1,2,4-oxadiazol-5-yl)ethyl]-6-(5-methylpyrimidin-2-yl)pyrido[2,3-d]pyrimidin-4-amine |
| Example 69 | 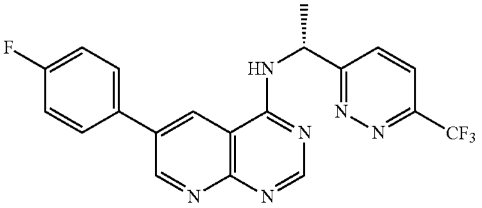 [SMILES: C[C@@H](Nc1ncnc2ncc(-c3ccc(F)cc3)cc12)c1ccc(C(F)(F)F)nn1] | 6-(4-fluorophenyl)-N-[(1R)-1-[6-(trifluoromethyl)pyridazin-3-yl]ethyl]pyrido[2,3-d]pyrimidin-4-amine |
| Example 70 | 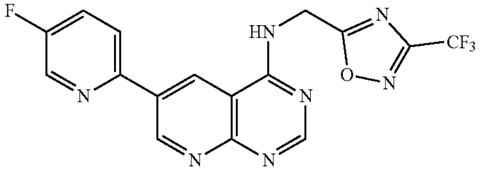 [SMILES: Fc1ccc(-c2cnc3ncnc(NCc4nc(C(F)(F)F)no4)c3c2)nc1] | 6-(5-fluoropyridin-2-yl)-N-((3-(trifluoromethyl)-1,2,4-oxadiazol-5-yl)methyl)pyrido[2,3-d]pyrimidin-4-amine |

TABLE 2-continued

List of preferred compounds having Formula (Ia)

| Ex. No. | Structure | Chemical name |
| --- | --- | --- |
| Example 71 | 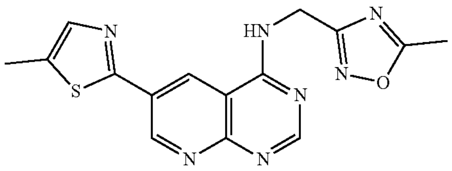 | N-[(5-methyl-1,2,4-oxadiazol-3-yl)methyl]-6-(5-methylthiazol-2-yl)pyrido[2,3-d]pyrimidin-4-amine |
| Example 72 | 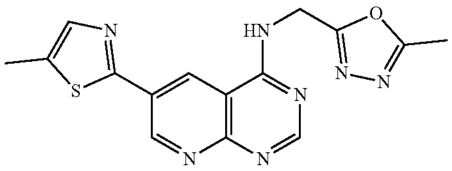 | N-[(5-methyl-1,3,4-oxadiazol-2-yl)methyl]-6-(5-methylthiazol-2-yl)pyrido[2,3-d]pyrimidin-4-amine |
| Example 73 | 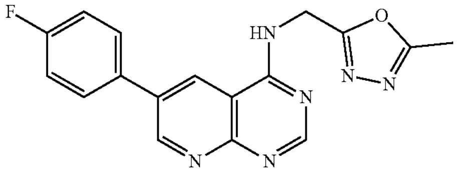 [SMILES: Cc1nnc(CNc2ncnc3ncc(-c4ccc(F)cc4)cc23)o1] | 6-(4-fluorophenyl)-N-[(5-methyl-1,3,4-oxadiazol-2-yl)methyl]pyrido[2,3-d]pyrimidin-4-amine |
| Example 75 | 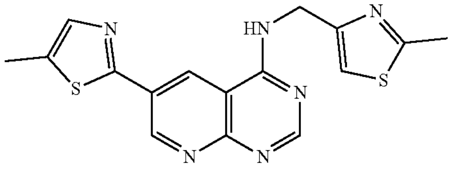 | 6-(5-methylthiazol-2-yl)-N-[(2-methylthiazol-4-yl)methyl]pyrido[2,3-d]pyrimidin-4-amine |
| Example 76 | 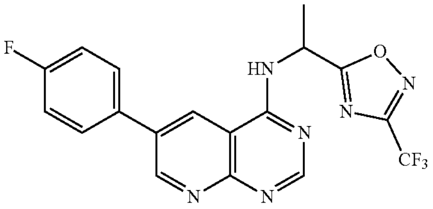 [SMILES: CC(Nc1ncnc2ncc(-c3ccc(F)cc3)cc12)c1nc(C(F)(F)F)no1] | 6-(4-fluorophenyl)-N-1-[3-(trifluoromethyl)-1,2,4-oxadiazol-5-yl]ethyl]pyrido[2,3-d]pyrimidin-4-amine |
| Example 77 | 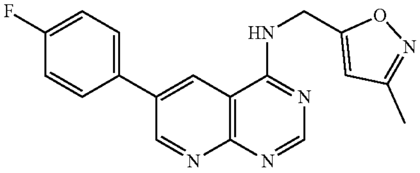 [SMILES: Cc1cc(CNc2ncnc3ncc(-c4ccc(F)cc4)cc23)on1] | 6-(4-fluorophenyl)-N-[(3-methylisoxazol-5-yl)methyl]pyrido[2,3-d]pyrimidin-4-amine |
| Example 78 | 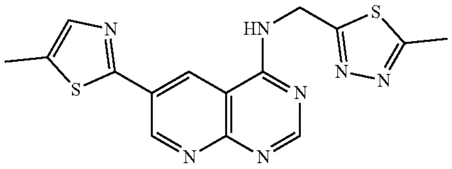 | N-[(5-methyl-1,3,4-thiadiazol-2-yl)methyl]-6-(5-methylthiazol-2-yl)pyrido[2,3-d]pyrimidin-4-amine |
| Example 79 | 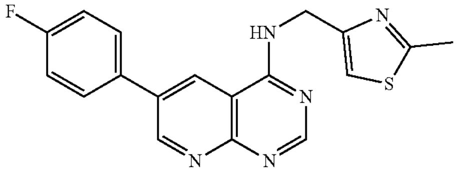 [SMILES: Cc1nc(CNc2ncnc3ncc(-c4ccc(F)cc4)cc23)cs1] | 6-(4-fluorophenyl)-N-[(2-methylthiazol-4-yl)methyl]pyrido[2,3-d]pyrimidin-4-amine |

TABLE 2-continued

| List of preferred compounds having Formula (Ia) | | |
|---|---|---|
| Ex. No. | Structure | Chemical name |
| Example 80 | 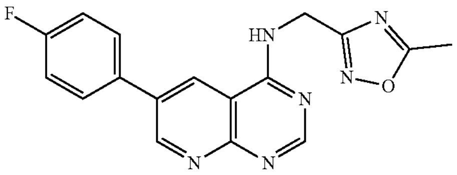 [SMILES: Cc1nc(CNc2ncnc3ncc(-c4ccc(F)cc4)cc23)no1] | 6-(4-fluorophenyl)-N-[(5-methyl-1,2,4-oxadiazol-3-yl)methyl]pyrido[2,3-d]pyrimidin-4-amine |
| Example 82 | 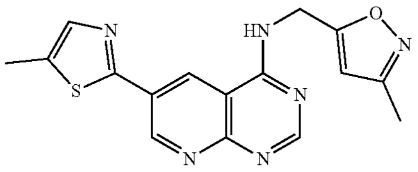 [SMILES: Cc1cc(CNc2ncnc3ncc(-c4ncc(C)s4)cc23)on1] | N-[(3-methylisoxazol-5-yl)methyl]-6-(5-methylthiazol-2-yl)pyrido[2,3-d]pyrimidin-4-amine |
| Example 83 | 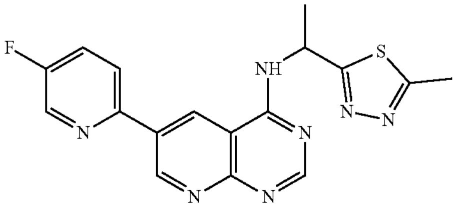 [SMILES: Cc1nnc(C(C)Nc2ncnc3ncc(-c4ccc(F)cn4)cc23)s1] | Single enantiomer 1 of 6-(5-fluoro-2-pyridyl)-N-[1-(5-methyl-1,3,4-thiadiazol-2-yl)ethyl]pyrido[2,3-d]pyrimidin-4-amine |
| Example 84 | 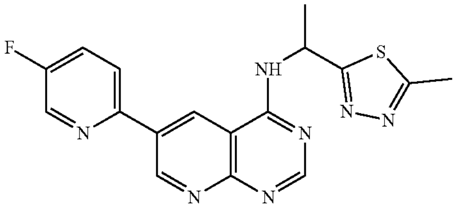 [SMILES: Cc1nnc(C(C)Nc2ncnc3ncc(-c4ccc(F)cn4)cc23)s1] | Single enantiomer 2 of 6-(5-fluoro-2-pyridyl)-N-[1-(5-methyl-1,3,4-thiadiazol-2-yl)ethyl]pyrido[2,3-d]pyrimidin-4-amine |
| Example 87 | 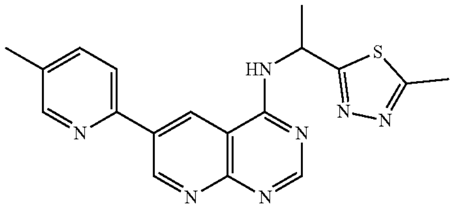 | Single enantiomer 1 of N-(1-(5-methyl-1,3,4-thiadiazol-2-yl)ethyl)-6-(5-methylpyridin-2-yl)pyrido[2,3-d]pyrimidin-4-amine |
| Example 88 | 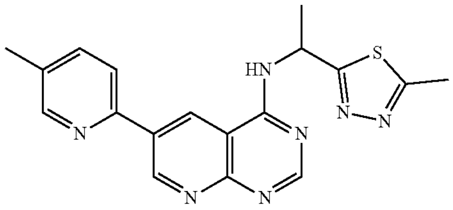 | Single enantiomer 2 of N-(1-(5-methyl-1,3,4-thiadiazol-2-yl)ethyl)-6-(5-methylpyridin-2-yl)pyrido[2,3-d]pyrimidin-4-amine |
| Example 91 | 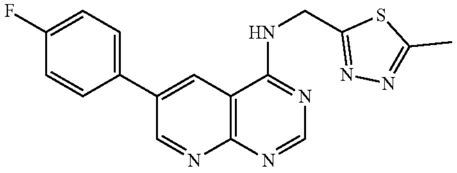 | 6-(4-Fluorophenyl)-N-[(5-methyl-1,3,4-thiadiazol-2-yl)methyl]pyrido[2,3-d]pyrimidin-4-amine |

TABLE 2-continued

| List of preferred compounds having Formula (Ia) | | |
|---|---|---|
| Ex. No. | Structure | Chemical name |
| Example 92 | 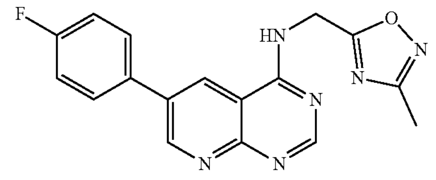 [SMILES: Cc1noc(CNc2ncnc3ncc(-c4ccc(F)cc4)cc23)n1] | 6-(4-fluorophenyl)-N-[(3-methyl-1,2,4-oxadiazol-5-yl)methyl]pyrido[2,3-d]pyrimidin-4-amine |
| Example 93 | 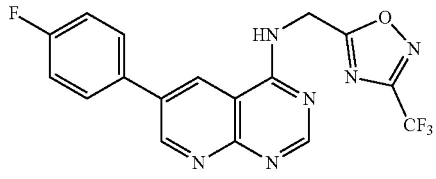 [SMILES: Fc1ccc(-c2cnc3ncnc(NCc4nc(C(F)(F)F)no4)c3c2)cc1] | 6-(4-fluorophenyl)-N-[[3-(trifluoromethyl)-1,2,4-oxadiazol-5-yl]methyl]pyrido[2,3-d]pyrimidin-4-amine |
| Example 94 | 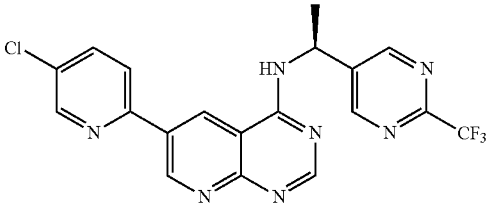 [SMILES: C[C@H](Nc1ncnc2ncc(-c3ccc(Cl)cn3)cc12)c1cnc(C(F)(F)F)nc1] | 6-(5-chloro-2-pyridyl)-N-[(1S)-1-[2-(trifluoromethyl)pyrimidin-5-yl]ethyl]pyrido[2,3-d]pyrimidin-4-amine |
| Example 95 | 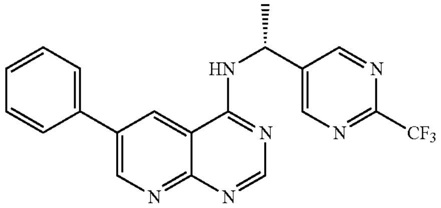 [SMILES: C[C@@H](Nc1ncnc2ncc(-c3ccccc3)cc12)c1cnc(C(F)(F)F)nc1] | 6-phenyl-N-[(1R)-1-[2-(trifluoromethyl)pyrimidin-5-yl]ethyl]pyrido[2,3-d]pyrimidin-4-amine |
| Example 102 | 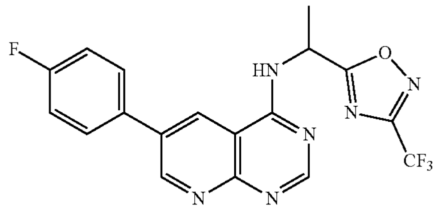 [SMILES: CC(Nc1ncnc2ncc(-c3ccc(F)cc3)cc12)c1nc(C(F)(F)F)no1] | Single enantiomer 1 of 6-(4-fluorophenyl)-N-[1-[3-(trifluoromethyl)-1,2,4-oxadiazol-5-yl]ethyl]pyrido[2,3-d]pyrimidin-4-amine |
| Example 103 | 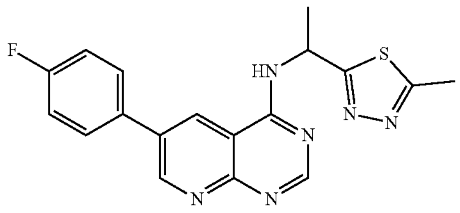 | Single enantiomer 1 of 6-(4-fluorophenyl)-N-(1-(5-methyl-1,3,4-thiadiazol-2-yl)ethyl)pyrido[2,3-d]pyrimidin-4-amine |
| Example 104 | 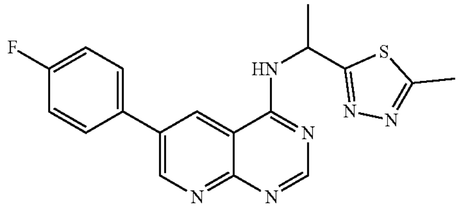 [SMILES: Cc1nnc(C(C)Nc2ncnc3ncc(-c4ccc(F)cc4)cc23)s1] | Single enantiomer 2 of 6-(4-fluorophenyl)-N-(1-(5-methyl-1,3,4-thiadiazol-2-yl)ethyl)pyrido[2,3-d]pyrimidin-4-amine |

TABLE 2-continued

| List of preferred compounds having Formula (Ia) | | |
|---|---|---|
| Ex. No. | Structure | Chemical name |
| Example 105 | 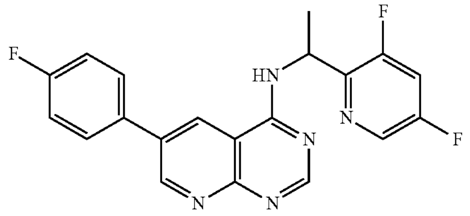 [SMILES: CC(Nc1ncnc2ncc(-c3ccc(F)cc3)cc12)c1ncc(F)cc1F] | Single enantiomer 1 of N-[1-(3,5-difluoro-2-pyridyl)ethyl]-6-(4-fluorophenyl)pyrido[2,3-d]pyrimidin-4-amine |
| Example 106 | 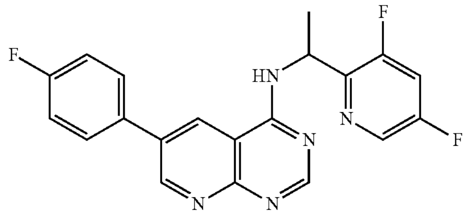 [SMILES: CC(Nc1ncnc2ncc(-c3ccc(F)cc3)cc12)c1ncc(F)cc1F] | Single enantiomer 2 of N-[1-(3,5-difluoro-2-pyridyl)ethyl]-6-(4-fluorophenyl)pyrido[2,3-d]pyrimidin-4-amine |
| Example 63a | 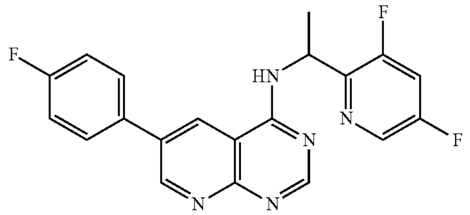 [SMILES: CC(Nc1ncnc2ncc(-c3ccc(F)cc3)cc12)c1ncc(F)cc1F] | N-[1-(3,5-difluoro-2-pyridyl)ethyl]-6-(4-fluorophenyl)pyrido[2,3-d]pyrimidin-4-amine |
| Example 107 | 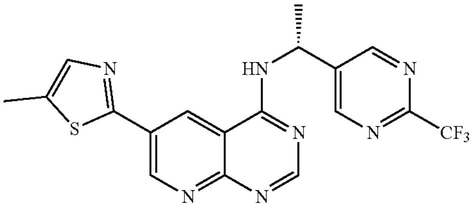 [SMILES: Cc1cnc(-c2cnc3ncnc(N[C@H](C)c4cnc(C(F)(F)F)nc4)c3c2)s1] | 6-(5-methylthiazol-2-yl)-N-[(1R)-1-[2-(trifluoromethyl)pyrimidin-5-yl]ethyl]pyrido[2,3-d]pyrimidin-4-amine |

In a still preferred embodiment, the invention refers to compound of formula (Ia) wherein Z is selected from the group consisting of heteroaryl, aryl, wherein any of such heteroaryl and aryl may be optionally substituted by one or more groups selected from $(C_1-C_3)$alkyl, halo;

R1 is H;

R2 is selected from the group consisting of heteroaryl $(C_1-C_4)$alkyl, wherein any of such alkyl, heteroaryl may be optionally substituted by one or more groups selected from $(C_1-C_3)$alkyl, halo, $(C_1-C_6)$ haloalkyl, -oxo;

J is H.

According to preferred embodiments, the invention refers to at least one of the compounds listed in the table 3 below and pharmaceutical acceptable salts thereof.

TABLE 3

| List of preferred compounds having Formula (Ia) | | |
|---|---|---|
| Ex. No. | Structure | Chemical name |
| Example 1 | 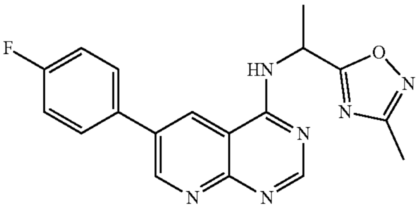 [SMILES: Cc1noc(C(C)Nc2ncnc3ncc(-c4ccc(F)cc4)cc23)n1] | 6-(4-Fluorophenyl)-N-[1-(3-methyl-1,2,4-oxadiazol-5-yl)ethyl]pyrido[2,3-d]pyrimidin-4-amine |

TABLE 3-continued

| List of preferred compounds having Formula (Ia) | | |
|---|---|---|
| Ex. No. | Structure | Chemical name |
| Example 2 | 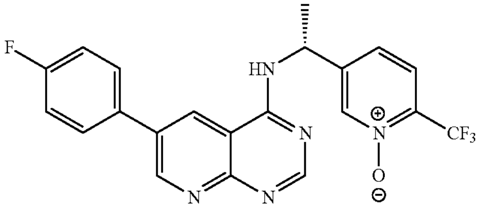 [SMILES: C[C@@H](Nc1ncnc2ncc(-c3ccc(F)cc3)cc12)c1ccc(C(F)(F)F)[n+]([O-])c1] | (R)-5-(1-((6-(4-fluorophenyl)pyrido[2,3-d]pyrimidin-4-yl)amino)ethyl)-2-(trifluoromethyl)pyridine 1-oxide |
| Example 6 | 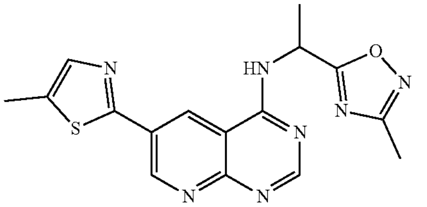 [SMILES: Cc1noc(C(C)Nc2ncnc3ncc(-c4ncc(C)s4)cc23)n1] | N-(1-(3-Methyl-1,2,4-oxadiazol-5-yl)ethyl)-6-(5-methylthiazol-2-yl)pyrido[2,3-d]-pyrimidin-4-amine |
| Example 7 | 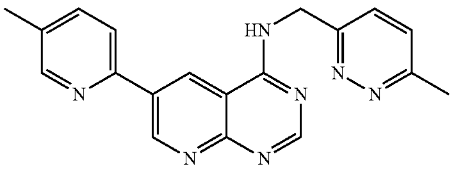 | N-((6-Methylpyridazin-3-yl)methyl)-6-(5-methylpyridin-2-yl)pyrido[2,3-d]pyrimidin-4-amine |
| Example 9 | 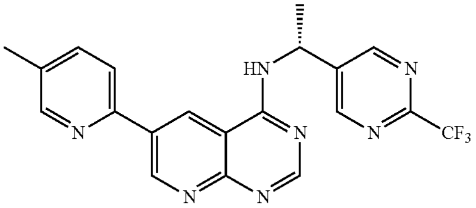 [SMILES: Cc1ccc(-c2cnc3ncnc(N[C@H](C)c4cnc(C(F)(F)F)nc4)c3c2)nc1] | (R)-6-(5-Methylpyridin-2-yl)-N-(1-(2-(trifluoromethyl)pyrimidin-5-yl)ethyl)pyrido[2,3-d]pyrimidin-4-amine |
| Example 10 | 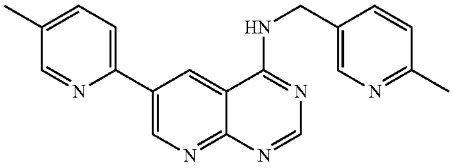 | 6-(5-methylpyridin-2-yl)-N-((6-methylpyridin-3-yl)methyl)pyrido[2,3-d]pyrimidin-4-amine |
| Example 11 | 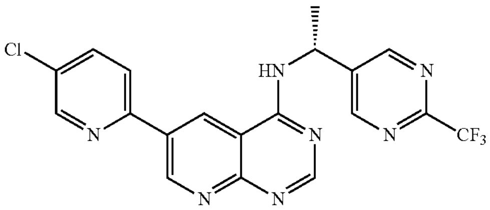 [SMILES: C[C@@H](Nc1ncnc2ncc(-c3ccc(Cl)cn3)cc12)c1cnc(C(F)(F)F)nc1] | (R)-6-(5-Chloropyridin-2-yl)-N-(1-(2-(trifluoromethyl)pyrimidin-5-yl)ethyl)pyrido[2,3-d]pyrimidin-4-amine |
| Example 13 | 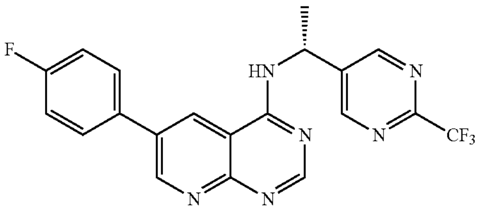 [SMILES: C[C@@H](Nc1ncnc2ncc(-c3ccc(F)cc3)cc12)c1cnc(C(F)(F)F)nc1] | (R)-6-(4-Fluorophenyl)-N-(1-(2-(trifluoromethyl)pyrimidin-5-yl)ethyl)pyrido[2,3-d]pyrimidin-4-amine |

TABLE 3-continued

| List of preferred compounds having Formula (Ia) | | |
|---|---|---|
| Ex. No. | Structure | Chemical name |
| Example 14 | 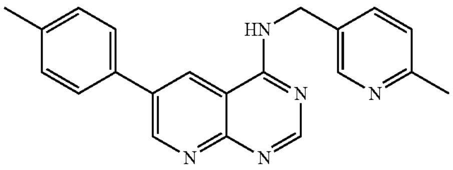 | N-((6-methylpyridin-3-yl)methyl)-6-(p-tolyl)pyrido[2,3-d]pyrimidin-4-amine |
| Example 15 | 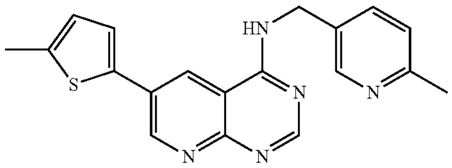 | N-((6-methylpyridin-3-yl)methyl)-6-(5-methylthiophen-2-yl)pyrido[2,3-d]pyrimidin-4-amine |
| Example 16 | 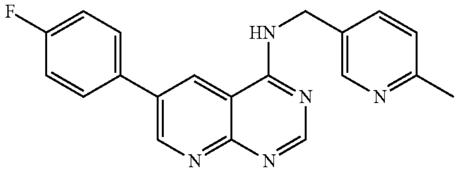 [SMILES: Cc1ccc(CNc2ncnc3ncc(-c4ccc(F)cc4)cc23)cn1] | 6-(4-fluorophenyl)-N-((6-methylpyridin-3-yl)methyl)pyrido[2,3-d]pyrimidin-4-amine |
| Example 19 | 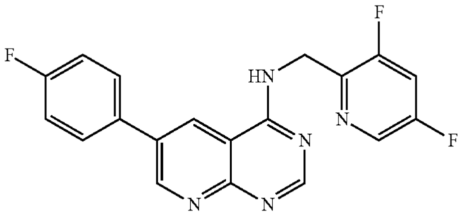 [SMILES: Fc1ccc(-c2cnc3ncnc(NCc4ncc(F)cc4F)c3c2)cc1] | N-((3,5-difluoropyridin-2-yl)methyl)-6-(4-fluorophenyl)pyrido[2,3-d]pyrimidin-4-amine |
| Example 20 | 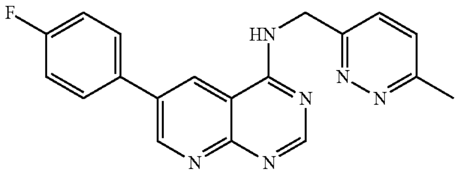 [SMILES: Cc1ccc(CNc2ncnc3ncc(-c4ccc(F)cc4)cc23)nn1] | 6-(4-fluorophenyl)-N-((6-methylpyridazin-3-yl)methyl)pyrido[2,3-d]pyrimidin-4-amine |
| Example 43 | 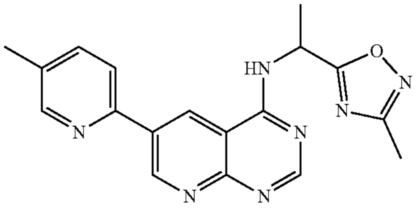 [SMILES: Cc1ccc(-c2cnc3ncnc(NC(C)c4nc(C)no4)c3c2)nc1] | Single enantiomer 1 of N-(1-(3-Methyl-1,2,4-oxadiazol-5-yl)ethyl)-6-(5-methylpyridin-2-yl)pyrido[2,3-d]pyrimidin-4-amine |
| Example 44 | 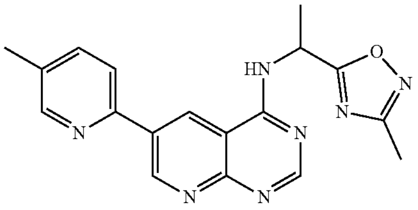 [SMILES: Cc1ccc(-c2cnc3ncnc(NC(C)c4nc(C)no4)c3c2)nc1] | Single enantiomer 2 of N-(1-(3-Methyl-1,2,4-oxadiazol-5-yl)ethyl)-6-(5-methylpyridin-2-yl)pyrido[2,3-d]pyrimidin-4-amine |

TABLE 3-continued

| List of preferred compounds having Formula (Ia) | | |
|---|---|---|
| Ex. No. | Structure | Chemical name |
| Example 45 | 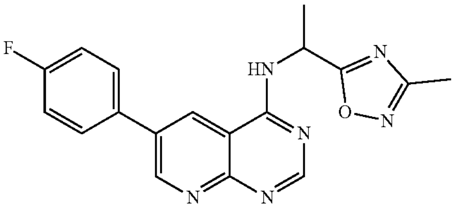 [SMILES: Cc1noc(C(C)Nc2ncnc3ncc(-c4ccc(F)cc4)cc23)n1] | Single enantiomer 1 of 6-(4-fluorophenyl)-N-[1-(3-methyl-1,2,4-oxadiazol-5-yl)ethyl]pyrido[2,3-d]pyrimidin-4-amine |
| Example 46 | 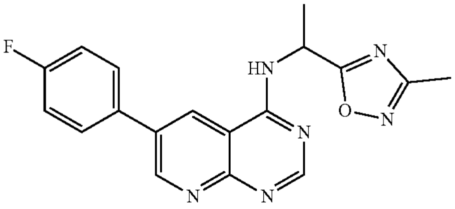 [SMILES: Cc1noc(C(C)Nc2ncnc3ncc(-c4ccc(F)cc4)cc23)n1] | Single enantiomer 2 of 6-(4-fluorophenyl)-N-[1-(3-methyl-1,2,4-oxadiazol-5-yl)ethyl]pyrido[2,3-d]pyrimidin-4-amine |
| Example 47 | 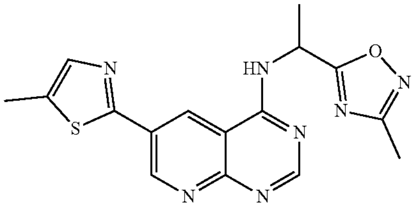 [SMILES: Cc1noc(C(C)Nc2ncnc3ncc(-c4ncc(C)s4)cc23)n1] | Single enantiomer 1 of N-(1-(3-methyl-1,2,4-oxadiazol-5-yl)ethyl)-6-(5-methylthiazol-2-yl)pyrido[2,3-d]pyrimidin-4-amine |
| Example 48 | 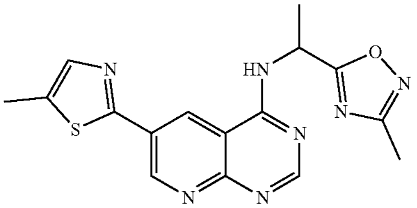 [SMILES: Cc1noc(C(C)Nc2ncnc3ncc(-c4ncc(C)s4)cc23)n1] | Single enantiomer 2 of N-(1-(3-methyl-1,2,4-oxadiazol-5-yl)ethyl)-6-(5-methylthiazol-2-yl)pyrido[2,3-d]pyrimidin-4-amine |

In a further preferred embodiment, the invention refers to compound of formula (Ia) wherein Z is selected from the group consisting of phenyl, pyridinyl and thienyl, wherein any of such phenyl, pyridinyl and thienyl may be optionally substituted by one or more groups selected from methyl and fluorine;

R1 is H;

R2 is selected from the group consisting of heteroaryl ($C_1$-$C_2$)alkyl, wherein any of such heteroaryl may be optionally substituted by one or more groups selected from methyl, fluorine and trifluoromethyl;

J is H.

According to preferred embodiments, the invention refers to at least one of the compounds listed in the table 4 below and pharmaceutical acceptable salts thereof.

TABLE 4

| List of further preferred compounds having Formula (Ia) | | |
|---|---|---|
| Ex. No. | Structure | Chemical name |
| Example 3 | 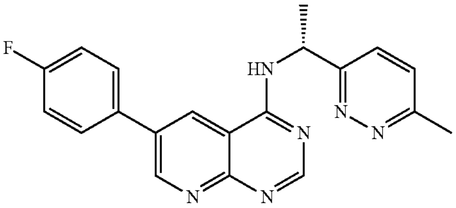 [SMILES: Cc1ccc([C@@H](C)Nc2ncnc3ncc(-c4ccc(F)cc4)cc23)nn1] | (R)-6-(4-fluorophenyl)-N-(1-(6-methylpyridazin-3-yl)ethyl)pyrido[2,3-d]pyrimidin-4-amine |

TABLE 4-continued

List of further preferred compounds having Formula (Ia)

| Ex. No. | Structure | Chemical name |
| --- | --- | --- |
| Example 7 | 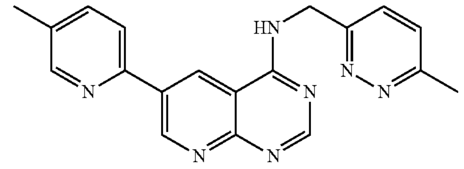 | N-((6-Methylpyridazin-3-yl)methyl)-6-(5-methylpyridin-2-yl)pyrido[2,3-d]pyrimidin-4-amine |
| Example 9 | 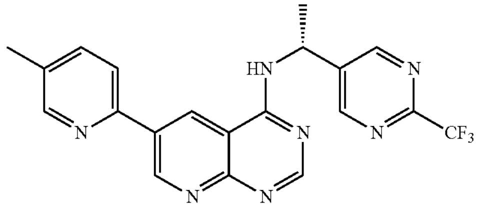 [SMILES: Cc1ccc(-c2cnc3ncnc(N[C@H](C)c4cnc(C(F)(F)F)nc4)c3c2)nc1] | (R)-6-(5-Methylpyridin-2-yl)-N-(1-(2-(trifluoromethyl)pyrimidin-5-yl)ethyl)pyrido[2,3-d]pyrimidin-4-amine |
| Example 11 | 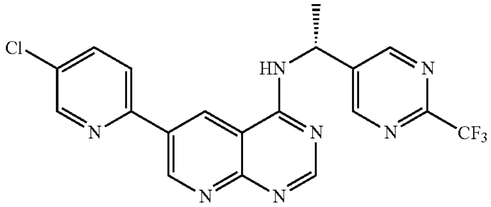 [SMILES: C[C@@H](Nc1ncnc2ncc(-c3ccc(Cl)cn3)cc12)c1cnc(C(F)(F)F)nc1] | (R)-6-(5-Chloropyridin-2-yl)-N-(1-(2-(trifluoromethyl)pyrimidin-5-yl)ethyl)pyrido[2,3-d]pyrimidin-4-amine |
| Example 13 | 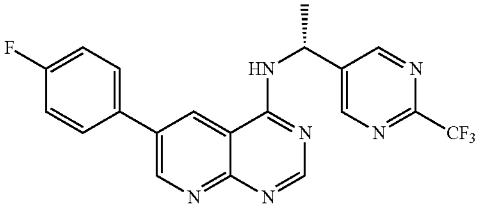 [SMILES: C[C@@H](Nc1ncnc2ncc(-c3ccc(F)cc3)cc12)c1cnc(C(F)(F)F)nc1] | (R)-6-(4-Fluorophenyl)-N-(1-(2-(trifluoromethyl)pyrimidin-5-yl)ethyl)pyrido[2,3-d]pyrimidin-4-amine |
| Example 14 | 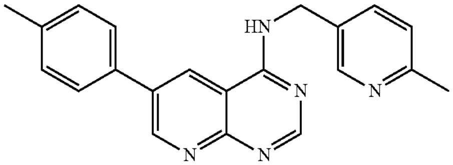 | N-((6-methylpyridin-3-yl)methyl)-6-(p-tolyl)pyrido[2,3-d]pyrimidin-4-amine |
| Example 15 | 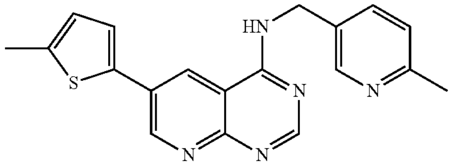 | N-((6-methylpyridin-3-yl)methyl)-6-(5-methylthiophen-2-yl)pyrido[2,3-d]pyrimidin-4-amine |
| Example 19 | 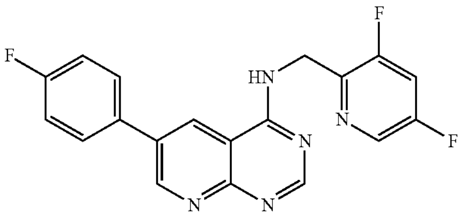 [SMILES: Fc1ccc(-c2cnc3ncnc(NCc4ncc(F)cc4F)c3c2)cc1] | N-((3,5-difluoropyridin-2-yl)methyl)-6-(4-fluorophenyl)pyrido[2,3-d]pyrimidin-4-amine |

TABLE 4-continued

| List of further preferred compounds having Formula (Ia) | | |
|---|---|---|
| Ex. No. | Structure | Chemical name |
| Example 45 | 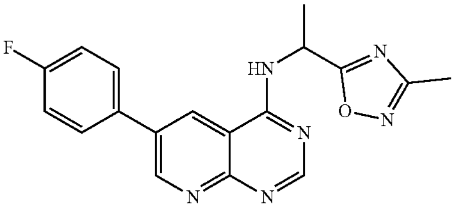 [SMILES: Cc1noc(C(C)Nc2ncnc3ncc(-c4ccc(F)cc4)cc23)n1] | Single enantiomer 1 of 6-(4-fluorophenyl)-N-[1-(3-methyl-1,2,4-oxadiazol-5-yl)ethyl]pyrido[2,3-d]pyrimidin-4-amine |
| Example 46 | 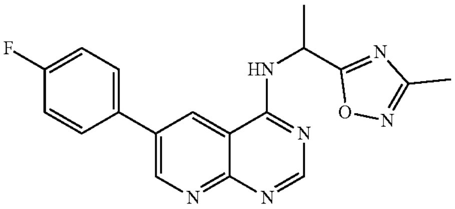 [SMILES: Cc1noc(C(C)Nc2ncnc3ncc(-c4ccc(F)cc4)cc23)n1] | Single enantiomer 2 of 6-(4-fluorophenyl)-N-[1-(3-methyl-1,2,4-oxadiazol-5-yl)ethyl]pyrido[2,3-d]pyrimidin-4-amine |

In a still preferred embodiment, the invention is directed to compounds of formula (I) as defined above, wherein $X_1$ is CH, represented by the formula Ib (Ib)

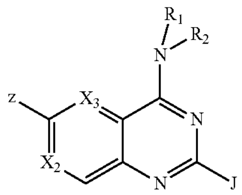

wherein $X_2$ and $X_3$ are independently CH or N,

Z is selected from the group consisting of heteroaryl and aryl wherein any of such aryl and heteroaryl may be optionally substituted by one or more groups selected from ($C_1$-$C_3$)alkyl, halo;

$R^1$ is H;

$R_2$ is selected from the group consisting of heteroaryl ($C_1$-$C_4$)alkyl-, wherein any of such alkyl and heteroaryl may be optionally substituted by one or more groups selected from ($C_1$-$C_3$)alkyl, ($C_1$-$C_6$) haloalkyl;

J is H.

In a further preferred embodiment, the invention refers to compound of formula Ib wherein $X_2$ and $X_3$ are independently CH or N, Z is selected from the group consisting of heteroaryl, which is pyridinyl, thiazolyl, each of said heteroaryl is further optionally substituted by one or more methyl, aryl which is phenyl, each of said aryl is further optionally substituted by one or more fluorine;

R1 is H;

R2 is selected from the group consisting of heteroaryl($C_1$-$C_4$)alkyl-, which is (pyrimidyl)ethyl, (pyridazyl)methyl, (oxadiazolyl)ethyl, each of said heteroarylalkyl is further optionally substituted by one or more groups selected from methyl and trifluoromethyl;

J is H.

According to preferred embodiments, the invention refers to at least one compounds listed in the table 5 below and pharmaceutical acceptable salts thereof.

TABLE 5

| List of preferred compounds having Formula (Ib) | | |
|---|---|---|
| Ex. No. | Structure | Chemical Name |
| Example 26 | 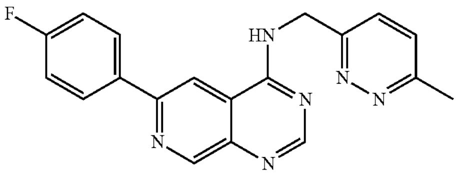 [SMILES: Cc1ccc(CNc2ncnc3cnc(-c4ccc(F)cc4)cc23)nn1] | 6-(4-Fluorophenyl)-N-((6-methylpyridazin-3-yl)methyl)pyrido[3,4-d]pyrimidin-4-amine |

TABLE 5-continued

| List of preferred compounds having Formula (Ib) | | |
|---|---|---|
| Ex. No. | Structure | Chemical Name |
| Example 27 | 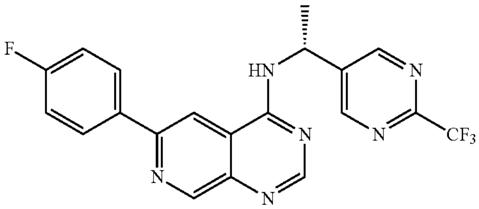 [SMILES: C[C@@H](Nc1ncnc2cnc(-c3ccc(F)cc3)cc12)c1cnc(C(F)(F)F)nc1] | 6-(4-Fluorophenyl)-N-[(1R)-1-[2-(trifluoromethyl)pyrimidn-5-yl]ethyl]pyrido[3,4-d]pyrimidin-4-amine |
| Example 28 | 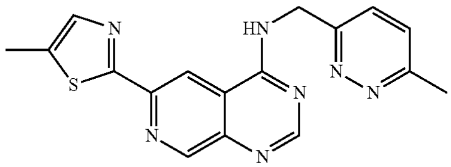 | N-[(6-Methylpyridazin-3-yl)methyl]-6-(5-methylthiazol-2-yl)pyrido[3,4-d]pyrimidin-4-amine |
| Example 29 | 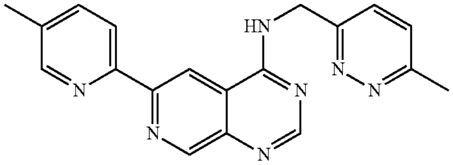 | N-[(6-methylpyridazin-3-yl)methyl]-6-(5-methyl-2-pyridyl)pyrido[3,4-d]pyrimidin-4-amine |
| Example 30 | 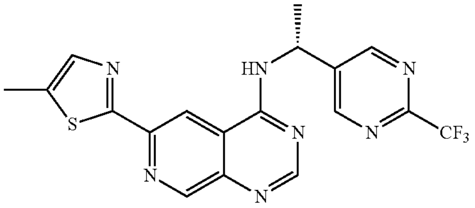 [SMILES: Cc1cnc(-c2cc3c(N[C@H](C)c4cnc(C(F)(F)F)nc4)ncnc3cn2)s1] | 6-(5-methylthiazol-2-yl)-N-[(1R)-1-[2-(trifluoromethyl)pyrimidin-5-yl]ethyl]pyrido[3,4-d]pyrimidin-4-amine |
| Example 31 | 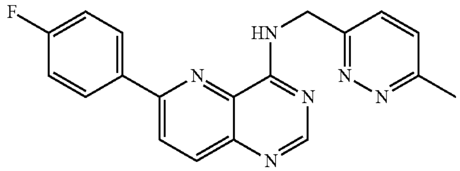 [SMILES: Cc1ccc(CNc2ncnc3ccc(-c4ccc(F)cc4)nc23)nn1] | 6-(4-Fluorophenyl)-N-((6-methylpyridazin-3-yl)methyl)pyrido[3,2-d]pyrimidin-4-amine |
| Example 32 | 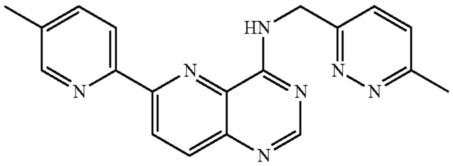 | N-((6-methylpyridazin-3-yl)methyl)-6-(5-methylpyridin-2-yl)pyrido[3,2-d]-pyrimidin-4-amine |
| Example 33 | 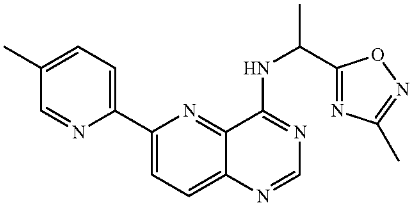 [SMILES: Cc1ccc(-c2ccc3ncnc(NC(C)c4nc(C)no4)c3n2)nc1] | N-(1-(3-methyl-1,2,4-oxadiazol-5-yl)ethyl)-6-(5-methylpyridin-2-yl)pyrido[3,2-d]pyrimidin-4-amine |
| Example 34 | 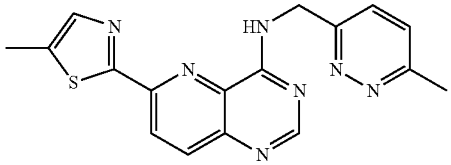 | N-[(6-methylpyridazin-3-yl)methyl]-6-(5-methylthiazol-2-yl)pyrido[3,2-d]pyrimidin-4-amine |

TABLE 5-continued

| List of preferred compounds having Formula (Ib) | | |
|---|---|---|
| Ex. No. | Structure | Chemical Name |
| Example 35 | 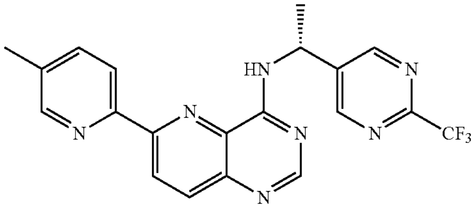 [SMILES: Cc1ccc(-c2ccc3ncnc(N[C@H](C)c4cnc(C(F)(F)F)nc4)c3n2)nc1] | (R)-6-(5-Methylpyridin-2-yl)-N-(1-(2-(trifluoromethyl)pyrimidin-5-yl)ethyl)pyrido[3,2-d]pyrimidin-4-amine |
| Example 36 | 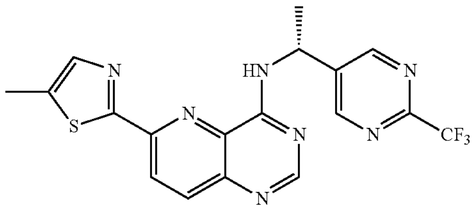 [SMILES: Cc1cnc(-c2ccc3ncnc(N[C@H](C)c4cnc(C(F)(F)F)nc4)c3n2)s1] | (R)-6-(5-methylthiazol-2-yl)-N-(1-(2-(trifluoromethyl)pyrimidin-5-yl)ethyl)-pyrido[3,2-d]pyrimidin-4-amine |
| Example 37 | 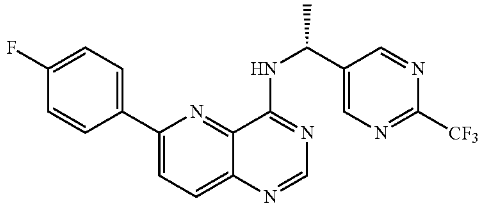 [SMILES: C[C@@H](Nc1ncnc2ccc(-c3ccc(F)cc3)nc12)c1cnc(C(F)(F)F)nc1] | (R)-6-(4-fluorophenyl)-N-(1-(2-(trifluoromethyl)pyrimidin-5-yl)ethyl)pyrido[3,2-d]pyrimidin-4-amine |
| Example 38 | 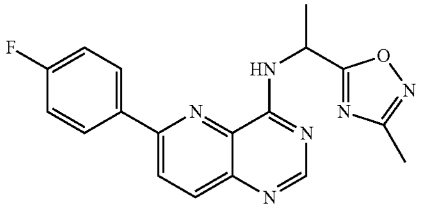 [SMILES: Cc1noc(C(C)Nc2ncnc3ccc(-c4ccc(F)cc4)nc23)n1] | 6-(4-Fluorophenyl)-N-(1-(3-methyl-1,2,4-oxadiazol-5-yl)ethyl)pyrido[3,2-d]pyrimidin-4-amine |

In a further preferred embodiment, the invention refers to compound of formula Ib wherein $X_2$ and $X_3$ are independently CH or N, Z is selected from the group consisting of pyridinyl, thiazolyl and phenyl, wherein each of said pyridinyl, thiazolyl and phenyl are optionally substituted by one or more groups selected from methyl and fluorine;

R1 is H;

R2 is selected from the group consisting of (pyrimidyl)ethyl and (pyridazyl)methyl, wherein each of said (pyrimidyl)ethyl and (pyridazyl)methyl are optionally substituted by one or more groups selected from methyl and trifluoromethyl;

J is H.

According to preferred embodiments, the invention refers to at least one compounds listed in the table 6 below and pharmaceutical acceptable salts thereof.

TABLE 6

| List of preferred compounds having Formula (Ib) | | |
|---|---|---|
| Ex. No. | Structure | Chemical name |
| Example 27 | 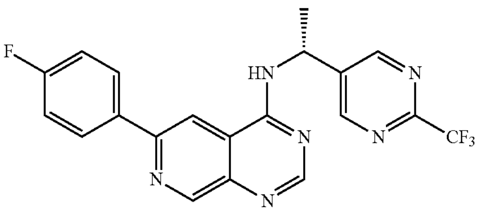 | 6-(4-Fluorophenyl)-N-[(1R)-1-[2-(trifluoromethyl)pyrimidin-5-yl]ethyl]pyrido[3,4-d]pyrimidin-4-amine |

TABLE 6-continued

| List of preferred compounds having Formula (Ib) | | |
|---|---|---|
| Ex. No. | Structure | Chemical name |
| Example 32 | 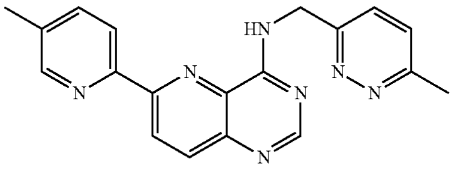 | N-((6-methylpyridazin-3-yl)methyl)-6-(5-methylpyridin-2-yl)pyrido[3,2-d]-pyrimidin-4-amine |
| Example 34 | 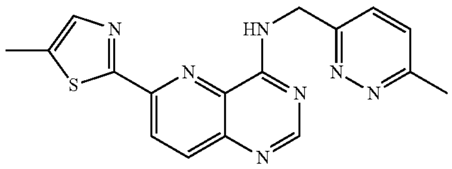 | N-[(6-methylpyridazin-3-yl)methyl]-6-(5-methylthiazol-2-yl)pyrido[3,2-d]pyrimidin-4-amine |

In a still preferred embodiment, the invention is directed to compounds of formula (I) as defined above, wherein $X_1$ and $X_3$ are N and $X_2$ is CH, represented by the formula Ic (Ic)

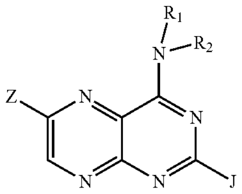

Z is selected from the group consisting of aryl and heteroaryl wherein any of such aryl and heteroaryl may be optionally substituted by one or more groups selected from halo and $(C_1-C_3)$alkyl;

$R_1$ is H;

$R_2$ is selected from the group consisting of heteroaryl$(C_1-C_4)$alkyl-, wherein any of such heteroaryl may be optionally substituted by one or more groups selected from $(C_1-C_3)$alkyl, $(C_1-C_6)$ haloalkyl;

J is H.

In a further preferred embodiment, the invention refers to compound of formula Ic wherein Z is aryl, preferably phenyl, each of said aryl is further optionally substituted by one or more fluorine;

R1 is H;

R2 is selected from the group consisting of heteroaryl$(C_1-C_4)$alkyl-, which is (pyridinyl)methyl, (pyridazyl)methyl, (oxadiazolyl)ethyl, (pyrimidinyl) ethyl, each of said heteroarylalkyl is further optionally substituted by one or more groups selected from methyl and trifluoromethyl;

J is H;

According to preferred embodiments, the invention refers to at least one compounds listed in the Table 7 below and pharmaceutical acceptable salts thereof.

TABLE 7

| List of preferred compounds having Formula (Ic) | | |
|---|---|---|
| Ex. No. | Structure | Chemica Name |
| Example 39 | 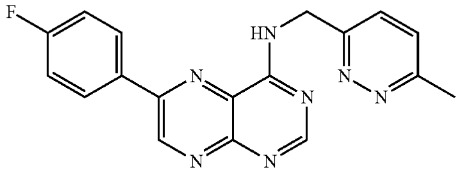 | 6-(4-Fluorophenyl)-N-((6-methylpyridazin-3-yl)methyl)pteridin-4-amine |
| Example 40 | 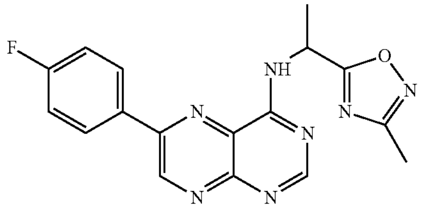 [SMILES: Cc1noc(C(C)Nc2ncnc3ncc(-c4ccc(F)cc4)nc23)n1] | 6-(4-Fluorophenyl)-N-(1-(3-methyl-1,2,4-oxadiazol-5-yl)ethyl)pteridin-4-amine |

TABLE 7-continued

| List of preferred compounds having Formula (Ic) | | |
|---|---|---|
| Ex. No. | Structure | Chemica Name |
| Example 41 | 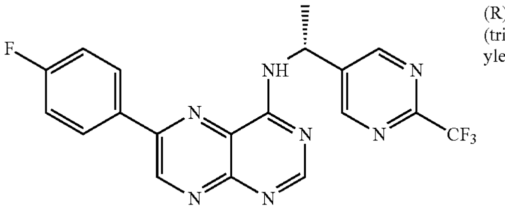 | (R)-6-(4-fluorophenyl)-N-(1-(2-(trifluoromethyl)pyrimidin-5-ylethyl)pteridin-4-amine |
| Example 42 | 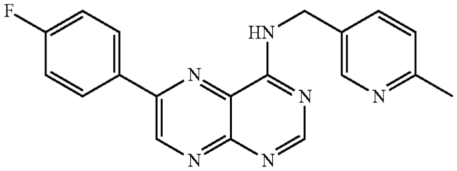 | 6-(4-Fluorophenyl)-N-((6-methylpyridin-3-yl)methyl)pteridin-4-amine |

The compounds of formula (I) including all the compounds here above listed can be generally prepared according to the procedure outlined in Schemes shown below using generally known methods.

Scheme 1

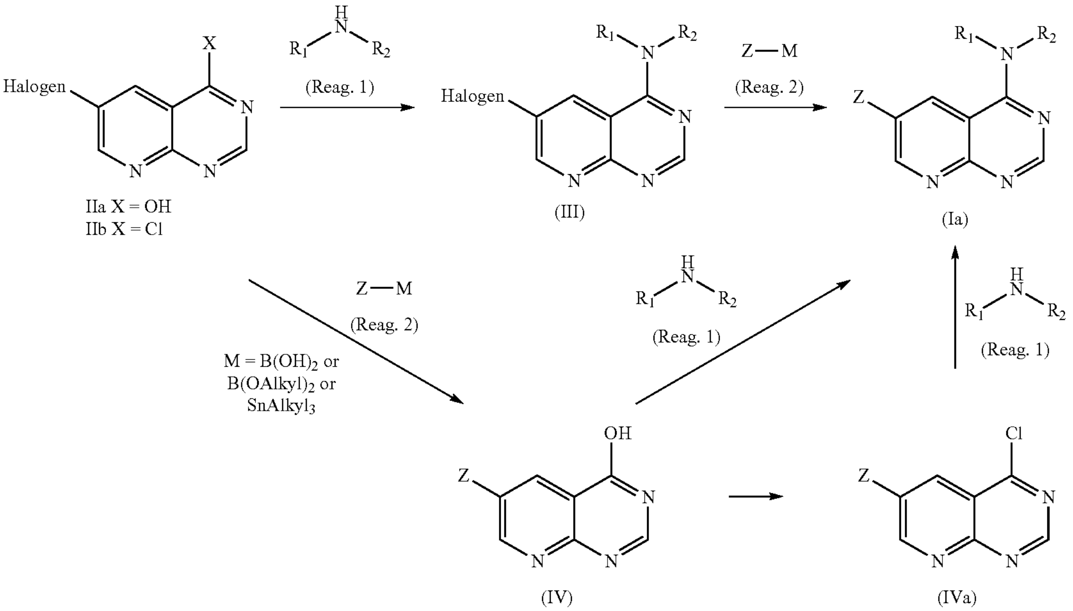

IIa X = OH
IIb X = Cl
(III)
(Ia)
(IV)
(IVa)

In one embodiment of the present invention, compound (Ia) may be prepared according to SCHEME 1 from intermediates (II).

Intermediates (III) may be prepared from intermediate (IIa) by deoxyamination reaction mediated by reagents like PyBOP or similar in the presence of a suitable amine (Reag. 1) or alternatively from intermediate (IIb) by reaction with a suitable amine (Reag. 1).

Compound (Ia) may be prepared from Intermediate (III) by a metal-catalyzed cross coupling reactions like Stille or Suzuki or similars with a suitable reagent (Reag. 2) like, for example, organoboron reagents.

In another embodiment of the present invention, intermediate (IV) may be prepared from intermediates (IIa) by a metal-catalyzed cross coupling reactions like Stille or Suzuki or similars with a suitable reagent (Reag. 2) like, for example, organoboron reagents.

Compound (Ia) may be prepared from Intermediate (IV) by deoxyamination reaction mediated by reagents like PyBOP or similar in the presence of a suitable amine (Reag. 1).

Intermediates (IVa) may be prepared from intermediate (IV) using a suitable chlorinating agent like, for example, phosphorus(V) oxychloride or thionyl chloride.

Compounds (Ia) may be prepared from intermediate (IVa) by an amination reaction with a suitable amine (Reag. 1) in the presence of a base like, for example, DIPEA.

Scheme 2

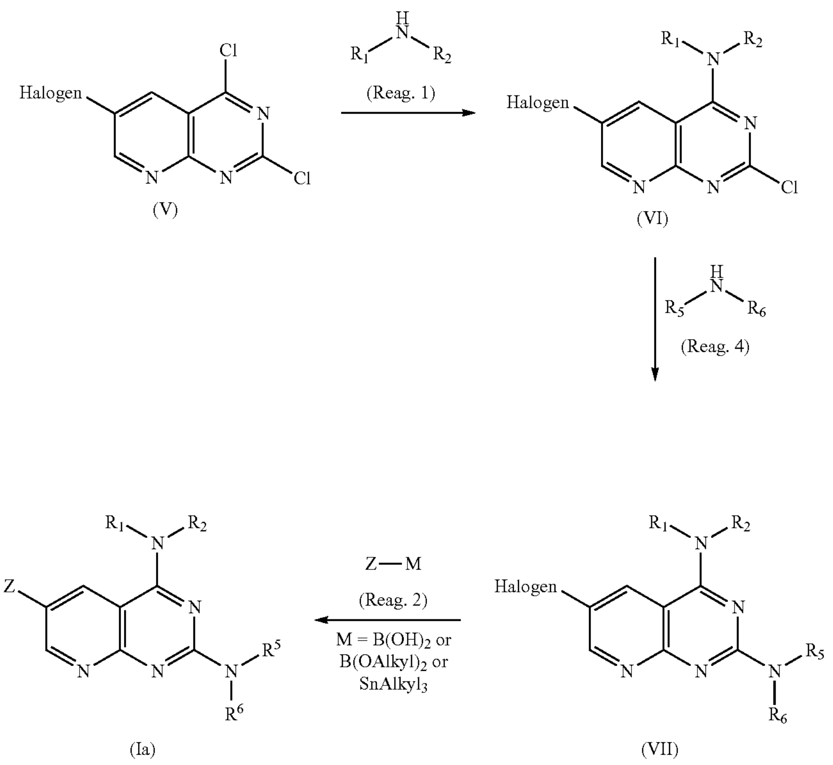

In another embodiment of the present invention, compound (Ia) may be prepared according to SCHEME 2 from intermediate (V).

Intermediate (VI) may be prepared from Intermediate (V) by an amination reaction with a suitable amine (Reag. 1) in the presence of a base like, for example, DIPEA.

Intermediate (VII) may be prepared from Intermediate (VI) by an amination reaction with a suitable amine (Reag. 4) in the presence of a base like, for example, DIPEA.

Compound (Ia) may be prepared from Intermediate (VII) by a metal-catalyzed cross coupling reactions like Stille or Suzuki or similars with a suitable reagent (Reag. 2) like, for example, organoboron reagents.

Scheme 3

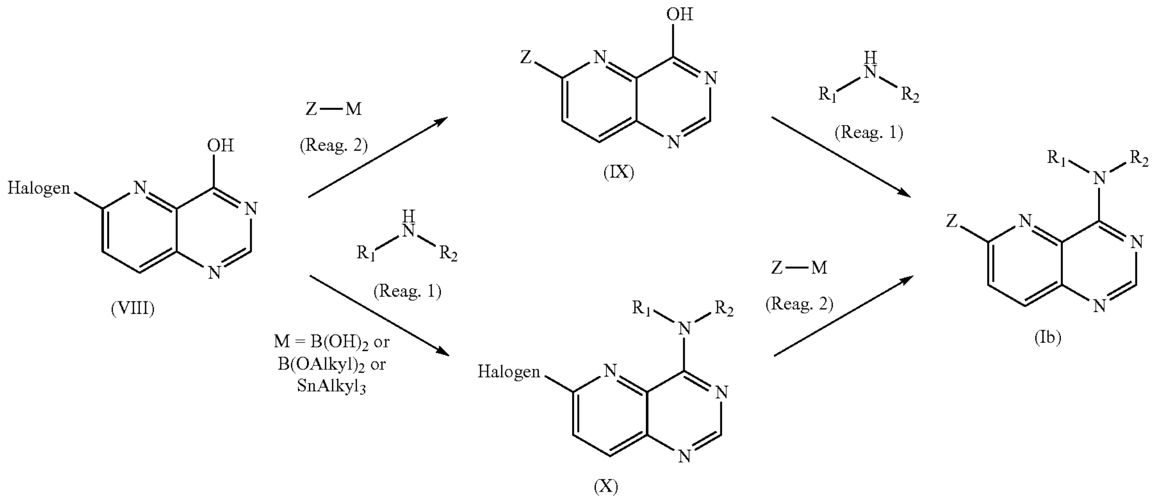

In an embodiment of the present invention, compound (Ib) may be prepared according to SCHEME 3 from intermediate (VIII).

Intermediate (IX) may be prepared from Intermediate (VIII) by a metal-catalyzed cross coupling reactions like Stille or Suzuki or similars with a suitable reagent (Reag. 2) like, for example, organoboron reagents.

Compounds (Ib) may be prepared from intermediate (IX) by deoxyamination reaction mediated by reagents like PyBOP or similar in the presence of a suitable amine (Reag. 1).

In another embodiment of the present invention, intermediate (X) may be prepared from intermediates (VIII) by deoxyamination reaction mediated by reagents like PyBOP or similar in the presence of a suitable amine (Reag. 1).

Compound (Ib) may be prepared from Intermediate (X) by by a metal-catalyzed cross coupling reactions like Stille or Suzuki or similars with a suitable reagent (Reag. 2) like, for example, organoboron reagents.

Scheme 4

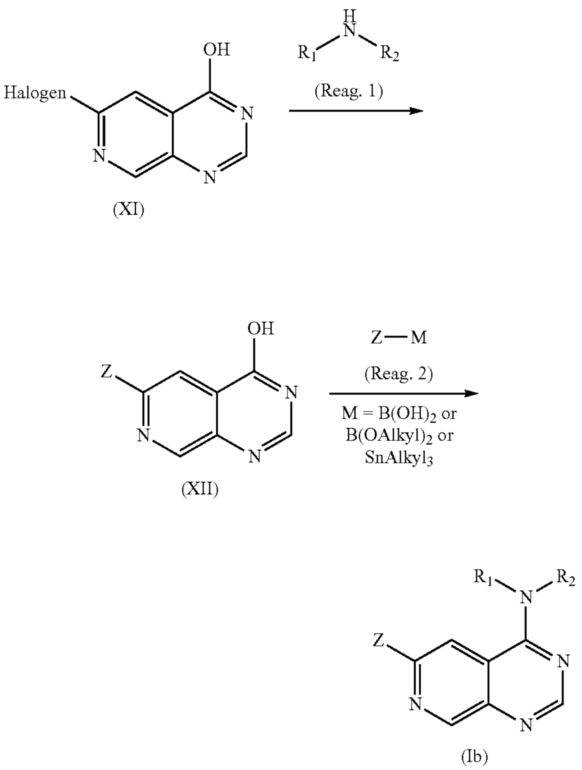

(XI)
(XII)
(Ib)

In an embodiment of the present invention, compound (Ib) may be prepared according to SCHEME 4 from intermediate (XI).

Intermediates (XII) may be prepared from intermediate (XI) by deoxyamination reaction mediated by reagents like PyBOP or similar in the presence of a suitable amine (Reag. 1).

Compound (Ib) may be prepared from Intermediate (XII) by a metal-catalyzed cross coupling reactions like Stille or Suzuki or similars with a suitable reagent (Reag. 2) like, for example, organoboron reagents.

Scheme 5

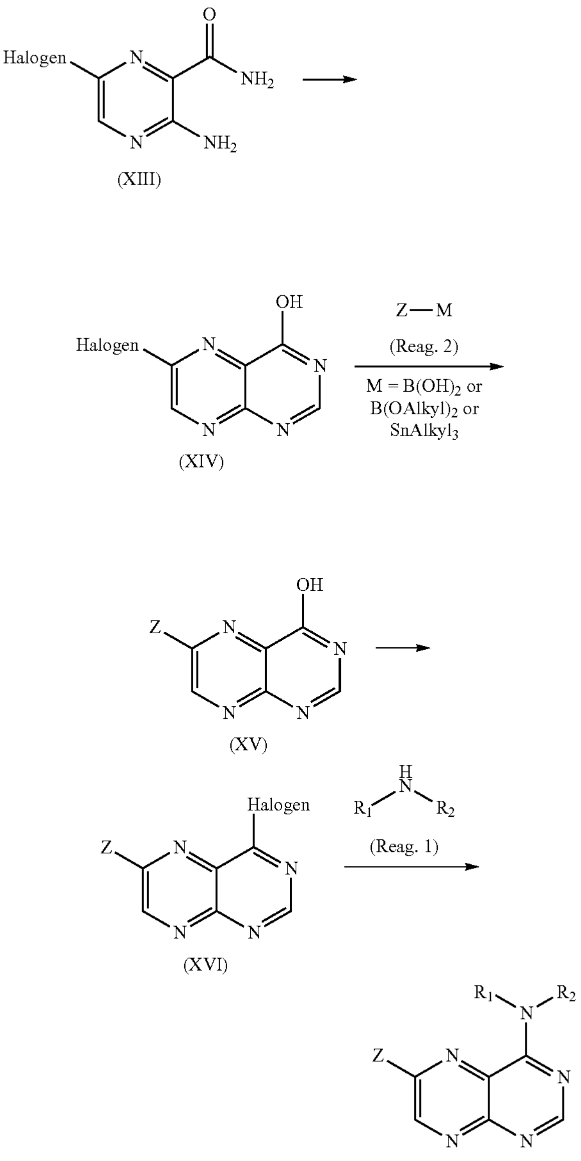

(XIII)
(XIV)
(XV)
(XVI)
(Ic)

In an embodiment of the present invention, compound (Ic) may be prepared according to SCHEME 5 from intermediate (XIII).

Intermediate (XIV) may be prepared from Intermediate (XIII) by means of a ring construction reaction mediated by suitable reagents like, for example, triethylorthoformate.

Intermediate (XV) may be prepared from Intermediate (XIV) by a metal-catalyzed cross coupling reactions like Stille or Suzuki or similars with a suitable reagent (Reag. 2) like, for example, organoboron reagents.

Intermediates (XVI) may be prepared from intermediate (XV) by deoxyhalogenation reaction mediated by reagents like thionyl chloride or similar.

Compounds (Ic) may be prepared from intermediate (XVI) by amination reaction with a suitable amine R1 in the presence of a base like, for example, DIPEA.

In a specific aspect the present invention relates to compounds of formula (IIIa)

(IIIa)

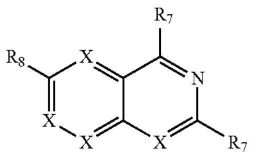

wherein X is N or CH, $R_7$ is OH and/or $C_1$;

$R_8$ is halo.

In a further aspect the present invention relates to the use of compounds of formula (IIIa) as intermediate in the preparation of compounds of formula (I) as above described.

The compounds of the present invention have surprisingly been found to effectively inhibit $P2X_3$ receptor and said compounds are useful for the treatment of respiratory disease.

In one embodiment, representative compounds of formula (I) of the present invention have surprisingly been found to effectively and selectively inhibit $P2X_3$ receptor and said compounds are useful for the treatment of respiratory disease avoiding adverse effect, such as loss of taste response.

The compound of formula (I) are selective $P2X_3$ antagonist wherein the selective $P2X_3$ antagonist is at least 10-fold selective for $P2X_3$ homomeric receptor antagonism versus $P2X_{2/3}$ heteromeric receptor antagonism.

In a preferred embodiment, the selective $P2X_3$ antagonist is at least 30-fold selective for $P2X_3$ homomeric receptor antagonism versus $P2X_{2/3}$ heteromeric receptor antagonism.

In a further preferred embodiment, the selective $P2X_3$ antagonist is at least 50-fold selective for $P2X_3$ homomeric receptor antagonism versus $P2X_{2/3}$ heteromeric receptor antagonism.

The present invention also provides a pharmaceutical composition comprising a compound of formula (I) or a pharmaceutically acceptable salt thereof in admixture with one or more pharmaceutically acceptable carrier or excipient, either alone or in combination with one or more further active ingredient.

In one aspect, the invention refers to a compound of formula (I) according to the invention for use as a medicament.

In a further aspect, the invention refers to the use of a compound of formula (I) of the invention, or a pharmaceutically acceptable salt thereof, in the manufacture of a medicament for the treatment of disorders associated with $P2X_3$ receptors mechanism, preferably for the treatment of respiratory diseases.

Preferably, the invention refers to a compound of formula (I) for use in the prevention and/or treatment of respiratory diseases, preferably cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm.

More preferably, the invention refers to a compounds of formula (I) for use in the prevention and/or treatment of chronic cough and cough associated with respiratory diseases such as COPD, asthma and bronchospasm.

The invention also refers to a method for the prevention and/or treatment of disorders associated with $P2X_3$ receptors mechanisms, said method comprising administering to a patient in need of such treatment a therapeutically effective amount of a compound of the invention.

In another embodiment, the disorder that can be treated by the compounds of the present invention is selected from the group consisting of cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm.

In a further preferred embodiment, the disorder is selected from cough and chronic cough.

The methods of treatment of the invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion) and by inhalation.

Preferably the compounds of the present invention are administered orally and by inhalation.

Various solid oral dosage forms can be used for administering compounds of the invention including such solid forms as tablets, gelcaps, capsules, caplets, granules, lozenges and bulk powders. The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the invention.

Preferably the compounds of the invention are administered in forms of tablets.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the invention may be injected, for example, intravenously, in the form of an isotonic sterile solution.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers.

Preferably, the compounds of the present invention are administered orally.

The compounds of the invention can be administered as the sole active agent or in combination with other pharmaceutical active ingredients.

The dosages of the compounds of the invention depend upon a variety of factors including among others the particular disease to be treated, the severity of the symptoms, the route of administration and the like.

The invention is also directed to a device comprising a pharmaceutical composition comprising a compound of Formula (I) according to the invention, in form of a single- or multi-dose dry powder inhaler or a metered dose inhaler.

The various aspects of the invention described in this application are illustrated by the following examples which are not meant to limit the invention in any way. following examples illustrate the invention.

The example testing experiments described herein serve to illustrate the present invention and the invention is not limited to the examples given.

Preparations of Intermediates and Examples

Chemical names were generated using the Dotmatics software. In some case generally accepted names of commercially available reagents were used in place of Dotmatics software generated names.

All reagents, for which the synthesis is not described in the experimental part, are either commercially available, or are known compounds or may be formed from known compounds by known methods by a person skilled in the art.

(R)-1-(2-(trifluoromethyl)pyrimidin-5-yl)ethanamine HCl, (R)-1-(6-methylpyridazin-3-yl)ethan-1-amine HCl were prepared accordingly to the procedure described in WO2016/091776.

Abbreviation—Meaning $Et_2O$: diethyl ether;
$Et_3N$: triethyl amine;
TEA: triethyl amine;
DCC: N,N'-Dicyclohexylcarbodiimide;
PyBOP: (benzotriazol-1-yloxy)tripyrrolidinophosphonium hexafluorophosphate;
DMF: dimethylformamide;
EtOAc: Ethyl acetate;
RT: room temperature;
THF: tetrahydrofuran;
DCM: dichloromethane;
MeOH: methyl alcohol;
EtOH: ethylic alcohol;
TFA: Trifluoroacetic acid;
LC-MS: Liquid Chromatography/Mass Spectrometry;
HPLC: high pressure liquid chromatography;
MPLC: medium pressure liquid chromatography;
SFC: Supercritical Fluid Chromatography;
dppf: 1,1'-Bis(diphenylphosphino) ferrocene;
DIEA or DIPEA: N,N-Diisopropylethylamine;
MeCN: Acetonitrile;
MTBE: tert-Butyl methyl ether;
TBDMSCl: tert-Butyl(chloro)dimethylsilane;
DMSO: Dimethylsulfoxide;
$Boc_2O$: di-tert-butyl dicarbonate;
UPLC: Ultra Performance Liquid Chromatography.

General Experimental Details and Methods

Analytical Methods

Liquid Chromatography-Mass Spectrometry

Method 1

UPLC-MS was performed on a Waters Acquity I-Class with Waters Diode Array Detector coupled to a Waters SQD2 single quadrapole mass spectrometer using an Waters HSS C18 column (1.8 μm, 100×2.1 mm) being initially held at 5% acetonitrile/water (with 0.1% formic acid in each mobile phase) for 1.2 minutes, followed by a linear gradient of 5-100% within 3.5 minutes and then held at 100% for 1.5 minutes (F=0.5 mL/min).

Method 2

UPLC-MS was performed on a Waters Acquity I-Class with Waters Diode Array Detector coupled to a Waters SQD2 single quadrapole mass spectrometer using an Waters BEH Shield RP18 column (1.7 μm, 100×2.1 mm) being initially held at 5% acetonitrile/water (with 10 mM ammonium bicarbonate in each mobile phase) for 1.2 minutes, followed by a linear gradient of 5-100% within 3.5 minutes and then held at 100% for 1.5 minutes (F=0.5 mL/min).

Method 3

UPLC-MS was performed on a Waters DAD+Waters SQD2, single quadrapole UPLC-MS spectrometer using an Acquity UPLC BEH Shield RP18 1.7 um 100×2.1 mm (Plus guard cartridge), maintained at temp column being initially held at 5% acetonitrile/water (with 10 mM ammonium bicarbonate in each mobile phase) for 0.4 minutes, followed by a linear gradient of 5-95% within 6.4 minutes and then held at 95% for 1.2 minutes (F=0.4 mL/min).

Method 4

UPLC-MS was performed on a Waters DAD+Waters SQD2, single quadrapole UPLC-MS spectrometer using an Acquity UPLC BEH Shield RP18 1.7 um 100×2.1 mm (Plus guard cartridge), maintained at temp column being initially held at 5% Acetonitrile (Far UV grade) with 0.1% (V/V) formic acid/Water (High purity via PureLab Option unit) with 0.1% formic acid for 0.4 minutes, followed by a linear gradient of 5-95% within 6.4 minutes and then held at 95% for 1.2 minutes (F=0.4 mL/min).

Method 4.1

Acquity UPLC—QDa Mass Spectrometer with a C18-reverse-phase column (50×2.1 mm Acquity CSH with 1.7 μm particle size) maintained at 40° C., elution with A: 95/5 water/acetonitrile+0.05% formic acid; B: 95/5 acetonitrile/water+0.05% formic acid.

Gradient:

| Time [min] | Flow [ml/min] | Mobile phase A [%] | Mobile phase B [%] |
|---|---|---|---|
| 0.0 | 1 | 99.0 | 1.0 |
| 1.50 | 1 | 0.1 | 99.9 |
| 1.90 | 1 | 0.1 | 99.9 |
| 2.00 | 1 | 99.0 | 1.0 |

Detection-MS, UV PDA

MS ionisation method-Electrospray (positive/negative ion).

Method 4.2

Acquity UPLC—QDa Mass Spectrometer with a C18-reverse-phase column (50×2.1 mm Acquity BEH with 1.7 μm particle size) maintained at 40° C., elution with A: 95/5 water/acetonitrile+0.05% conc. ammonia; B: 95/5 acetonitrile/water+0.05% conc. ammonia.

Gradient:

| Time [min] | Flow [ml/min] | Mobile phase A [%] | Mobile phase B [%] |
|---|---|---|---|
| 0.0 | 1 | 99.0 | 1.0 |
| 1.50 | 1 | 0.1 | 99.9 |
| 1.90 | 1 | 0.1 | 99.9 |
| 2.00 | 1 | 99.0 | 1.0 |

Detection-MS, UV PDA

MS Ionisation Method-Electrospray (Positive/Negative Ion)

NMR $^{1}$H Nuclear magnetic resonance (NMR) spectroscopy was carried out using a Bruker or Varian instruments operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector. The columns used for the preparative purification of the compounds were a Waters Sunfire OBD Phenomenex Luna Phenyl Hexyl or Waters Xbridge Phenyl at 10 μm 19×150 mm or Waters CSH Phenyl Hexyl, 19×150, 5 μm column. Appropriate focused gradients were selected based on acetonitrile and methanol solvent systems under either acidic or basic conditions. The modifiers used under acidic/basic conditions were formic acid or trifluoroacetic acid (0.1% V/V) and ammonium bicarbonate (10 mM) respectively. The purification was controlled by Waters Fractionlynx software through monitoring at 210-400 nm, and triggered a threshold collection value at 260 nm and, when using the Fractionlynx, the presence of target molecular ion as observed under API conditions. Collected fractions were analysed by LCMS (Waters Acquity systems with Waters SQD).

Chiral Supercritical Fluid Chromatography (SFC) Separation Protocol

The diastereomeric separation of compounds was achieved by Supercritical Fluid Chromatography (SFC) using a Waters Thar Prep100 preparative SFC system (P200 CO2 pump, 2545 modifier pump, 2998 UV/VIS detector, 2767 liquid handler with Stacked Injection Module). The Waters 2767 liquid handler acted as both auto-sampler and fraction collector. Appropriate isocratic methods were selected based on methanol, ethanol or isopropanol solvent systems under un-modified or basic conditions. The standard SFC method used was modifier, CO2, 100 mL/min, 120 Bar backpressure, 40° C. column temperature. The modifier used under basic conditions was diethylamine (0.1% V/V). The modifier used under acidic conditions was either formic acid (0.1% V/V) or trifluoroacetic acid (0.1% V/V). The SFC purification was controlled by Waters Fractionlynx software through monitoring at 210-400 nm and triggered at a threshold collection value, typically 260 nm. Collected fractions were analysed by SFC (Waters/Thar SFC systems with Waters SQD). The fractions that contained the desired product were concentrated by vacuum centrifugation.

Supercritical Fluid Chromatography—Mass Spectrometry Analytical Conditions Method 5

SFC-MS was performed on a Waters/Thar SFC systems with Waters SQD using a Lux Cellulose-3 column with a 15% methyl alcohol/CO2 (with 0.1% diethylamine) isocratic run at 5 mL/min, 120 Bar backpressure, 40° C. column temperature.

Method 6

SFC-MS was performed on a Waters/Thar SFC systems with Waters SQD using a Lux Cellulose-3 column with a 20% methyl alcohol/CO2 (with 0.1% diethylamine) isocratic run at 5 mL/min, 120 Bar backpressure, 40° C. column temperature.

Method 7

SFC-MS was performed on a Waters/Thar SFC systems with Waters SQD using a Lux Cellulose-4 column with a 55% ethyl alcohol/CO2 (with 0.1% diethylamine) isocratic run at 5 mL/min, 120 Bar backpressure, 40° C. column temperature.

Method 8

SFC-MS was performed on a Waters/Thar SFC systems with Waters SQD using a Lux Cellulose-4 column with a 20% iso-propyl alcohol/CO2 (with 0.1% diethylamine) isocratic run at 5 mL/min, 120 Bar backpressure, 40° C. column temperature.

Method 9

SFC-MS was performed on a Waters/Thar SFC systems with Waters SQD using a Lux Cellulose-4 column with a 30% iso-propyl alcohol/CO2 (with 0.1% diethylamine) isocratic run at 5 mL/min, 120 Bar backpressure, 40° C. column temperature.

Method 10

SFC-MS was performed on a Waters/Thar SFC systems with Waters SQD using a Lux Cellulose-4 column with a 50% iso-propyl alcohol/CO2 (with 0.1% diethylamine) isocratic run at 5 mL/min, 120 Bar backpressure, 40° C. column temperature.

Method 11

SFC-MS was performed on a Waters/Thar SFC systems with Waters SQD using a Lux Cellulose-4 column with a 25% methyl alcohol/CO2 (with 0.1% diethylamine) isocratic run at 5 mL/min, 120 Bar backpressure, 40° C. column temperature.

Method 12

SFC-MS was performed on a Waters/Thar SFC systems with Waters SQD using a YMC Amylose-C column with a 15% ethyl alcohol/CO2 (with 0.1% diethylamine) isocratic run at 5 mL/min, 120 Bar backpressure, 40° C. column temperature.

Method 13

SFC-MS was performed on a Waters/Thar SFC systems with Waters SQD using a YMC Amylose-C column with a 25% iso-propyl alcohol/CO2 (with 0.1% diethylamine) isocratic run at 5 mL/min, 120 Bar backpressure, 40° C. column temperature.

Method 14

SFC-MS was performed on a Waters/Thar SFC systems with Waters SQD using a YMC Amylose-C column with a 35% iso-propyl alcohol/CO2 (with 0.1% diethylamine) isocratic run at 5 mL/min, 120 Bar backpressure, 40° C. column temperature.

Method 15

SFC-MS was performed on a Waters/Thar SFC systems with Waters SQD using a YMC Amylose-C column with a 55% iso-propyl alcohol/CO2 (with 0.1% diethylamine) isocratic run at 5 mL/min, 120 Bar backpressure, 40° C. column temperature.

Method 16

SFC-MS was performed on a Waters/Thar SFC systems with Waters SQD using a YMC Amylose-C column with a 15% methyl alcohol/CO2 (with 0.1% diethylamine) isocratic run at 5 mL/min, 120 Bar backpressure, 40° C. column temperature.

Method 17

SFC-MS was performed on a Waters/Thar SFC systems with Waters SQD using a YMC Amylose-C column with a 20% methyl alcohol/CO2 (with 0.1% diethylamine) isocratic run at 5 mL/min, 120 Bar backpressure, 40° C. column temperature.

Method 18

SFC-MS was performed on a Waters/Thar SFC systems with Waters SQD using a YMC Cellulose-C column with a 15% iso-propyl alcohol/CO2 (with 0.1% diethylamine) isocratic run at 5 mL/min, 120 Bar backpressure, 40° C. column temperature.

Method 19

SFC-MS was performed on a Waters/Thar SFC systems with Waters SQD using a YMC Cellulose-C column with a 15% methyl alcohol/CO2 (with 0.1% diethylamine) isocratic run at 5 mL/min, 120 Bar backpressure, 40° C. column temperature.

Method 20

SFC-MS was performed on a Waters/Thar SFC systems with Waters SQD using a YMC Cellulose-C column with a 25% methyl alcohol/CO2 (with 0.1% diethylamine) isocratic run at 5 mL/min, 120 Bar backpressure, 40° C. column temperature.

Method 21

SFC-MS was performed on a Waters/Thar SFC systems with Waters SQD using a YMC Cellulose-SC column with a 55% iso-propyl alcohol/CO2 (with 0.1% diethylamine) isocratic run at 5 mL/min, 120 Bar backpressure, 40° C. column temperature.

Method 22

SFC-MS was performed on a Waters/Thar SFC systems with Waters SQD using a Lux Cellulose-3 column with a 10% methyl alcohol/CO2 (with 0.1% diethylamine) isocratic run at 5 mL/min, 120 Bar backpressure, 40° C. column temperature.

Method 23

SFC-MS was performed on a Waters/Thar SFC systems with Waters SQD using a Lux Cellulose-3 column with a 30% methyl alcohol/CO2 (with 0.1% diethylamine) isocratic run at 5 mL/min, 120 Bar backpressure, 40° C. column temperature.

Method 24

SFC-MS was performed on a Waters/Thar SFC systems with Waters SQD using a Lux Cellulose-4 column with a 20% methyl alcohol/CO2 (with 0.1% diethylamine) isocratic run at 5 mL/min, 120 Bar backpressure, 40° C. column temperature.

Method 25

SFC-MS was performed on a Waters/Thar SFC systems with Waters SQD using a Lux Cellulose-4 column with a 40% methyl alcohol/CO2 (with 0.1% diethylamine) isocratic run at 5 mL/min, 120 Bar backpressure, 40° C. column temperature.

Method 26

SFC-MS was performed on a Waters/Thar SFC systems with Waters SQD using a Lux Cellulose-4 column with a 55% methyl alcohol/CO2 (with 0.1% diethylamine) isocratic run at 5 mL/min, 120 Bar backpressure, 40° C. column temperature.

Method 27

SFC-MS was performed on a Waters/Thar SFC systems with Waters SQD using a Lux Cellulose-4 column with a 55% iso-propyl alcohol/CO2 (with 0.1% diethylamine) isocratic run at 5 mL/min, 120 Bar backpressure, 40° C. column temperature.

Method 28

SFC-MS was performed on a Waters/Thar SFC systems with Waters SQD using a YMC Amylose-C column with a 20% ethyl alcohol/CO2 (with 0.1% diethylamine) isocratic run at 5 mL/min, 120 Bar backpressure, 40° C. column temperature.

Method 29

SFC-MS was performed on a Waters/Thar SFC systems with Waters SQD using a YMC Amylose-C column with a 25% methyl alcohol/CO2 (with 0.1% diethylamine) isocratic run at 5 mL/min, 120 Bar backpressure, 40° C. column temperature.

Method 30

SFC-MS was performed on a Waters/Thar SFC systems with Waters SQD using a YMC Amylose-C column with a 55% methyl alcohol/CO2 (with 0.1% diethylamine) isocratic run at 5 mL/min, 120 Bar backpressure, 40° C. column temperature.

Method 31

SFC-MS was performed on a Waters/Thar SFC systems with Waters SQD using a YMC Amylose-C column with a 30% iso-propyl alcohol/CO2 (with 0.1% diethylamine) isocratic run at 5 mL/min, 120 Bar backpressure, 40° C. column temperature.

Method 32

SFC-MS was performed on a Waters/Thar SFC systems with Waters SQD using a YMC Cellulose-C column with a 40% iso-propyl alcohol/CO2 (with 0.1% diethylamine) isocratic run at 5 mL/min, 120 Bar backpressure, 40° C. column temperature.

Preparation of Intermediates and Examples

Intermediate 1

6-Bromopyrido[2,3-d]pyrimidin-4(3H)-one

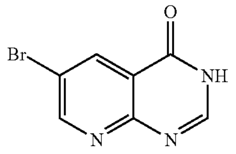 [SMILES: O=c1[nH]cnc2ncc(Br)cc12]

A mixture of 2-amino-5-bromonicotinic acid (35 g, 0.16 mol) and formamide (56 mL, 1.41 mol) was heated to 140° C. for 20 hours. The mixture was cooled to 40° C. and water (100 mL) was added. The mixture was stirred for 30 minutes before adding further water (300 mL). The reaction was filtered and the solid was washed with water (3×100 mL), a solution of 10% methanol in diethyl ether (3×100 mL) and diethyl ether (3×100 mL) to give the title compound (33.0 g, 90% yield) as a light brown solid.

$^1$H NMR (400 MHz, DMSO): δ 12.78-12.77 (m, 1H), 9.09 (d, J=2.5 Hz, 1H), 8.67 (d, J=2.5 Hz, 1H), 8.41 (s, 1H). LCMS (Method 4): [MH+]=226 at 2.38 min.

Intermediate 2

6-(4-Fluorophenyl)pyrido[2,3-d]pyrimidin-4(3H)-one

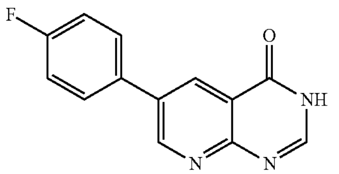 [SMILES: O=c1[nH]cnc2ncc(-c3ccc(F)cc3)cc12]

Nitrogen was bubbled for 5 min through a mixture of 6-bromopyrido[2,3-d]pyrimidin-4(3H)-one (Intermediate 1) (1.0 g, 4.42 mmol), 4-fluorophenylboronic acid (929 mg, 6.64 mmol) and cesium carbonate (4.32 g, 13.27 mmol) in N,N-dimethylformamide (10 mL) and water (2 mL) then tetrakis(triphenylphosphine)palladium(0) (664 mg, 0.57 mmol) was added. The resulting mixture was heated to 95° C. for 16 hours. After return to room temperature, the reaction was diluted with water (20 mL), filtered and the solid was washed with diethyl ether to give the title compound (965 mg, 90%) as a beige solid.

LCMS (Method 4): [MH+]=242 at 2.90 min.

The following compound was synthesised following the procedure described for the preparation of 6-(4-Fluorophenyl)pyrido[2,3-d]pyrimidin-4(3H)-one:

| Intermediate No. | Chemical Name Structure | Analytical data $^1$H NMR LC-MS |
|---|---|---|
| Intermediate 19 | 6-Phenylpyrido[2,3-d]pyrimidin-4(3H)-one 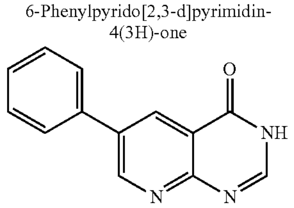 | LCMS (Method 4): [MH+] = 224 at 3.12 min. |

Example 1

6-(4-Fluorophenyl)-N-[1-(3-methyl-1,2,4-oxadiazol-5-yl)ethyl]pyrido[2,3-d]pyrimidin-4-amine

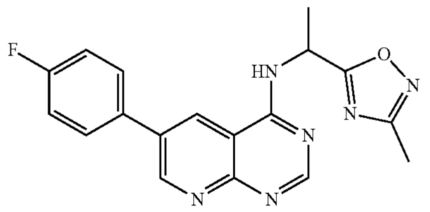 [SMILES: Cc1noc(C(C)Nc2ncnc3ncc(-c4ccc(F)cc4)cc23)n1]

To a solution of 6-(4-fluorophenyl)pyrido[2,3-d]pyrimidin-4(3H)-one (Intermediate 2) (516 mg, 2.14 mmol) in N,N-dimethylformamide (15 mL) was successively added (benzotriazol-1-yloxy)tripyrrolidinophosphonium hexafluorophosphate (1.17 g, 2.25 mmol) and di-isopropylethylamine (1.7 mL, 9.63 mmol). The resulting mixture was heated to 45° C. for 45 minutes then 1-(3-methyl-1,2,4-oxadiazol-5-yl)ethan-1-amine hydrochloride (600 mg, 3.0 mmol) was added and the heating was maintained at 45° C. for 16 hours. After return to room temperature, the mixture was diluted with ethyl acetate (25 mL) and water (70 mL). The organic phase was washed with brine (2×20 mL), passed through a hydrophobic frit and the solvent was removed in vacuo. The residue was purified by preparative HPLC to give the title compound as a white solid (190 mg, 25%).

$^1$H NMR (400 MHz, DMSO): δ 9.45 (d, J=2.3 Hz, 1H), 9.26-9.21 (m, 2H), 8.69 (s, 1H), 8.04-7.99 (m, 2H), 7.49 (dd, J=8.8, 8.8 Hz, 2H), 5.88 (d, J=6.8 Hz, 1H), 2.38 (s, 3H), 1.81 (d, J=7.1 Hz, 3H). LCMS (Method 3): [MH+]=351 at 3.68 min.

Intermediate 20

6-(5-Methylthiazol-2-yl)pyrido[2,3-d]pyrimidin-4(3H)-one

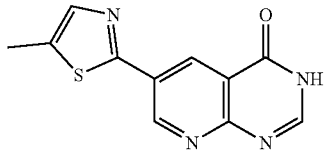 [SMILES: Cc1cnc(-c2cnc3nc[nH]c(=O)c3c2)s1]

Step 1: Preparation of 6-bromo-4-((2-(trimethylsilyl)ethoxy)methoxy)-pyrido[2,3-d]pyrimidine

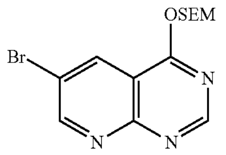

6-Bromopyrido[2,3-d]pyrimidin-4(3H)-one (7.0 g, 30.97 mmol) was dissolved in N,N-dimethylformamide (260 mL) and the reaction mixture cooled to 0° C. Sodium hydride (60% dispersion in mineral oil, 1.49 g, 37.16 mmol) was added portion-wise and the reaction mixture stirred for 30 min. (2-Chloromethoxyethyl)trimethylsilane (8.2 ml, 46.45 mmol) was then added dropwise. The reaction was then stirred at 0° C. for 1 hour and then allowed to warm to room temperature. The reaction mixture was quenched with water (50 mL) and partitioned with ethyl acetate (50 mL). The phases were separated, and the aqueous layer washed with ethyl acetate (3×50 mL). The combined organic phases were dried over $MgSO_4$, filtered and concentrated in vacuo. The crude product was purified by column chromatography on silica gel, eluting with 0-70% ethyl acetate in dichloromethane to give the title compound (6.0 g, 54%) as a white solid.

$^1H$ NMR (400 MHz, $CDCl_3$): δ 9.01 (d, J=2.4 Hz, 1H), 8.74 (d, J=2.4 Hz, 1H), 8.40 (s, 1H), 5.52 (s, 2H), 3.66-3.62 (m, 2H), 0.98-0.95 (m, 2H), 0.02 (s, 9H).

Step 2: Preparation of 5-methyl-2-(4-((2-(trimethylsilyl)ethoxy)-methoxy)pyrido[2,3-d]pyrimidin-6-yl)thiazole

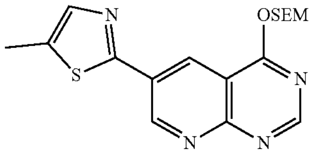

Nitrogen was bubbled for 5 minutes through a suspension of 6-bromo-4-((2-(trimethylsilyl)ethoxy)methoxy)pyrido[2,3-d]pyrimidine (3500 mg, 9.82 mmol), bis(pinacolato)diboron (2993 mg, 11.79 mmol), [1,1'-bis(diphenylphosphino)ferrocene]dichloropalladium(II) complex with dichloromethane (401 mg, 0.49 mmol), potassium acetate (1928 mg, 19.65 mmol) in 1,4-dioxane (80 mL). The reaction mixture was heated to 100° C. for 16 hours. The reaction was cooled to room temperature. To the resulting suspension was added water (16 mL), 2-bromo-5-methyl-1,3-thiazole (1836 mg, 10.3 mmol), caesium carbonate (6401 mg, 19.7 mmol) and another aliquot of [1,1'-bis(diphenylphosphino)ferrocene]dichloropalladium(II) complex with dichloromethane (22 mg, 0.027 mmol). The reaction was heated to 100° C. for a further 2 hours. The reaction was cooled to room temperature and the solvent was removed in vacuo. The residue was dissolved in dichloromethane and passed through a hydrophobic frit. The solvent was removed in vacuo and the residue was purified by column chromatography on silica gel eluting with 30-50% ethyl acetate in dichloromethane. The resulting residue was triturated with diethyl ether to give the title compound (2400 mg, 65%) as a pale yellow solid.

LCMS (Method 4): [MH+]=375 at 5.09 min.

Step 3: Preparation of 6-(5-Methylthiazol-2-yl)pyrido[2,3-d]pyrimidin-4(3H)-one

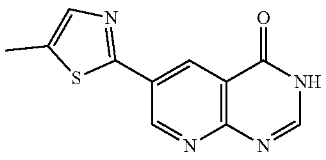 [SMILES: Cc1cnc(-c2cnc3nc[nH]c(=O)c3c2)s1]

5-Methyl-2-(4-((2-(trimethylsilyl)ethoxy)methoxy)pyrido[2,3-d]pyrimidin-6-yl)thiazole (1000 mg, 2.67 mmol) was dissolved in dichloromethane (15 mL) and trifluoroacetic acid (5 mL). The reaction mixture was stirred at room temperature for 5 hours. The solvent was removed in vacuo and the residue was quenched with a saturated solution of sodium bicarbonate and water. The solid was filtered and dried under reduced pressure to give the title compound (458 mg, 700%) as a yellow solid.

LCMS (Method 4): [MH+]=245 at 2.73 min.

The following compounds were synthesised following the procedure described for the preparation of 6-(5-Methylthiazol-2-yl)pyrido[2,3-d]pyrimidin-4(3H)-one:

| Intermediate No. | Chemical Name Structure | Analytical data $^1H$ NMR LC-MS |
|---|---|---|
| Intermediate 21 | 6-(5-methylpyrimidin-2-yl)pyrido[2,3-b]pyrimidin-4(3H)-one | LCMS (Method 3): [MH+] = 269 at 2.76 min. |
| | 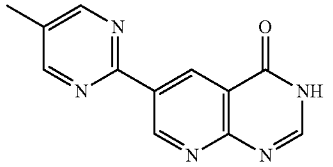 | |
| Intermediate 22 | 6-(5-methylpyridin-2-yl)pyrido[2,3-d]pyrimidin-4(3H)-one | LCMS (Method 3): [MH+] = 239 at 2.55 min. |
| | 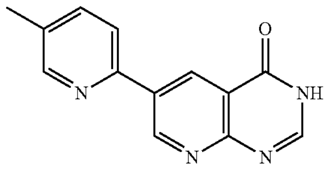 | |
| Intermediate 23 | 6-(5-fluoropyridin-2-yl)pyrido[2,3-d]pyrimidin-4(3H)-one | LCMS (Method 4): [MH+] = 272 at 3.02 min. |
| | 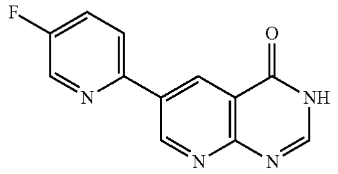 | |

Example 49

6-(5-methylthiazol-2-yl)-N-[[3-(trifluoromethyl)-1,2,4-oxadiazol-5-yl]methyl]pyrido[2,3-d]pyrimidin-4-amine

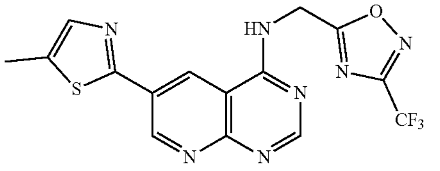

6-(5-Methylthiazol-2-yl)pyrido[2,3-d]pyrimidin-4(3N)-one (60 mg, 0.25 mmol) and N,N-diisopropylethyl amine (0.21 ml, 1.23 mmol) were suspended in toluene (2.5 mL). The reaction mixture was heated at 95° C. and phosphorus (V) oxychloride (0.027 ml, 0.30 mmol) was added. The reaction was heated at 95° C. for 2 hours and cooled to room temperature. The solvent was removed in vacuo. To the resulting residue was added [3-(trifluoromethyl)-1,2,4-oxadiazol-5-yl]methanamine hydrochloride (75 mg, 0.37 mmol), potassium carbonate (102 mg, 0.74 mmol) and N,N-dimethylformamide (2 mL). The reaction mixture was stirred at room temperature for 16 hours. The reaction was diluted with ethyl acetate and filtered through a pad of Celite©. The solvent was removed in vacuo. The resulting residue was purified by preparative HPLC to give the title compound (3.1 mg, 3%) as a pale yellow solid.

$^1$H NMR (400 MHz, DMSO): δ 9.90-9.86 (m, 1H), 9.60 (d, J=2.3 Hz, 1H), 9.30 (d, J=2.3 Hz, 1H), 8.69 (s, 1H), 7.83-7.81 (m, 1H), 5.25 (d, J=3.7 Hz, 2H), 2.63 (d, J=1.1 Hz, 3H). LCMS (Method 4): [MH+]=394 at 3.69 min.

The following compounds were synthesised following the procedure described for the preparation of 6-(5-methylthiazol-2-yl)-N-[[3-(trifluoromethyl)-1,2,4-oxadiazol-5-yl]methyl]pyrido[2,3-d]pyrimidin-4-amine:

| Example No. | Chemical Name<br>Structure | Analytical data<br>$^1$H NMR<br>LC-MS |
|---|---|---|
| Example 50 | 6-(5-methylthiazol-2-yl)-N-[[2-(trifluoromethyl)pyrimidin-5-yl]methyl]pyrido[2,3-d]pyrimidin-4-amine<br>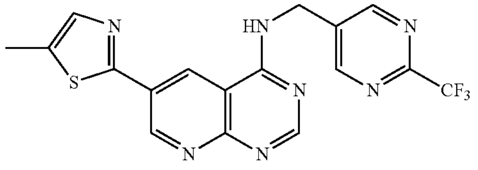 | $^1$H NMR (400 MHz, DMSO): δ 9.55 (t, J = 5.1 Hz, 1 H), 9.50 (d, J = 2.4 Hz, 1 H), 9.20 (d, J = 2.4 Hz, 1 H), 9.15 (s, 2 H), 8.66 (s, 1 H), 7.76-7.75 (m, 1 H), 4.95 (d, J = 4.7 Hz, 2 H), 2.57 (d, J = 1.1 Hz, 3 H). LCMS (Method 4): [MH+] = 404 at 3.26 min. |
| Example 51 | N-[(3-methyl-1,2,4-oxadiazol-5-yl)methyl]-6-(5-methylthiazol-2-yl)pyrido[2,3-d]pyrimidin-4-amine<br>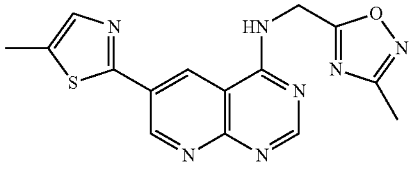 | $^1$H NMR (400 MHz, DMSO): δ 9.73 (br s, 1 H), 9.54 (d, J = 2.4 Hz, 1 H), 9.25 (d, J = 2.4 Hz, 1 H), 8.65 (s, 1 H), 7.77 (d, J = 1.2 Hz, 1 H), 5.05 (d, J = 3.3 Hz, 2 H), 2.58 (d, J = 1.2 Hz, 3 H), 2.32 (s, 3 H). LCMS (Method 4): [MH$^+$] = 340 at 2.63 min. |
| Example 52 | N-[(6-methylpyridazin-3-yl)methyl]-6-(5-methylthiazol-2-yl)pyrido[2,3-d]pyrimidin-4-amine<br>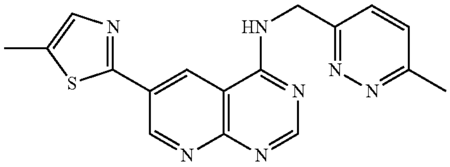 | $^1$H NMR (400 MHz, DMSO): δ 9.67-9.65 (m, 1 H), 9.55 (d, J = 2.4 Hz, 1 H), 9.30-9.28 (m, 1 H), 8.65 (s, 1 H), 7.80-7.79 (m, 1 H), 7.65 (d, J = 8.8 Hz, 1 H), 7.55 (d, J = 8.8 Hz, 1 H), 5.10-5.09 (m, 2 H), 2.64 (s, 3 H), 2.59 (s, 3 H). LCMS (Method 4): [MH$^+$] = 350 at 2.35 min. |

Intermediate 24

6-(1-((6-(4-fluorophenyl)pyrido[2,3-d]pyrimidin-4-yl)amino)ethyl)pyridin-2(11)-one

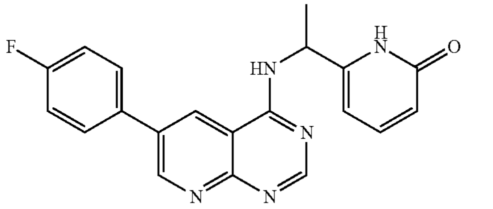 [SMILES: CC(Nc1ncnc2ncc(-c3ccc(F)cc3)cc12)c1cccc(=O)[nH]1]

Step 1: Preparation of 4-Chloro-6-(4-fluorophenyl)pyrido[2,3-d]pyrimidine

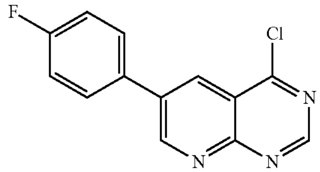 [SMILES: Fc1ccc(-c2cnc3ncnc(Cl)c3c2)cc1]

Phosphorus oxychloride (0.5 mL, 5.39 mmol) was added under nitrogen to a stirred suspension of 6-(4-fluorophenyl)pyrido[2,3-d]pyrimidin-4(3H)-one (1 g, 4.15 mmol) and N,N-diisopropylethylamine (3.6 mL, 20.7 mmol) in anhydrous toluene (20 mL). The mixture was heated to 90° C. for 2 hours, after which time analysis by LC-MS indicated conversion to the desired target. The solvents were removed under vacuum and the residue obtained was partitioned between DCM (40 mL) and saturated aqueous solution of $NaHCO_3$ (10 mL). The layers were thoroughly mixed, before separating and the aqueous phase was re-extracted with DCM (20 mL). The combined organics were washed with saturated aqueous solution of $NaHCO_3$ (10 mL) and then water (10 mL) before drying by passing through a phase separating frit. The solvents were removed in vacuo, to give a dark brown semi-solid which was used immediately in the next step without further purification (1.6 g, >100%).

Step 2: Preparation of 6-(1-((6-(4-fluorophenyl)pyrido[2,3-d]pyrimidin-4-yl)amino)ethyl)pyridin-2(1H)-one

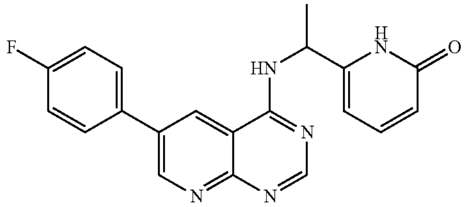 [SMILES: CC(Nc1ncnc2ncc(-c3ccc(F)cc3)cc12)c1cccc(=O)[nH]1]

4-Chloro-6-(4-fluorophenyl)pyrido[2,3-d]pyrimidine (150 mg, 0.58 mmol), 6-(1-aminoethyl)pyridin-2(1H)-one. HBr (152 mg, 0.69 mmol) and N,N-diisopropylethylamine (0.40 mL, 2.31 mmol) were stirred in N,N-dimethylformamide (4 mL) at 40° C. for 4 days. The yellow precipitate was filtered off and purified by preparative HPLC to give the title compound (61 mg, 29%) as a colourless solid.

$^1$H NMR (400 MHz, DMSO): δ 11.76-11.75 (m, 1H), 9.42 (d, J=2.5 Hz, 1H), 9.22 (d, J=2.5 Hz, 1H), 8.83 (d, J=6.8 Hz, 1H), 8.65 (s, 1H), 8.03 (ddd, J=3.2, 5.4, 12.0 Hz, 2H), 7.50 (dd, J=8.8, 8.8 Hz, 2H), 7.40 (dd, J=8.0, 8.0 Hz, 1H), 6.28-6.21 (m, 2H), 5.38 (dd, J=6.9, 6.9 Hz, 1H), 1.65 (d, J=7.1 Hz, 3H). LCMS (Method 4): [MH+]=362 at 2.85 min.

The following compounds were synthesised following the same procedure described for the preparation of 6-(1-((6-(4-fluorophenyl)pyrido[2,3-d]pyrimidin-4-yl)amino)ethyl)pyridin-2(1H)-one using the appropriate amine reagent:

| Example No. | Chemical Name<br>Structure | Analytical data<br>$^1$H NMR<br>LC-MS |
|---|---|---|
| Example 54 | 2-((6-(4-fluorophenyl)pyrido[2,3-d]pyrimidin-4-yl)amino)-2-(5-methyl-1,2,4-oxadiazol-3-yl)ethan-1-ol<br>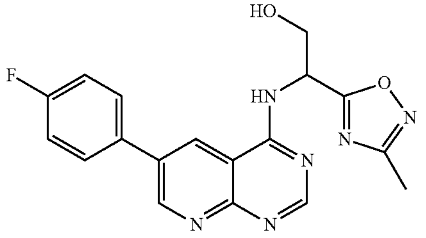 | $^1$H NMR (400 MHz, DMSO): δ 9.42 (s, 1 H), 9.22 (s, 1 H), 9.13 (d, J = 7.0 Hz, 1 H), 8.64 (s, 1 H), 8.00 (dd, J = 6.3, 6.3 Hz, 2 H), 7.45 (dd, J = 8.5, 8.5 Hz, 2 H), 5.83-5.76 (m, 1 H), 5.45 (dd, J = 5.4, 5.4 Hz, 1 H), 4.07 (dd, J = 5.5, 5.5 Hz, 2 H), 2.34 (s, 3 H). LCMS (Method 4): [MH+] = 367 at 3.23 min. |

-continued

| Example No. | Chemical Name<br>Structure | Analytical data<br>$^{1}$H NMR<br>LC-MS |
|---|---|---|
| Example 55 | (R)-6-(4-fluorophenyl)-N-(1-(5-methyl-1,3,4-oxadiazol-2-yl)ethyl)pyrido[2,3-d[pyrimidin-4-amine<br>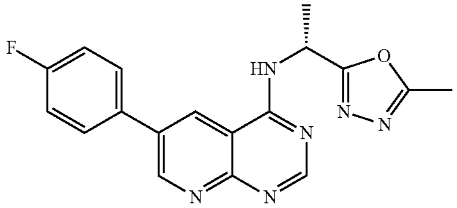 | $^{1}$H NMR (400 MHz, DMSO): δ 9.30 (d, J = 2.4 Hz, 1 H), 9.04 (d, J = 2.4 Hz, 1 H), 8.59 (s, 1 H), 7.88 (dd, J = 5.5, 8.6 Hz, 2 H), 7.37 (dd, J = 8.8, 8.8 Hz, 2 H), 5.79 (q, J = 7.0 Hz, 1 H), 2.43 (s, 3 H), 1.70 (d, J = 7.0 Hz, 3 H). NH not observed LCMS (Method 4): [MH+] = 351 at 2.83 min. Chiral analysis (Method 26) at 1.69 min. |
| Example 56 | 6-(4-fluorophenyl)-N-(1-(5-methyl-1,3,4-thiadiazol-2-yl)ethyl)pyrido[2,3-d]pyrimidin-4-amine<br>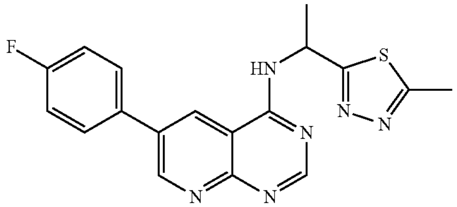 | $^{1}$H NMR (400 MHz, DMSO): δ 9.40 (d, J = 2.5 Hz, 1 H), 9.19-9.13 (m, 2 H), 8.69 (s, 1 H), 7.97 (ddd, J = 3.1, 5.3, 12.0 Hz, 2 H), 7.45 (dd, J = 8.9, 8.9 Hz, 2 H), 6.01-5.95 (m, 1 H), 2.67 (s, 3 H), 1.82 (d, J = 7.0 Hz, 3 H). LCMS (Method 4): [MH+] = 367 at 3.07 min. |
| Example 58 | (R)-6-(4-fluorophenyl)-N-(1-(5-methyl-1,2,4-oxadiazol-3-yl)ethyl)pyrido[2,3-d]pyrimidin-4-amine<br>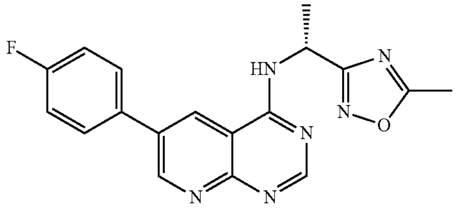 | 1H NMR (400 MHz, DMSO-d6) d ppm 9.34 (d, J = 2.63 Hz, 1 H), 9.12 (d, J = 2.19 Hz, 1 H), 8.96 (d, J = 7.89 Hz, 1 H), 8.59 (s, 1 H), 7.93 (dd, J = 8.55, 5.48 Hz, 2 H), 7.39 (t, J = 8.77 Hz, 2 H), 5.68-5.76 (m, 1 H), 2.53 (s, 3 H), 1.64 (d, J = 7.02 Hz, 3 H). LCMS (Method 4.1): [MH+] = 351.1 at 0.66 min |
| Example 59 | 6-(4-fluorophenyl)-N-(2-(3-methyl-1,2,4-oxadiazol-5-yl)propan-2-yl)pyrido[2,3-d]pyrimidin-4-amine<br>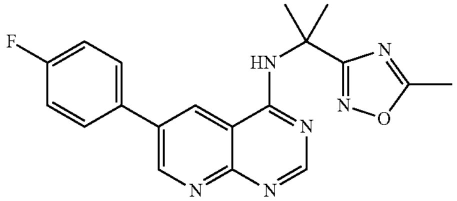 | 1H NMR (400 MHz, DMSO-d6) d ppm 9.37 (d, J = 2.19 Hz, 1 H), 9.21 (d, J = 2.19 Hz, 1 H), 8.79 (s, 1 H), 8.41 (s, 1 H), 7.95-8.02 (m, 2 H), 7.40-7.50 (m, 2 H), 2.31 (s, 3 H), 1.88 (s, 6H). LCMS (Method 4.1): [MH+] = 365.1 at 0.75 min. |
| Example 60 | N-(1-(3,5-difluoropyridin-2-yl)ethyl)-6-(4-fluorophenyl)pyrido[2,3-d]pyrimidin-4-amine<br>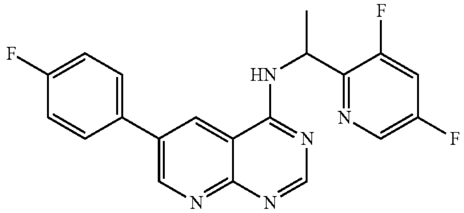 | 1H NMR (400 MHz, DMSO-d6) δ ppm 9.31 (d, J = 2.19 Hz, 1 H), 9.19 (d, J = 2.41 Hz, 1 H), 8.93 (br d, J = 7.23 Hz, 1 H), 8.50 (s, 1 H), 8.42 (d, J = 2.41 Hz, 1 H), 7.86-7.97 (m, 3 H), 7.39 (t, J = 8.77 Hz, 2 H), 5.83 (br quin, J = 7.00 Hz, 1 H), 1.60 (d, J = 7.02 Hz, 3 H). LCMS (Method 4.1): [MH+] = 389.1 at 0.79 min |

-continued

| Example No. | Chemical Name<br>Structure | Analytical data<br>$^1$H NMR<br>LC-MS |
|---|---|---|
| Example 63 | 6-(4-fluorophenyl)-N-(2-(3-methyl-1,2,4-oxadiazol-5-yl)ethyl)pyrido[2,3-d[pyrimidin-4-amine<br>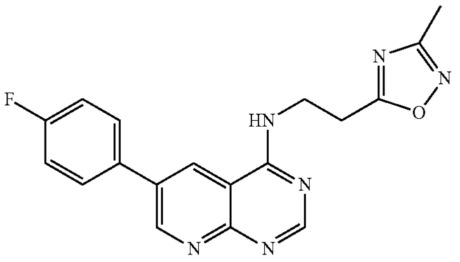 | 1H NMR (400 MHz, DMSO-d6) δ ppm 9.31 (d, J = 2.41 Hz, 1 H), 8.92 (d, J = 2.41 Hz, 1 H), 8.85 (br t, J = 5.37 Hz, 1 H), 8.59 (s, 1 H), 7.88 (dd, J = 8.66, 5.37 Hz, 2 H), 7.39 (t, J = 8.77 Hz, 2 H), 3.90-3.99 (m, 2 H), 3.24-3.32 (m, 2 H), 2.26 (s, 3 H). LCMS (Method 4.1): [MH+] = 351.0 at 0.58 min |
| Example 63a | N-[1-(3,5-difluoro-2-pyridyl)ethyl]-6-(4-fluorophenyl)pyrido[2,3-d]pyrimidin-4-amine<br>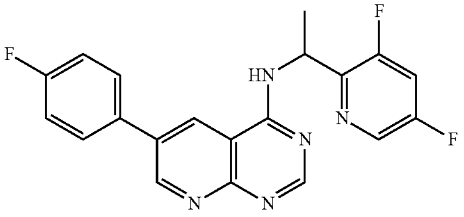 | $^1$H NMR (400 MHz, DMSO): δ 9.36 (d, J = 2.4 Hz, 1 H), 9.24 (d, J = 2.4 Hz, 1 H), 9.00-8.98 (m, 1 H), 8.57 (s, 1 H), 8.47 (d, J = 2.4 Hz, 1 H), 8.00-7.92 (m, 3 H), 7.47-7.41 (m, 2 H), 5.90-5.84 (m, 1 H), 1.65 (d, J = 6.8 Hz, 3 H). LCMS (Method 4): [MH+] = 382 at 4.3 min. |

Example 2

(R)-5-(1-((6-(4-fluorophenyl)pyrido[2,3-d]pyrimidin-4-yl)amino)ethyl)-2-(trifluoromethyl)pyridine 1-oxide

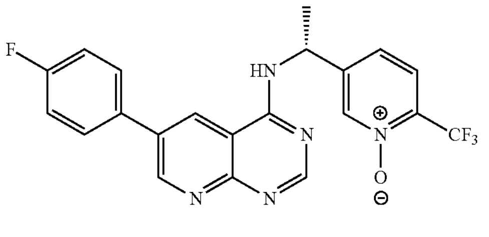 [SMILES: C[C@@H](Nc1ncnc2ncc(-c3ccc(F)cc3)cc12)c1ccc(C(F)(F)F)[n+]([O-])c1]

6-(4-Fluorophenyl)pyrido[2,3-d]pyrimidin-4(3H)-one (intermediate 2) (23.5 g, 97.4 mmol, 1 eq) was suspended in $SOCl_2$ (240 mL), then DMF (2.5 mL) was added dropwise. The reaction mixture was heated to reflux until a clear solution formed. The reaction was then complete and volatiles were removed under reduced pressure. The residue was macerated with EtOAc, then filtered and dried to give 4-chloro-6-(4-fluorophenyl)pyrido[2,3-d]pyrimidine (23.6 g, 91.9 mmol, 94% Yield).

DIPEA (0.3 mL, 1.722 mmol) was added to a mixture of 4-chloro-6-(4-fluorophenyl)pyrido[2,3-d]pyrimidine (100 mg, 0.385 mmol) and (R)-5-(1-aminoethyl)-2-(trifluoromethyl)pyridine 1-oxide hydrochloride (112 mg, 0.462 mmol) in DMF (Volume: 2 mL). Stirring went on at 80° C. for 16 h. The reaction mixture was diluted with AcOEt, washed with semi-saturated aqueous NaCl solution, then with brine. The organic layer was dried over sodium sulfate, filtered and concentrated under reduced pressure. Purification by DP chromatography (Biotage Isolera, 28 g NH cartridge, gradient elution from 0 to 60% AcOEt in dichloromethane) followed by RP chromatography (Biotage Isolera, 30 g C18 cartridge, gradient elution from 0 to 35% B in A. A: water/acetonitrile 95:5+0.05% HCOOH, B: acetonitrile/water 95:5+0.05% HCOOH) yielded (R)-5-(1-((6-(4-fluorophenyl)pyrido[2,3-d]pyrimidin-4-yl)amino)ethyl)-2-(trifluoromethyl)pyridine 1-oxide (122 mg, 0.284 mmol, 73.8% yield) as an off-white powder.

LCMS (Method 4.1): 0.70 min, 430.1 [M+H]+.

$^1$H NMR (400 MHz, DMSO-d6) δ ppm 9.36 (d, J=2.19 Hz, 1H) 9.14 (d, J=2.19 Hz, 1H) 8.88 (d, J=6.80 Hz, 1H) 8.61 (s, 1H) 8.59 (s, 1H) 7.97 (dd, J=8.47, 5.38 Hz, 2H) 7.91 (d, J=8.33 Hz, 1H) 7.58 (d, J=8.33 Hz, 1H) 7.44 (t, J=8.77 Hz, 2H) 5.55 (quin, J=6.96 Hz, 1H) 1.66 (d, J=7.02 Hz, 3H).

The following Examples were synthesised via adaptations of the same procedure.

| Example No. | Chemical Name<br>Structure | Analytical data<br>$^1$H NMR<br>LC-MS |
|---|---|---|
| Example 3 | (R)-6-(4-fluorophenyl)-N-(1-(6-methylpyridazin-3-yl)ethyl)pyrido[2,3-d]pyrimidin-4-amine<br>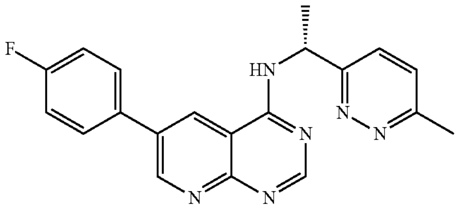 | LCMS (Method 4.1): 0.60 min, 361.2 [M + H]+. 1H NMR (400 MHz, DMSO-d6) δ ppm 9.36 (d, J = 1.75 Hz, 1 H) 9.22 (d, J = 1.75 Hz, 1 H) 9.02 (br d, J = 7.23 Hz, 1 H) 8.54 (s, 1 H) 7.98 (dd, J = 8.22, 5.59 Hz, 2 H) 7.64 (d, J = 8.77 Hz, 1 H) 7.50 (d, J = 8.65 Hz, 1 H) 7.43 (t, J = 8.66 Hz, 2 H) 5.76 (quin, J = 7.02 Hz, 1 H) 2.58 (s, 3 H) 1.71 (d, J = 7.02 Hz, 3 H). |
| Example 4 | (S)-2-((6-(4-fluorophenyl)pyrido[2,3-d]pyrimidin-4-yl)amino)-2-(6-methoxypyridin-3-yl)ethan-1-ol<br>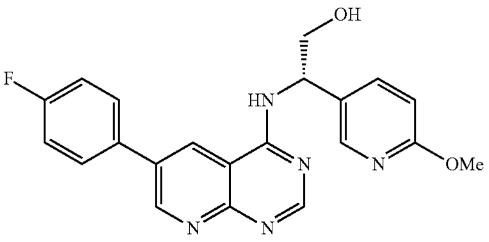 | LCMS (Method 4.1): 0.63 min, 392.2 [M + H]+, 1H NMR (400 MHz, DMSO-d6) δ ppm 9.30 (s, 1 H) 9.14 (s, 1 H) 8.78-9.46 (m, 1 H) 8.76 (br d, J = 7.67 Hz, 1 H) 8.54 (d, J = 0.88 Hz, 1 H) 8.23 (br s, 1 H) 7.93 (dd, J = 7.34, 5.37 Hz, 2 H) 7.77 (br d, J = 8.55 Hz, 1 H) 7.40 (t, J = 8.12 Hz, 2 H) 6.76 (d, J = 8.55 Hz, 1 H) 5.48 (q, J = 6.94 Hz, 1 H) 5.10 (t, J = 5.48 Hz, 1 H) 3.78 (d, J = 1.38 Hz, 5 H) |
| Example 5 | 6-(4-fluorophenyl)-N-(2-morpholinoethyl)pyrido[2,3-d]pyrimidin-4-amine formate<br>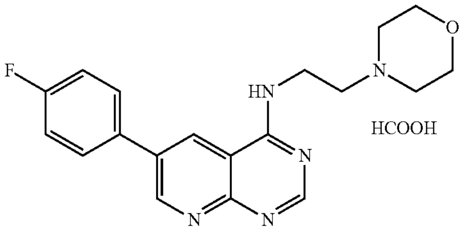 | LCMS (Method 4.1):: 0.34 min, 354.1 [M + H]+, 1H NMR (400 MHz, DMSO-d6) δ ppm 9.28 (d, J = 2.41 Hz, 1 H) 8.95 (d, J = 2.41 Hz, 1 H) 8.62 (br t, J = 4.82 Hz, 1 H) 8.57 (s, 1 H) 7.86-7.92 (m, 2 H) 7.39 (t, J = 8.88 Hz, 2 H) 3.61-3.76 (m, 2 H) 3.51-3.57 (m, 4 H) 2.58 (t, J = 6.91 Hz, 2 H) 2.39-2.45 (m, 4 H) |

Intermediate 3—Procedure A

6-Bromo-N-(1-(3-methyl-1,2,4-oxadiazol-5-yl)ethyl)pyrido[2,3-d]pyrimidin-4-amine

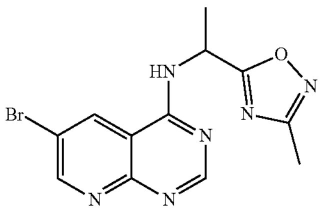 [SMILES: Cc1noc(C(C)Nc2ncnc3ncc(Br)cc23)n1]

To a mixture of 6-bromopyrido[2,3-d]pyrimidin-4(3H)-one (Intermediate 1) (1.0 g, 4.42 mmol) and 1-(3-methyl-1,2,4-oxadiazol-5-yl)ethan-1-amine hydrochloride (996 mg, 4.98 mmol) in N,N-dimethylformamide (25 mL) was added N,N-diisopropylethylamine (3.9 mL, 22.12 mmol) and (benzotriazol-1-yloxy)tripyrrolidinophosphonium hexafluorophosphate (2.76 g, 5.31 mmol) and the mixture was heated to 40° C. for 5 hours and at room temperature for 2 days. The reaction was filtered and the solid was washed with ethyl acetate (20 mL). The filtrate was washed with water (100 mL) then the aqueous layer was extracted with ethyl acetate (3×40 mL). The organic phases were combined, washed with brine (50 mL), passed through a hydrophobic frit and the solvent was removed in vacuo. The residue was purified by chromatography on silica gel, eluting with 0-10% methanol in dichloromethane. The fractions containing product were combined and triturated with diethyl ether to give the title compound (766 mg, 46% yield) as a white solid.

LCMS (Method 3): [MH+]=335 at 2.94 min.

Intermediate 4—Procedure B 6-bromo-N-((6-methylpyridin-3-yl)methyl)pyrido[2,3-d]pyrimidin-4-amine

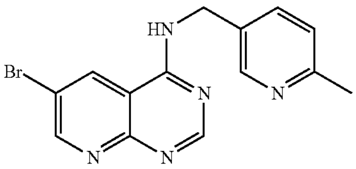 [SMILES: Cc1ccc(CNc2ncnc3ncc(Br)cc23)cn1]

A mixture of 6-bromo-4-chloropyrido[2,3-d]pyrimidine (1 g, 4.09 mmol), (6-methylpyridin-3-yl)methanamine (0.500 g, 4.09 mmol) and triethylamine (3 ml, 21.52 mmol) in 1,4-Dioxane/DMF 5:1 (Volume: 12 ml) was stirred at 100° C. for 16 h. The reaction mixture was concentrated under reduced pressure. Purification by column chromatography (Biotage Isolera, 55 g NH cartridge, gradient elution from 0 to 100% Acetone in heptane) yielded 6-bromo-N-((6-methylpyridin-3-yl)methyl)pyrido[2,3-d]pyrimidin-4-amine (1.21 g, 3.66 mmol, 90% yield) as a pale yellow powder. Expected product was recovered both in fractions and on top of the cartridge as an insoluble precipitate.

LCMS (CSH basic method 2 min): 0.66 min, m/z 329.8 and 331.7 [M]+ and [M+2]+.

The following intermediates were synthesised via adaptations of procedure A or B (see table for specific procedure) reacting suitable substrate and amine intermediate:

| Intermediate No. | Chemical Name Structure | Analytical data | Starting material - Procedure |
|---|---|---|---|
| Intermediate 5 | 6-Bromo-N-((6-methylpyridazin-3-yl)methyl)pyrido[2,3-d]pyrimidin-4-amine 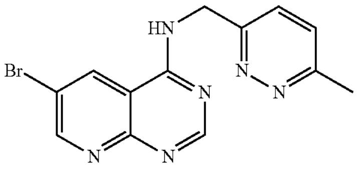 | $^1H$ NMR (400 MHz, DMSO): δ 9.40-9.39 (m, 1 H), 9.15 (d, J = 6.1 Hz, 2 H), 8.66 (s, 1 H), 7.64 (d, J = 8.6 Hz, 1 H), 7.55 (d, J = 8.6 Hz, 1 H), 5.06 (d, J = 5.6 Hz, 2 H), 2.65 (s, 3 H). | 6-bromopyrido[2,3-d]pyrimidin-4(3H)-one, (Intermediate 1) procedure A |
| Intermediate 6 | (R)-6-Bromo-N-(1-(2-(trifluoromethyl)pyrimidin-5-yl)ethyl)pyrido[2,3-d]-pyrimidin-4-amine 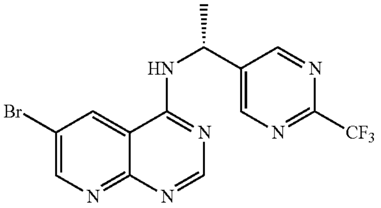 | LCMS (Method 4): [MH+] = 399.0 and 401.0 at 3.43 min. | 6-bromopyrido[2,3-d]pyrimidin-4(3H)-one, (Intermediate 1) procedure A |

Example 6

N-(1-(3-Methyl-1,2,4-oxadiazol-5-yl)ethyl)-6-(5-methylthiazol-2-yl)pyrido[2,3-d]-pyrimidin-4-amine

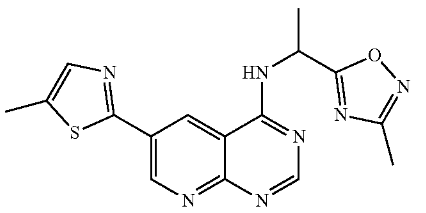 [SMILES: Cc1noc(C(C)Nc2ncnc3ncc(-c4ncc(C)s4)cc23)n1]

Nitrogen was bubbled for 5 min through a solution of 5-methyl-2-(tributylstannyl)thiazole (902 mg, 2.67 mmol), 6-bromo-N-(1-(3-methyl-1,2,4-oxadiazol-5-yl)ethyl)pyrido[2,3-d]pyrimidin-4-amine (Intermediate 3) (2.75 mg, 0.82 mmol) in N,N-dimethylformamide (12 mL), then tetrakis(triphenylphosphine)palladium(0) (142 mg, 0.123 mmol) was added. The resulting mixture was heated to 95° C. for 18 hours. After return to room temperature, the reaction was diluted with water (60 mL) and brine (25 mL) and extracted with ethyl acetate (3x30 mL). The combined organic phases were filtered through a Celite© cartridge, washed with water (50 mL), dried over $MgSO_4$ and filtered. The solvent was removed in vacuo. The residue was purified by chromatography on silica gel eluting with 0-100% methanol in dichloromethane to give the title compound (140 mg, 48% yield) as an off-white solid.

LCMS (Method 3): [MH+]=354 at 3.25 min.

The following compounds were synthesised following the same procedure described for the preparation of N-(1-(3-Methyl-1,2,4-oxadiazol-5-yl)ethyl)-6-(5-methylthiazol-2-yl)pyrido[2,3-d]-pyrimidin-4-amine using the appropriate stannane reagent and starting from intermediate reported in table.

| Example No. | Chemical Name Structure | Analytical data $^1H$ NMR LC-MS | Starting Intermediate |
|---|---|---|---|
| Example 7 | N-((6-Methylpyridazin-3-yl)methyl)-6-(5-methylpyridin-2-yl)pyrido[2,3-d]pyrimidin-4-amine 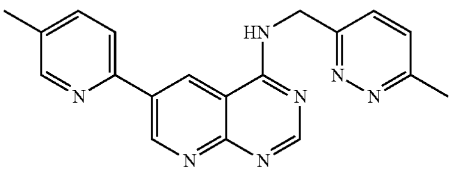 | $^1H$ NMR (400 MHz, $CDCl_3$): δ 9.61 (d, J = 2.0 Hz, 1 H), 8.97 (d, J = 2.0 Hz, 1 H), 8.82 (s, 1 H), 8.52 (s, 1 H), 8.09 (dd, J = 5.4, 5.4 Hz, 1 H), 7.74 (d, J = 7.8 Hz, 1 H), 7.61 (d, J = 7.3 Hz, 1 H), 7.53 (d, J = 8.6 Hz, 1 H), 7.38 (d, J = 8.6 Hz, 1 H), 5.13 (d, J = 4.5 Hz, 2 H), 2.74 (s, 3 H), 2.41 (s, 3 H). LCMS (Method 3): [MH+] = 344 at 2.84 min. | Intermediate 5 |
| Example 8 | 6-(5-Chloropyridin-2-yl)-N-((6-methylpyridazin-3-yl)methyl)pyrido[2,3-d]pyrimidin-4-amine 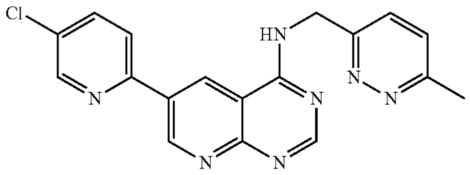 | $^1H$ NMR (400 MHz, DMSO): δ 9.51 (d, J = 2.3 Hz, 1 H), 9.32 (t, J = 5.6 Hz, 1H), 9.27 (d, J = 1.8 Hz, 1 H), 8.62 (d, J = 1.3 Hz, 1 H), 8.42 (s, 1 H), 8.05-7.99 (m, 2 H), 7.41 (d, J = 8.6 Hz, 1 H), 7.31 (d, J = 8.6 Hz, 1 H), 4.86 (d, J = 4.8 Hz, 2 H), 2.40 (s, 3 H). LCMS (Method 3): [MH+] = 364 at 3.10 min. | Intermediate 5 |
| Example 9 | (R)-6-(5-Methylpyridin-2-yl)-N-(1-(2-(trifluoromethyl)pyrimidin-5-yl)ethyl)pyrido[2,3-d]pyrimidin-4-amine 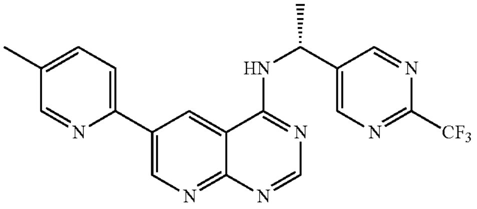 | $^1H$ NMR (400 MHz, DMSO): δ 9.71 (s, 1 H), 9.52-9.48 (m, 1 H), 9.21 (s, 3 H), 8.63 (d, J = 12.1 Hz, 2 H), 8.15 (d, J = 8.1 Hz, 1 H), 7.87 (d, J = 7.8 Hz, 1 H), 5.72-5.70 (m, 1 H), 2.42 (s, 3 H), 1.77 (d, J = 6.6 Hz, 3 H). LCMS (Method 3): [MH+] = 412 at 3.95 min. | Intermediate 6 |

-continued

| Example No. | Chemical Name Structure | Analytical data $^1$H NMR LC-MS | Starting Intermediate |
|---|---|---|---|
| Example 10 | 6-(5-methylpyridin-2-yl)-N-((6-methylpyridin-3-yl)methyl)pyrido[2,3-d]pyrimidin-4-amine 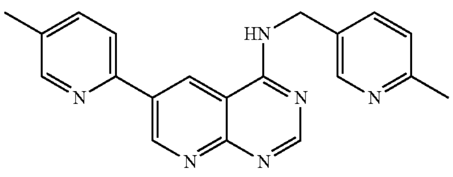 | 1H NMR (400 MHz, DMSO-d6) δ ppm 9.68 (d, J = 2.6 Hz, 1 H), 9.36 (d, J = 2.6 Hz, 1 H), 9.29 (t, J = 5.7 Hz, 1 H), 8.63 (s, 1 H), 8.60 (s, 1 H), 8.51 (d, J = 1.8 Hz, 1 H), 8.07 (d, J = 8.3 Hz, 1 H), 7.82 (dd, J = 8.3, 1.8 Hz, 1 H), 7.70 (dd, J = 7.9, 2.2 Hz, 1 H), 7.21 (d, J = 7.9 Hz, 1 H), 4.79 (d, J = 5.7 Hz, 2 H), 2.44 (s, 3 H), 2.38 (s, 3 H). LCMS: (Method 4.1): 0.33 min, 342.9 m/z [M + H]+. | Intermediate 4 |
| Example 107 | 6-(5-methylthiazol-2-yl)-N-[(1R)-1-[2-(trifluoromethyl)pyrimidin-5-yl]ethyl]pyrido[2,3-d]pyrimidin-4-amine 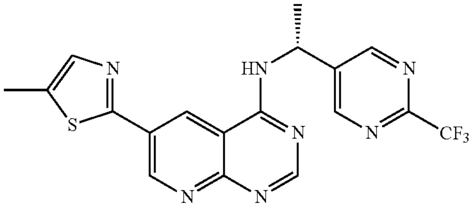 | $^1$H NMR (400 MHz, DMSO): δ 9.47 (d, J = 2.4 Hz, 1 H), 9.32 (d, J = 2.4 Hz, 1 H), 9.25-9.23 (m, 1 H), (s, 2 H), 8.59 (s, 1 H), 7.79-7.76 (m, 1 H), 5.69-5.67 (m, 1 H), 2.58 (s, 3 H), 1.73 (d, J = 7.1 Hz, 3 H). LCMS (Method 3): [MH+] = 418 at 4.29 min. Chiral analysis (Method 27) at 3.38 min. | Intermediate 6 |

Intermediate 7

6-(5-Chloropyridin-2-yl)pyrido[2,3-d]pyrimidin-4(3H)-one

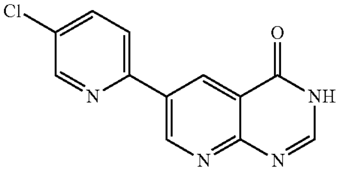 [SMILES: O=c1[nH]cnc2ncc(-c3ccc(Cl)cn3)cc12]

Nitrogen was bubbled for 5 min through a solution of 6-bromopyrido[2,3-d]pyrimidin-4(3H)-one (Intermediate 1) (832 mg, 3.68 mmol), 5-chloro-2-(tributylstannyl)thiazole (2.0 g, 4.97 mmol) in N,N-dimethylformamide (35 mL). Tetrakis(triphenylphosphine)palladium(0) (638 mg, 0.552 mmol) was added and the mixture was heated to 95° C. for 18 hours. After return to room temperature, the reaction was filtered and the solid was washed with N,N-dimethylformamide (50 mL) then with 10% methanol in dichloromethane (3×25 mL) to give the title compound (470 mg, 49%) as an off-white solid.

$^1$H NMR (400 MHz, DMSO): δ 12.72-12.72 (m, 1H), 9.70-9.66 (m, 1H), 9.15 (s, 1H), 8.85 (s, 1H), 8.42 (s, 1H), 8.34 (d, J=8.6 Hz, 1H), 8.16 (d, J=7.3 Hz, 1H).

Example 11

(R)-6-(5-Chloropyridin-2-yl)-N-(1-(2-(trifluoromethyl)pyrimidin-5-yl)ethyl)pyrido[2,3-d]pyrimidin-4-amine

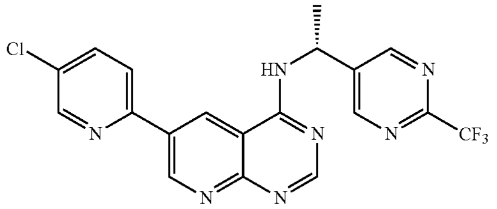 [SMILES: C[C@@H](Nc1ncnc2ncc(-c3ccc(Cl)cn3)cc12)c1cnc(C(F)(F)F)nc1]

To a solution of 6-(5-chloropyridin-2-yl)pyrido[2,3-d]pyrimidin-4(3H)-one (intermediate 7) (80 mg, 0.31 mmol) in N,N-dimethylformamide (8 mL) was added (6-methylpyridazin-3-yl)methanamine dihydrochloride (69 mg, 0.35 mmol), N,N-diisopropylethylamine (0.27 mL, 1.55 mmol), and (benzotriazol-1-yloxy)tripyrrolidinophosphonium hexafluorophosphate (1.93 mg, 0.37 mmol). The resulting mixture was heated to 60° C. for 48 hours. After return to room temperature, the reaction was diluted with dichloromethane (10 mL) and water (20 mL) and filtered. The solid was washed with water (5 mL) and dichloromethane (10 mL) and the filtrate separated. The aqueous phase was extracted further with dichloromethane (2×15 mL). The organic phases were combined, passed through a hydrophobic frit and the solvent was removed in vacuo. The residue was purified by preparative HPLC to give the title compound (9.5 mg, 7%) as an off-white solid.

$^1$H NMR (400 MHz, DMSO): δ 9.74 (d, J=2.0 Hz, 1H), 9.55 (d, J=2.0 Hz, 1H), 9.25 (s, 2H), 9.21 (d, J=6.1 Hz, 1H), 8.88 (d, J=2.0 Hz, 1H), 8.67 (s, 1H), 8.32 (d, J=8.6 Hz, 1H), 8.25 (dd, J=2.3, 8.6 Hz, 1H), 5.77-5.71 (m, 1H), 1.81 (d, J=7.1 Hz, 3H). LCMS (Method 4): [MH+]=432 at 3.71 min.

The following compounds were synthesised following the same procedure described for the preparation of (R)-6-(5-Chloropyridin-2-yl)-N-(1-(2-(trifluoromethyl)pyrimidin-5-yl)ethyl)pyrido[2,3-d]pyrimidin-4-amine using the appropriate amine reagent:

| Example No. | Chemical Name Structure | Analytical data $^1$H NMR LC-MS |
|---|---|---|
| Example 12 | 6-(5-Chloropyridin-2-yl)-N-(1-(3-methyl-1,2,4-oxadiazol-5-yl)ethyl)pyrido[2,3-d]pyrimidin-4-amine 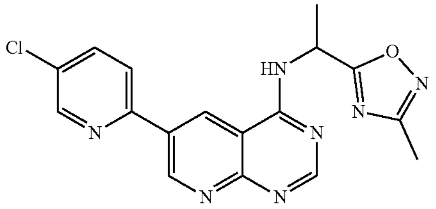 [SMILES: Cc1noc(C(C)Nc2ncnc3ncc(-c4ccc(Cl)cn4)cc23)n1] | $^1$H NMR (400 MHz, DMSO): δ 9.66 (d, J = 2.3 Hz, 1 H), 9.44 (d, J = 2.0 Hz, 1 H), 9.28 (d, J = 6.8 Hz, 1 H), 8.75 (d, J = 2.0 Hz, 1 H), 8.58 (s, 1 H), 8.18 (d, J = 8.3 Hz, 1 H), 8.12 (dd, J = 2.4, 8.5 Hz, 1 H), 5.78-5.72 (m, 1 H), 2.25 (s, 3 H), 1.68 (d, J = 7.1 Hz, 3 H). LCMS (Method 3): [MH+] = 368 at 3.87 min. |

Example 13

(R)-6-(4-Fluorophenyl)-N-(1-(2-(trifluoromethyl)pyrimidin-5-yl)ethyl)pyrido[2,3-d]pyrimidin-4-amine

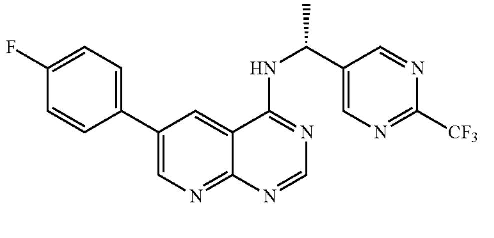 [SMILES: C[C@@H](Nc1ncnc2ncc(-c3ccc(F)cc3)cc12)c1cnc(C(F)(F)F)nc1]

Nitrogen was bubbled for 10 min through a mixture of (R)-6-bromo-N-(1-(2-(trifluoromethyl)pyrimidin-5-yl)ethyl)pyrido[2,3-d]pyrimidin-4-amine (100 mg, 0.251 mmol), potassium carbonate (104 mg, 0.752 mmol), 4-fluorophenylboronic acid (39 mg, 0.276 mmol), [1,1'-bis(diphenylphosphino)ferrocene]dichloropalladium(II) (18 mg, 0.0251 mmol), 1,4-dioxane (2 mL) and water (0.5 mL). The reaction was heated to 110° C. for 20 minutes in a microwave reactor. After return to room temperature, water (2 mL) was added and the mixture was extracted with Ethyl acetate (2×20 mL). The combined organic phases were dried over $MgSO_4$, filtered and the solvent was removed in vacuo. The residue was purified by flash chromatography eluting with 0-20% methanol in dichloromethane then by preparative HPLC to give the title compound (37 mg, 35%) as an off-white solid.

$^1$H NMR (400 MHz, $CDCl_3$): δ 9.21 (d, J=2.4 Hz, 1H), 8.56 (d, J=2.3 Hz, 1H), 7.51 (d, J=1.0 Hz, 1H), 7.44 (d, J=8.5 Hz, 1H), 7.36 (d, J=8.7 Hz, 1H), 5.04 (d, J=4.8 Hz, 2H), 4.03-4.03 (m, 2H), 3.97-3.96 (m, 2H), 3.69 (dd, J=5.1, 5.1 Hz, 2H), 3.53 (dd, J=5.1, 5.1 Hz, 2H), 2.75 (s, 3H), 2.54 (s, 3H), 2.16 (s, 3H). LCMS (Method 3): [MH+]=476.0 at 3.06 min.

The compound 18 was obtained as a side product in the preparation of Example 17.

The following intermediates were synthesised via adaptations of the same procedure starting from suitable intermediates:

| Example No. | Chemical Name Structure | Analytical data $^1$H NMR LC-MS | Starting Intermediate |
|---|---|---|---|
| Example 14 | N-((6-methylpyridin-3-yl)methyl)-6-(p-tolyl)pyrido[2,3-d]pyrimidin-4-amine 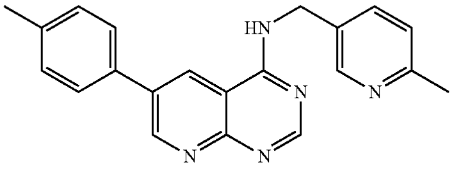 | LCMS (Method 4.1): 0.38 min, 342.0 m/z [M + H]+, CSH 2 min. 1H NMR (400 MHz, DMSO-d6) δ ppm 9.34 (d, J = 2.2 Hz, 1 H), 9.12-9.21 (bs, 1 H), 9.03 (d, J = 2.6 Hz, 1 H), 8.60 (s, 1 H), 8.51 (d, J = 1.8 Hz, 1 H), 7.79 (d, J = 8.3 Hz, 2 H), 7.66-7.73 (m, 1 H), 7.37 (d, J = 8.3 Hz, 2 H), 7.21 (d, J = 7.9 Hz, 1 H), 4.79 (br. s., 2 H), 2.43 (s, 3 H), 2.38 (s, 3 H). | Intermediate 4 |
| Example 15 | N-((6-methylpyridin-3-yl)methyl)-6-(5-methylthiophen-2-yl)pyrido[2,3-d]pyrimidin-4-amine 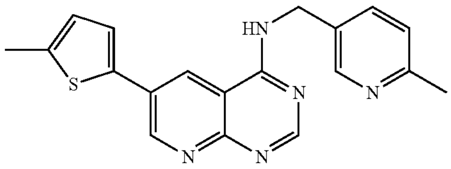 | LCMS (Method 4.1): 0.42 min, m/z 347.9 [M + H]+, CSH 2 min. 1H NMR (400 MHz, DMSO-d6) δ ppm 9.21-9.35 (m, 1 H), 9.10-9.20 (t, 1 H), 8.85 (d, J = 2.63 Hz, 1 H), 8.57 (s, 1 H), 8.45-8.53 (m, 1 H), 7.62-7.74 (m, 1 H), 7.48-7.62 (m, 1 H), 7.21 (d, J = 7.89 Hz, 1 H), 6.83-6.98 (m, 1 H), 4.78 (d, J = 5.70 Hz, 2 H), 2.52 (s, 3 H), 2.44 (s, 3 H). | Intermediate 4 |
| Example 16 | 6-(4-fluorophenyl)-N-((6-methylpyridin-3-yl)methyl)pyrido[2,3-d]pyrimidin-4-amine 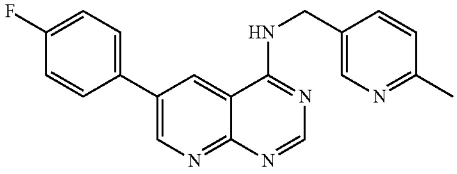 | LCMS (Method 4.2): 0.39 min, m/z 345.9 [M + 1]+, 1H NMR (400 MHz, DMSO-d6) δ ppm 9.34 (d, J = 2.19 Hz, 1 H), 9.15 (t, J = 1.00 Hz, 1 H), 9.04 (d, J = 2.19 Hz, 1 H), 8.62 (s, 1 H), 8.51 (d, J = 1.75 Hz, 1 H), 7.93 (dd, J = 8.77, 5.26 Hz, 2 H), 7.69 (br d, J = 2.19 Hz, 1 H), 7.41 (t, J = 8.77 Hz, 2 H), 7.21 (d, J = 7.89 Hz, 1 H), 4.79 (d, J = 5.26 Hz, 2 H), 2.44 (s, 3 H). | Intermediate 4 |
| Example 17 | 2-(4-(((6-methylpyridin-3-yl)methyl)amino)pyrido[2,3-d]pyrimidin-6-yl)benzonitrile 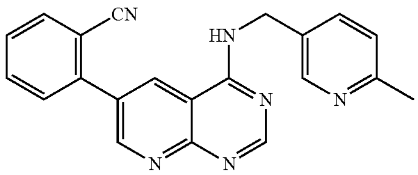 | LCMS (Method 4.1): 0.33 min, m/z 352.9 [M + H]+,. 1H NMR (400 MHz, DMSO-d6) δ ppm 9.15-9.20 (m, 2 H), 9.02 (d, J = 2.2 Hz, 1 H), 8.68 (s, 1 H), 8.49 (d, J = 2.2 Hz, 1 H), 8.01-8.10 (m, 1 H), 7.89 (d, J = 0.9 Hz, 1 H), 7.82 (s, 1 H), 7.68 (d, J = 7.9 Hz, 2 H), 7.20 (d, J = 7.9 Hz, 1 H), 4.78 (d, J = 5.3 Hz, 2 H), 2.43 (s, 3 H). | Intermediate 4 |

-continued

| Example No. | Chemical Name Structure | Analytical data $^1H$ NMR LC-MS | Starting Intermediate |
|---|---|---|---|
| Example 18 | 2-(4-(((6-methylpyridin-3-yl)methyl)amino)pyrido[2,3-d]pyrimidin-6-yl)benzamide 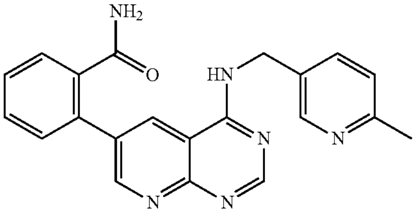 | LCMS (Method 4.1):: 0.14 min (solvent front) and 0.28 min, m/z 371.0 [M + H]+, 1H NMR (400 MHz, DMSO-d6) δ ppm 9.11-9.21 (bs, 1 H), 8.92 (d, J = 2.6 Hz, 1 H), 8.78 (d, J = 2.2 Hz, 1 H), 8.62 (s, 1 H), 8.49 (d, J = 1.8 Hz, 1 H), 7.78 (bs, 1 H), 7.68 (dd, J = 7.9, 2.2 Hz, 1 H), 7.56-7.65 (m, 4 H), 7.41 (bs, 1 H), 7.20 (d, J = 7.9 Hz, 1 H), 4.76 (br. s., 2 H), 2.43 (s, 3 H). | Intermediate 4 |

Example 19

N-((3,5-difluoropyridin-2-yl)methyl)-6-(4-fluorophenyl)pyrido[2,3-d]pyrimidin-4-amine

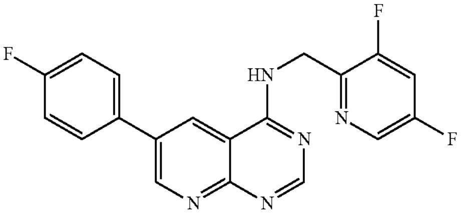 [SMILES: Fc1ccc(-c2cnc3ncnc(NCc4ncc(F)cc4F)c3c2)cc1]

DIPEA (0.15 mL, 0.861 mmol) was added to a mixture of 6-bromo-4-chloropyrido[2,3-d]pyrimidine (100 mg, 0.409 mmol) and (3,5-difluoropyridin-2-yl)methanamine hydrochloride (73.9 mg, 0.409 mmol) in DMF (Volume: 2 ml). Stirring went on for 6 h at 80° C. Upon completion of conversion of starting materials to 6-bromo-N-((3,5-difluoropyridin-2-yl)methyl)pyrido[2,3-d]pyrimidin-4-amine, water (1 mL) was added to the reaction mixture followed by 4-fluorophenylboronic acid (86 mg, 0.614 mmol), potassium phosphate (174 mg, 0.818 mmol) and Pd(dppf)$Cl_2$ $CH_2Cl_2$ (33.4 mg, 0.041 mmol). Stirring went on for 16 h at 80° C. The mixture was allowed to cool down to rt, then formic acid (0.154 mL, 4.09 mmol) was added. Purification by RP chromatography (Biotage Isolera, 30 g C18 cartridge, gradient elution from 100:0 to 30:70 A/B, A: water/acetonitrile 95:5+0.1% HCOOH, B: acetonitrile:water 95:5+0.1% HCOOH in 15 CV) yielded N-((3,5-difluoropyridin-2-yl)methyl)-6-(4-fluorophenyl)pyrido[2,3-d]pyrimidin-4-amine (35.8 mg, 0.097 mmol, 23.83% yield) as an off-white powder.

LCMS: 0.70 min, m/z 367.9 [M+H]+, (Method 4.1):

1H NMR (400 MHz, DMSO-d6) δ ppm 9.29-9.47 (m, 1H), 9.20 (t, 1H), 9.10 (d, J=2.41 Hz, 1H), 8.54-8.63 (m, 1H), 8.38-8.49 (m, 1H), 7.81-8.04 (m, 3H), 7.42 (t, J=8.88 Hz, 2H), 4.93-5.03 (m, 2H).

The following examples were synthesised via adaptations of the same procedure by using appropriate amines and boronic acids or esters and starting from 6-bromo-4-chloropyrido[2,3-d]pyrimidine.

| Example No. | Chemical Name Structure | Analytical data $^1H$ NMR LC-MS |
|---|---|---|
| Example 20 | 6-(4-fluorophenyl)-N-((6-methylpyridazin-3-yl)methyl)pyrido[2,3-d]pyrimidin-4-amine 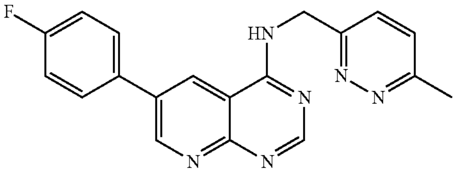 | LCMS (Method 4.1): 0.53 min, m/z 346.7 [M + H]+, 1H NMR (400 MHz, DMSO-d6) δ ppm 9.34-9.40 (m, 2 H), 9.10 (d, J = 2.6 Hz, 1 H), 8.59 (s, 1 H), 7.85-8.01 (m, 2H), 7.47-7.65 (m, 2 H), 7.42 (t, J = 9.0 Hz, 2 H), 5.05 (d, J = 4.8 Hz, 2 H), 2.59 (s, 3 H). |

Intermediate 8

6-Bromopyrido[2,3-d]pyrimidine-2,4-diol

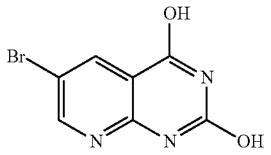

2-Amino-5-bromo-pyridine-3-carboxylic acid (3 g, 13.82 mmol) was finely ground with urea (4.90 g, 81.59 mmol). The mixture was heated to the point of evaporation of urea (280° C.) using a sand bath until its solidification. After cooling, the obtained solid was dissolved in 50 mL of 2 N sodium hydroxide and then filtered while hot. 6 N HCl solution was added dropwise into the mixture until a pH of 8. The resulting precipitate was filtered off, washed with cold water and dried in vacuo to give the title compound (3.0 g, 89.5%).

LCMS (Method 4): [MH+]=242.0 at 2.58 min.

Intermediate 9

6-Bromo-2,4-dichloropyrido[2,3-d]pyrimidine

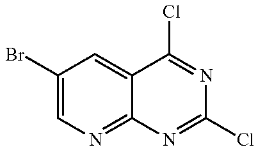 [SMILES: Clc1nc(Cl)c2cc(Br)cnc2n1]

To a suspension of 6-bromopyrido[2,3-d]pyrimidine-2,4-diol (Intermediate 8) (500 mg, 2.07 mmol) in $POCl_3$ (5 mL, 53.65 mmol) was added N,N-diisopropylethylamine (1.0 mL, 5.74 mmol). The mixture was heated to 120° C. for 18 hours. The reaction mixture was poured onto ice, diluted with dichloromethane (15 mL) and stirred at room temperature for one hour. The aqueous phase was extracted with dichloromethane (2×70 mL). The organic phases were combined, washed with a saturated aqueous solution of $NaHCO_3$, dried over $MgSO_4$ and filtered. The solvent was removed in vacuo to give the title compound (470 mg, 82%) as a red solid.

LCMS (Method 4): [MH+]=278.0 at 4.30 min.

Intermediate 10

1-(4-(6-Bromo-4-(((6-methylpyridazin-3-yl)methyl)amino)pyrido[2,3-d]pyrimidin-2-yl)piperazin-1-yl)ethan-1-one

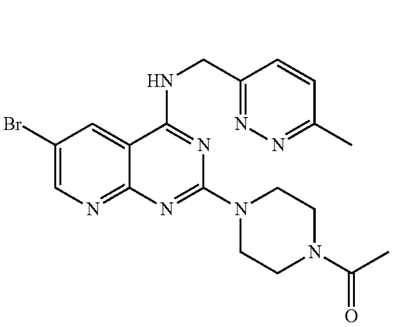 [SMILES: CC(=O)N1CCN(c2nc(NCc3ccc(C)nn3)c3cc(Br)cnc3n2)CC1]

Step 1: Preparation of 6-bromo-2-chloro-N-((6-methylpyridazin-3-yl)methyl)pyrido[2,3-d]pyrimidin-4-amine

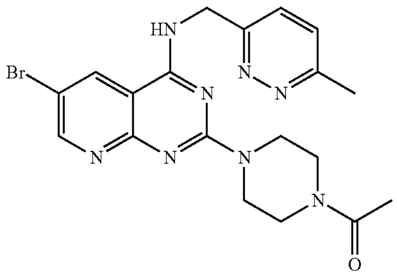 [SMILES: CC(=O)N1CCN(c2nc(NCc3ccc(C)nn3)c3cc(Br)cnc3n2)CC1]

To a solution of 6-bromo-2,4-dichloropyrido[2,3-d]pyrimidine (Intermediate 9) (370 mg, 1.33 mmol) and 6-methylpyridazin-3-yl)methanamine dihydrochloride (312 mg, 1.59 mmol) in tert-butanol (10 mL) was added N,N-diisopropylethylamine (0.69 mL, 3.98 mmol). The reaction mixture was heated to 40° C. for one hour. The solvent was removed in vacuo and the residue was taken on to the next step without further purification.

LCMS (Method 3): [MH+]=365.0 at 2.95 min.

Step 2: Preparation of 1-(4-(6-bromo-4-(((6-methylpyridazin-3-yl)methyl)amino)pyrido[2,3-d]pyrimidin-2-yl)piperazin-1-yl)ethan-1-one (Intermediate 10)

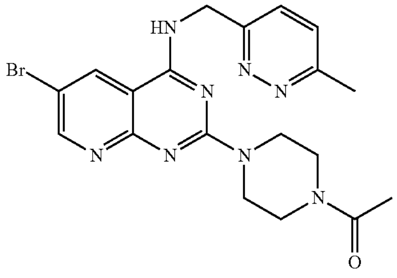 [SMILES: CC(=O)N1CCN(c2nc(NCc3ccc(C)nn3)c3cc(Br)cnc3n2)CC1]

6-Bromo-2-chloro-N-((6-methylpyridazin-3-yl)methyl)pyrido[2,3-d]pyrimidin-4-amine (485 mg, 1.33 mmol), 1-acetylpiperazine (340 mg, 2.65 mmol) and N,N-diisopropylethylamine (1.2 mL, 6.63 mmol) were dissolved in 1-butanol (10 mL). The reaction mixture was heated to 140° C. for one hour. The reaction was cooled down to room temperature, diluted with dichloromethane (20 mL) and washed with water (50 mL). The organic phase was dried over $MgSO_4$, filtered and the solvent was removed in vacuo to give the title compound (350 mg, 58%) as a red solid.

LCMS (Method 3): [MH+]=457.0 at 2.86 min.

Example 21 and 22

1-(4-(6-(4-fluorophenyl)-4-(((6-methylpyridazin-3-yl)methyl)amino)pyrido[2,3-d]pyrimidin-2-yl)piperazin-1-yl)ethan-1-one (Ex. 21) and 1-(4-(4-(((6-methylpyridazin-3-yl)methyl)amino)pyrido[2,3-d]pyrimidin-2-yl)piperazin-1-yl)ethan-1-one (Ex. 22)

Example 21

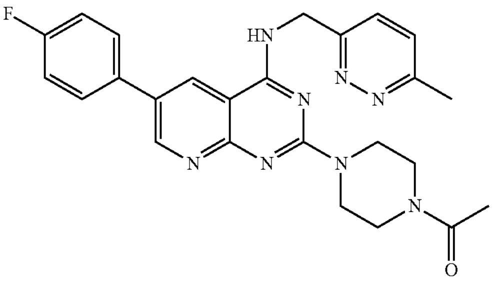

Example 22

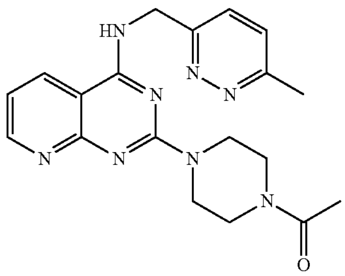

1-(4-(6-Bromo-4-(((6-methylpyridazin-3-yl)methyl)amino)pyrido[2,3-d]pyrimidin-2-yl)piperazin-1-yl)ethan-1-one (Intermediate 10) (50 mg, 0.11 mmol), potassium carbonate (45 mg, 0.33 mmol), 4-fluorophenylboronic acid (17 mg, 0.12 mmol) and [1,1'-bis(diphenylphosphino)ferrocene] dichloropalladium(II) (8 mg, 0.01 mmol) were placed in a microwave vial. 1,4-Dioxane (2 mL) and water (0.5 mL) were added and the solution was degassed with nitrogen for 10 minutes. The reaction mixture was heated to 110° C. for 20 minutes in a microwave reactor. After return to room temperature, water (2 mL) was added and the mixture was extracted with ethyl acetate (2×20 mL). The organic phase were combined, dried over $MgSO_4$, filtered and the solvent was removed in vacuo. The residue was purified by preparative HPLC to give the title compounds.

Example 21 (18 mg, 35%)

$^1H$ NMR (400 MHz, $CDCl_3$): δ 9.00 (d, J=2.5 Hz, 1H), 8.14 (d, J=2.5 Hz, 1H), 7.61-7.56 (m, 3H), 7.47 (d, J=8.5 Hz, 1H), 7.40 (d, J=8.5 Hz, 1H), 7.20-7.15 (m, 2H), 5.03 (d, J=4.4 Hz, 2H), 4.07 (dd, J=3.7, 5.5 Hz, 2H), 3.99 (dd, J=3.4, 5.8 Hz, 2H), 3.71 (dd, J=5.3, 5.3 Hz, 2H), 3.55 (dd, J=5.2, 5.2 Hz, 2H), 2.76 (s, 3H), 2.17 (s, 3H). LCMS (Method 3): [MH+]=473.0 at 3.4 min.

Example 22 (9.0 mg, 21%)

$^1H$ NMR (400 MHz, $CDCl_3$): δ 8.79 (d, J=3.3 Hz, 1H), 8.07 (d, J=8.1 Hz, 1H), 7.47-7.38 (m, 3H), 7.07 (dd, J=4.8, 8.1 Hz, 1H), 5.00 (d, J=3.8 Hz, 2H), 4.05 (t, J=6.2 Hz, 2H), 3.99 (t, J=4.5 Hz, 2H), 3.72-3.68 (m, 2H), 3.54 (dd, J=4.5, 4.5 Hz, 2H), 2.75 (s, 3H), 2.16 (s, 3H). LCMS (Method 3): [MH+]=379.0 at 2.36 min.

Example 23

1-(4-(4-(((6-Methylpyridazin-3-yl)methyl)amino)-6-(5-methylthiazol-2-yl)pyrido[2,3-d]pyrimidin-2-yl)piperazin-1-yl)ethan-1-one

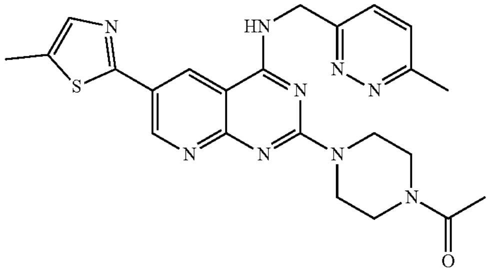 [SMILES: CC(=O)N1CCN(c2nc(NCc3ccc(C)nn3)c3cc(-c4ncc(C)s4)cnc3n2)CC1]

Nitrogen gas was bubbled for 5 min through a mixture of 1-(4-(6-bromo-4-(((6-methylpyridazin-3-yl)methyl)amino)pyrido[2,3-d]pyrimidin-2-yl)piperazin-1-yl)ethan-1-one (Intermediate 10) (50 mg, 0.109 mmol), 5-methyl-2-(tri-n-butylstannyl)thiazole (0.077 mL, 0.219 mmol) and tetrakis(triphenylphosphine)palladium(0) (19 mg, 0.0164 mmol) in N,N-dimethylformamide (2 mL). The mixture was heated to 80° C. for 18 hours. After return to room temperature, the reaction was diluted in methanol (5 mL) and loaded onto an SCX cartridge. The cartridge was washed with methanol and the filtrate was collected when eluting with a 7M solution of ammonia in methanol. The solvent was removed in vacuo and the residue was purified by preparative HPLC to give the title compound (15 mg, 29%) as an off-white solid.

$^1H$ NMR (400 MHz, $CDCl_3$): δ 9.21 (d, J=2.4 Hz, 1H), 8.56 (d, J=2.3 Hz, 1H), 7.51 (d, J=1.0 Hz, 1H), 7.44 (d, J=8.5 Hz, 1H), 7.36 (d, J=8.7 Hz, 1H), 5.04 (d, J=4.8 Hz, 2H), 4.03-4.03 (m, 2H), 3.97-3.96 (m, 2H), 3.69 (dd, J=5.1, 5.1 Hz, 2H), 3.53 (dd, J=5.1, 5.1 Hz, 2H), 2.75 (s, 3H), 2.54 (s, 3H), 2.16 (s, 3H). LCMS (Method 3): [MH+]=476.0 at 3.06 min.

The following compounds were synthesised following the procedure described for the preparation of 1-(4-(4-(((6-Methylpyridazin-3-yl)methyl)amino)-6-(5-methylthiazol-2-yl)pyrido[2,3-d]pyrimidin-2-yl)piperazin-1-yl)ethan-1-one:

| Example No. | Chemical Name Structure | Analytical data $^1H$ NMR LC-MS |
|---|---|---|
| Example 24 | 1-(4-(4-(((6-Methylpyridazin-3-yl)methyl)amino)-6-(5-methylpyridin-2-yl)pyrido[2,3-d]pyrimidin-2-yl)piperazin-1-yl)ethan-1-one 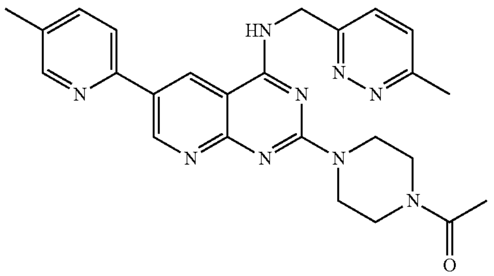 | $^1H$ NMR (400 MHz, $CDCl_3$): δ 9.00 (d, J = 2.5 Hz, 1 H), 8.14 (d, J = 2.5 Hz, 1 H), 7.61-7.56 (m, 3 H), 7.47 (d, J = 8.5 Hz, 1 H), 7.40 (d, J = 8.5 Hz, 1 H), 7.20-7.15 (m, 2 H), 5.03 (d, J = 4.4 Hz, 2 H), 4.07 (dd, J = 3.7, 5.5 Hz, 2 H), 3.99 (dd, J = 3.4, 5.8 Hz, 2 H), 3.71 (dd, J = 5.3, 5.3 Hz, 2 H), 3.55 (dd, J = 5.2, 5.2 Hz, 2 H), 2.76 (s, 3 H), 2.17 (s, 3 H). LCMS (Method 4): [MH+] = 470.0 at 2.40 min. |
| Example 25 | 1-(4-(6-Methyl-4-(((6-methylpyridazin-3-yl)methyl)amino)pyrido[2,3-d]pyrimidin-2-yl)piperazin-1-yl)ethan-1-one 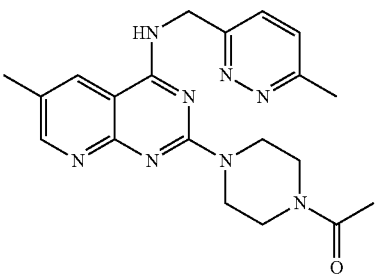 | $^1H$ NMR (400 MHz, $CDCl_3$): δ 8.66 (d, J = 1.3 Hz, 1 H), 7.85 (s, 1 H), 7.44 (d, J = 8.3 Hz, 1 H), 7.38 (d, J = 8.3 Hz, 2 H), 5.00 (d, J = 4.3 Hz, 2 H), 4.03 (t, J = 5.2 Hz, 2 H), 3.97 (t, J = 5.0 Hz, 2 H), 3.70 (dd, J = 5.2, 5.2 Hz, 2 H), 3.53 (dd, J = 5.1, 5.1 Hz, 2 H), 2.76 (s, 3 H), 2.41 (s, 3 H), 2.16 (s, 3 H). LCMS (Method 4): [MH+] = 393.0 at 1.99 min. |

Intermediate 25

N-[1-(3-cyclopropyl-1,2,4-oxadiazol-5-yl)ethyl]-6-(4-fluorophenyl)pyrido[2,3-d]pyrimidin-4-amine

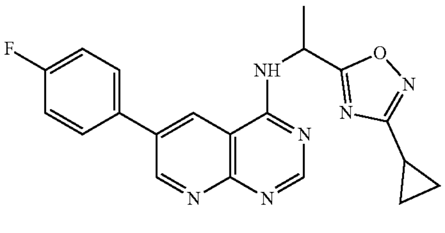 [SMILES: CC(Nc1ncnc2ncc(-c3ccc(F)cc3)cc12)c1nc(C2CC2)no1]

6-(4-Fluorophenyl)pyrido[2,3-d]pyrimidin-4(3H)-one (200 mg, 0.83 mmol) was suspended in thionyl chloride (1.2 mL, 16.6 mmol) and DMF (0.6 μL, 0.008 mmol). The reaction mixture was heated at 95° C. for 16 hours and cooled to room temperature. The solvent was removed in vacuo. The resulting residue was suspended in dioxane (5.0 mL) and then DIPEA (0.72 mL, 4.15 mmol) and [1-(3-cyclopropyl-1,2,4-oxadiazol-5-yl)ethyl]amine hydrochloride (236 mg, 1.24 mmol) were added. The reaction mixture was heated at 95° C. for 3 hours and then cooled to room temperature. Water was added, and the resulting solid was filtered and dried in vacuo. The residue was purified by preparative HPLC to give the title compound (257 mg, 82%) as an off-white solid as a mixture of two enantiomers.

$^1H$ NMR (400 MHz, DMSO): δ 9.47-9.43 (m, 1H), 9.19-9.16 (m, 2H), 8.68 (s, 1H), 8.05-7.98 (m, 2H), 7.53-7.45 (m, 2H), 5.86-5.79 (m, 1H), 2.20-2.12 (m, 1H), 1.76 (d, J=6.8 Hz, 3H), 1.10 (d, J=8.4 Hz, 2H), 0.95-0.87 (m, 2H). LCMS (Method 3): [MH+]=377 at 4.09 min.

The following compounds were synthesised following the procedure described for the preparation of N-[1-(3-cyclopropyl-1,2,4-oxadiazol-5-yl)ethyl]-6-(4-fluorophenyl)-pyrido-[2,3-d]pyrimidin-4-amine:

| Example No. | Chemical Name<br>Structure | Analytical data<br>$^1H$ NMR<br>LC-MS |
|---|---|---|
| Example 65 | 6-(5-methylpyridin-2-yl)-N-((3-(trifluoromethyl)-1,2,4-oxadiazol-5-yl)methyl)pyrido[2,3-d]pyrimidin-4-amine<br>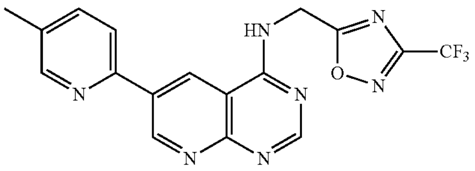 | $^1H$ NMR (400 MHz, DMSO) δ 9.79-9.73 (m, 2 H), 9.45-9.42 (m, 1 H), 8.64 (s, 2 H), 8.12 (d, J = 7.8 Hz, 1 H), 7.88 (d, J = 7.4 Hz, 1 H), 5.22 (d, J = 4.5 Hz, 2 H), 2.41 (s, 3 H). LCMS (Method 3): [$MH^+$] = 388 at 3.83 min. |
| Example 66 | (6-(5-Fluoro-2-pyridyl)-N-[(1R)-1-(3-methyl-1,2,4-oxadiazol-5-yl)ethyl]pyrido[2,3-d]pyrimidin-4-amine<br>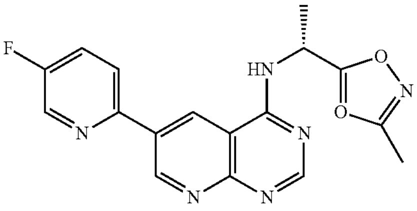 | $^1H$ NMR (400 MHz, DMSO): δ 9.78-9.70 (m, 1 H), 9.50 (s, 1 H), 9.36 (d, J = 5.8 Hz, 1 H), 8.82 (s, 1 H), 8.68 (s, 1 H), 8.36-8.26 (m, 1 H), 8.04 (dd, J = 9.0, 9.0 Hz, 1 H), 5.85 (dd, J = 6.3, 6.3 Hz, 1 H), 2.37 (s, 3 H), 1.79 (d, J = 6.4 Hz, 3 H). LCMS (Method 4): [$MH^+$] = 352 at 2.75 min. Chiral analysis (Method 22) at 3.61 min. |
| Example 67 | (R)-6-(5-fluoropyridin-2-yl)-N-(1-(2-(trifluoromethyl)pyrimidin-5-yl)ethyl)pyrido[2,3-d]pyrimidin-4-amine<br>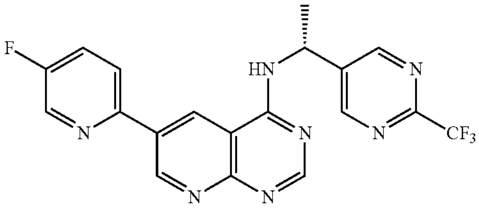 | $^1H$ NMR (400 MHz, DMSO): δ 9.68 (s, 1 H), 9.47 (s, 1 H), 9.21 (s, 2 H), 9.14 (d, J = 6.4 Hz, 1 H), 8.80 (d, J = 1.5 Hz, 1 H), 8.62 (s, 1 H), 8.30 (dd, J = 4.1, 8.3 Hz, 1 H), 8.05-8.00 (m, 1 H), 5.70 (dd, J = 6.7, 6.7 Hz, 1 H), 1.76 (d, J = 6.8 Hz, 3 H). LCMS (Method 4): [$MH^+$] = 416 at 3.35 min. Chiral analysis (Method 17) at 2.6 min. |
| Example 68 | N-[(1R)-1-(3-methyl-1,2,4-oxadiazol-5-yl)ethyl]-6-(5-methylpyrimidin-2-yl)pyrido[2,3-d]pyrimidin-4-amine<br>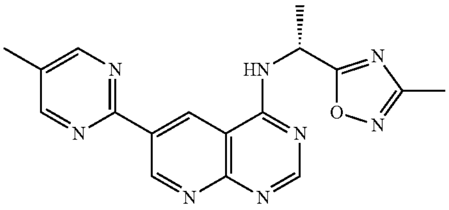 | $^1H$ NMR (400 MHz, DMSO): δ 9.93 (d, J = 2.4 Hz, 1 H), 9.77 (d, J = 2.3 Hz, 1 H), 9.59 (d, J = 6.4 Hz, 1 H), 8.89 (s, 2 H), 8.67 (s, 1 H), 5.86-5.81 (m, 1 H), 2.39 (s, 3 H), 2.34 (s, 3 H), 1.75 (d, J = 7.2 Hz, 3 H). LCMS (Method 4): [$MH^+$] = 349 at 2.65 min. Chiral analysis (Method 25) at 1.89 min. |

-continued

| Example No. | Chemical Name<br>Structure | Analytical data<br>$^1$H NMR<br>LC-MS |
|---|---|---|
| Example 69 | 6-(4-fluorophenyl)-N-[(1R)-1-[6-(trifluoromethyl)pyridazin-3-yl]ethyl]pyrido[2,3-d]pyrimidin-4-amine<br>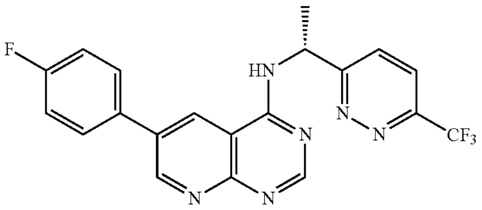 | $^1$H NMR (400 MHz, DMSO) d 9.39 (d, J = 2.4 Hz, 1 H), 9.25 (d, J = 2.5 Hz, 1 H), 9.14 (d, J = 6.8 Hz, 1 H), 8.54 (s, 1 H), 8.22 (d, J = 8.8 Hz, 1 H), 8.11 (d, J = 8.9 Hz, 1 H), 8.00 (ddd, J = 3.2, 5.3, 12.1 Hz, 2 H), 7.46 (dd, J = 8.9, 8.9 Hz, 2 H), 5.90-5.85 (m, 1 H), 1.80 (d, J = 7.2 Hz, 3 H). LCMS (Method 4): $[MH^+]$ = 415 at 3.54 min. Chiral analysis (Method 5) at 1.64 min. |
| Example 70 | 6-(5-fluoropyridin-2-yl)-N-((3-(trifluoromethyl)-1,2,4-oxadiazol-5-yl)methyl)pyrido[2,3-d]pyrimidin-4-Amine<br>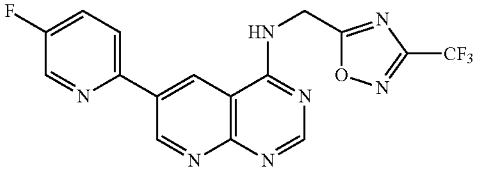 | $^1$H NMR (400 MHz, DMSO): δ 9.75 (d, J = 2.4 Hz, 2 H), 9.44 (d, J = 2.4 Hz, 1 H), 8.81 (d, J = 2.9 Hz, 1 H), 8.66 (s, 1 H), 8.29 (dd, J = 4.3, 8.8 Hz, 1 H), 8.06-8.00 (m, 1 H), 5.23 (d, J = 5.4 Hz, 2 H). LCMS (Method 4): $[MH^+]$ = 392 at 3.59 min. |
| Example 71 | N-[(5-methyl-1,2,4-oxadiazol-3-yl)methyl]-6-(5-methylthiazol-2-yl)pyrido[2,3-d]pyrimidin-4-amine<br>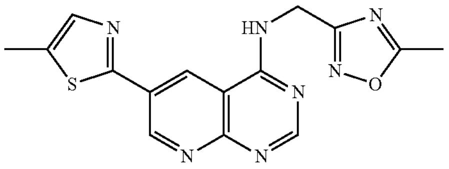 | $^1$H NMR (400 MHz, DMSO): δ 9.58 (t, J = 5.3 Hz, 1 H), 9.52 (d, J = 2.4 Hz, 1 H), 9.24 (d, J = 2.4 Hz, 1 H), 8.65 (s, 1 H), 7.76 (d, J = 1.3 Hz, 1 H), 4.91 (d, J = 5.4 Hz, 2 H), 2.59 (s, 3 H), 2.58 (d, J = 1.2 Hz, 3 H). LCMS (Method 4): $[MH^+]$ = 340 at 2.55 min. |
| Example 72 | N-[(5-methyl-1,3,4-oxadiazol-2-yl)methyl]-6-(5-methylthiazol-2-yl)pyrido[2,3-d]pyrimidin-4-amine<br>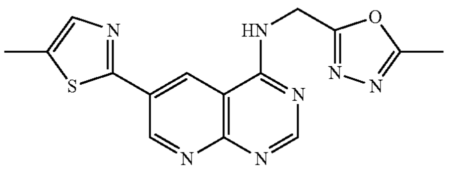 | $^1$H NMR (400 MHz, DMSO): δ 9.67 (s, 1 H), 9.53 (d, J = 2.4 Hz, 1 H), 9.23 (d, J = 2.4 Hz, 1 H), 8.68 (s, 1 H), 7.76 (d, J = 1.3 Hz, 1 H), 5.01 (d, J = 4.1 Hz, 2 H), 2.58 (d, J = 1.1 Hz, 3 H), 2.49 (s, 3 H). LCMS (Method 4): $[MH^+]$ = 340 at 2.39 min. |
| Example 73 | 6-(4-fluorophenyl)-N-[(5-methyl-1,3,4-oxadiazol-2-yl)methyl]pyrido[2,3-d]pyrimidin-4-amine<br>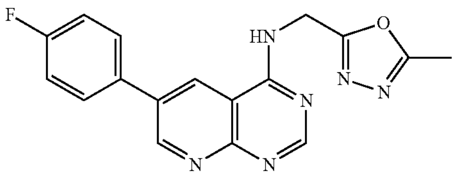 | $^1$H NMR (400 MHz, DMSO): δ 9.41 (d, J = 2.5 Hz, 1 H), 9.37 (t, J = 5.7 Hz, 1 H), 9.08 (d, J = 2.5 Hz, 1 H), 8.67 (s, 1 H), 7.98-7.94 (m, 2 H), 7.47-7.42 (m, 2 H), 5.03 (d, J = 5.5 Hz, 2 H), 2.49 (s, 3 H). LCMS (Method 4): $[MH^+]$ = 337 at 2.65 min. |

-continued

| Example No. | Chemical Name Structure | Analytical data $^1$H NMR LC-MS |
|---|---|---|
| Example 75 | 6-(5-methylthiazol-2-yl)-N-[(2-methylthiazol-4-yl)methyl]pyrido[2,3-d]pyrimidin-4-amine 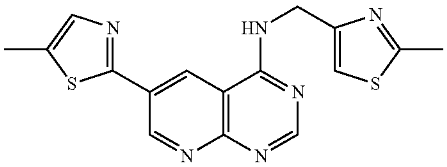 | $^1$H NMR (400 MHz, DMSO): δ 9.54-9.51 (m, 2 H), 9.30 (d, J = 2.3 Hz, 1 H), 8.68 (s, 1 H), 7.79 (d, J = 1.3 Hz, 1 H), 7.39 (s, 1 H), 4.89 (d, J = 5.6 Hz, 2 H), 2.70-2.69 (m, 3 H), 2.61 (d, J = 1.1 Hz, 3 H). LCMS (Method 3): [MH$^+$] = 337 at 3.64 min. |
| Example 76 | 6-(4-fluorophenyl)-N-[1-[3-(trifluoromethyl)-1,2,4-oxadiazol-5-yl]ethyl]pyrido[2,3-d]pyrimidin-4-amine 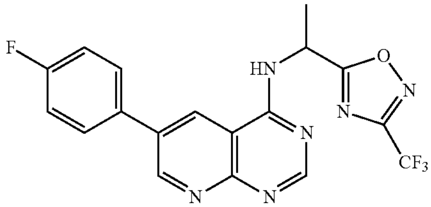 | $^1$H NMR (400 MHz, DMSO): δ 9.43 (d, J = 2.4 Hz, 1 H), 9.29 (d, J = 6.7 Hz, 1 H), 9.12 (d, J = 2.5 Hz, 1 H), 8.64 (s, 1 H), 8.00-7.94 (m, 2 H), 7.49-7.42 (m, 2 H), 5.94 (dq, J = 7.0, 7.0 Hz, 1 H), 1.83 (d, J = 7.2 Hz, 3 H). LCMS (Method 3): [MH$^+$] = 405 at 4.77 min. |
| Example 77 | 6-(4-fluorophenyl)-N-[(3-methylisoxazol-5-yl)methyl]pyrido[2,3-d]pyrimidin-4-amine 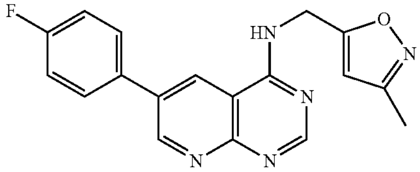 | $^1$H NMR (400 MHz, DMSO): δ 9.45 (s, 1 H), 9.34-9.30 (m, 1 H), 9.11 (s, 1 H), 8.71 (s, 1 H), 8.04-7.96 (m, 2 H), 7.48 (t, J = 8.5 Hz, 2 H), 6.37 (s, 1 H), 4.97 (d, J = 5.0 Hz, 2 H), 2.24 (s, 3 H). LCMS (Method 3): [MH$^+$] = 336 at 4.02 min. |
| Example 78 | N-[(5-methyl-1,3,4-thiadiazol-2-yl)methyl]-6-(5-methylthiazol-2-yl)pyrido[2,3-d]pyrimidin-4-amine 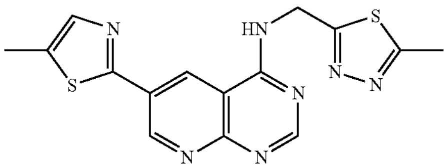 | $^1$H NMR (400 MHz, DMSO): δ 9.84-9.79 (m, 1 H), 9.53 (d, J = 2.3 Hz, 1 H), 9.19 (d, J = 2.5 Hz, 1 H), 8.73 (s, 1 H), 7.77-7.75 (m, 1 H), 5.13 (d, J = 4.3 Hz, 2 H), 2.67 (s, 3 H), 2.57 (d, J = 1.1 Hz, 3 H). LCMS (Method 3): [MH$^+$] = 356 at 3.29 min. |
| Example 79 | 6-(4-fluorophenyl)-N-[(2-methylthiazol-4-yl)methyl]pyrido[2,3-d]pyrimidin-4-amine 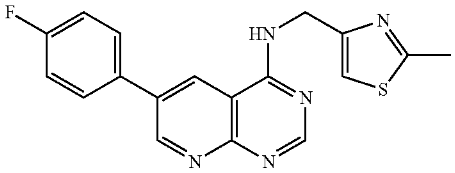 | $^1$H NMR (400 MHz, DMSO): δ 9.41-9.40 (m, 1 H), 9.26-9.24 (m, 1 H), 9.16 (s, 1 H), 8.68-8.66 (m, 1 H), 8.02-7.98 (m, 2 H), 7.49-7.45 (m, 2 H), 7.39 (s, 1 H), 4.91-4.90 (m, 2 H), 2.68 (s, 3 H). LCMS (Method 3): [MH+] = 352 at 3.65 min. |

-continued

| Example No. | Chemical Name<br>Structure | Analytical data<br>$^1$H NMR<br>LC-MS |
|---|---|---|
| Example 80 | 6-(4-fluorophenyl)-N-[(5-methyl-1,2,4-oxadiazol-3-yl)methyl]pyrido[2,3-d]pyrimidin-4-amine<br>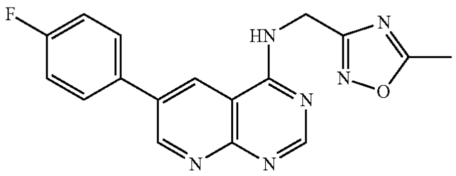 | $^1$H NMR (400 MHz, DMSO): δ 9.43 (d, J = 2.4 Hz, 1 H), 9.35-9.33 (m, 1 H), 9.13 (d, J = 2.4 Hz, 1 H), 8.68 (s, 1 H), 8.02-7.98 (m, 2 H), 7.50-7.46 (m, 2 H), 4.97-4.95 (m, 2 H), 2.72 (s, 3H). LCMS (Method 3): [MH+] = 337 at 3.33 min. |
| Example 82 | N-[(3-methylisoxazol-5-yl)methyl]-6-(5-methylthiazol-2-yl)pyrido[2,3-d]pyrimidin-4-amine<br>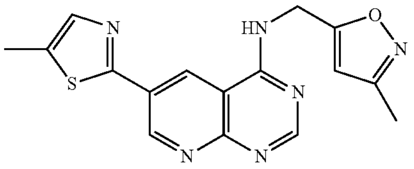 | $^1$H NMR (400 MHz, DMSO): δ 9.51-9.50 (m, 2 H), 9.21 (d, J = 2.4 Hz, 1 H), 8.68 (s, 1 H), 7.76 (s, 1 H), 6.32 (s, 1 H), 4.91-4.90 (m, 2 H), 2.57 (s, 3 H), 2.20 (s, 3 H). LCMS (Method 3): [MH+] = 339 at 3.67 min. |

Example 83

Single enantiomer 1 of 6-(5-fluoro-2-pyridyl)-N-[1-(5-methyl-1,3,4-thiadiazol-2-yl)ethyl]pyrido[2,3-d]pyrimidin-4-amine

Example 84

Single enantiomer 2 of 6-(5-fluoro-2-pyridyl)-N-[1-(5-methyl-1,3,4-thiadiazol-2-yl)ethyl]pyrido[2,3-d]pyrimidin-4-amine

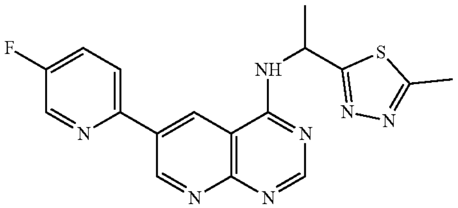 [SMILES: Cc1nnc(C(C)Nc2ncnc3ncc(-c4ccc(F)cn4)cc23)s1]

6-(5-Fluoropyridin-2-yl)pyrido[2,3-d]pyrimidin-4(3H)-one (200 mg, 0.64 mmol) was suspended in thionyl chloride (1.2 mL, 16.5 mmol) and DMF (0.001 mL). The reaction mixture was heated at 95° C. for 22 hours. The reaction was cooled to room temperature and the solvent was removed in vacuo. The resulting residue was diluted with saturated $NaHCO_3$ solution and the aqueous phase was extracted with ethyl acetate (2×50 mL). The combined organic phases were dried, and the solvent was removed in vacuo. The residue (145 mg) was dissolved in chloroform (1.0 mL) and 1-(5-methyl-1,3,4-thiadiazol-2-yl)ethan-1-amine (93 mg, 0.65 mmol) was added. The reaction mixture was heated in a sealed tube under nitrogen for 18 hours at 70° C. After this time the resulting mixture was cooled to room temperature. The reaction was diluted with cold water and stirred for 10 minutes. The solid was collected by filtration and then ethyl acetate and water were added. The two phases were separated, and the aqueous phase was extracted with 5% methanol in ethyl acetate (2×50 mL). The combined organic phases were passed through phase separating paper and the solvent was removed in vacuo. The residue was purified by achiral preparative HPLC, followed by chiral preparative SFC to give the title compounds as off-white solids.

Example 83, single enantiomer 1: 24.7 mg, 13%

$^1$H NMR (400 MHz, DMSO): δ 9.71 (d, J=2.4 Hz, 1H), 9.47 (d, J=2.4 Hz, 1H), 9.35 (d, J=7.4 Hz, 1H), 8.80 (d, J=3.0 Hz, 1H), 8.70 (s, 1H), 8.28 (dd, J=4.3, 8.8 Hz, 1H), 8.05-7.99 (m, 1H), 6.02-5.97 (m, 1H), 2.67 (s, 3H), 1.82 (d, J=7.0 Hz, 3H).

LCMS (Method 4): [MH+]=368 at 2.60 min. Chiral analysis (Method 30) at 1.69 min.

Example 84, single enantiomer 2: 27.3 mg, 14%

$^1$H NMR (400 MHz, DMSO): δ 9.71 (d, J=2.4 Hz, 1H), 9.47 (d, J=2.5 Hz, 1H), 9.35 (d, J=7.5 Hz, 1H), 8.80 (d, J=2.9 Hz, 1H), 8.70 (s, 1H), 8.28 (dd, J=4.3, 8.8 Hz, 1H), 8.05-7.99 (m, 1H), 6.02-5.97 (m, 1H), 2.67 (s, 3H), 1.82 (d, J=7.0 Hz, 3H). LCMS (Method 4): [MH+]=368 at 2.60 min. Chiral analysis (Method 30) at 3.1 min.

The following compounds reported in the table below were obtained as single isomers by chiral preparative SFC purification following the same procedure described for the preparation of the single enantiomers of 6-(5-fluoro-2-pyridyl)-N-[1-(5-methyl-1,3,4-thiadiazol-2-yl)ethyl]pyrido[2,3-d]pyrimidin-4-amine:

| Example No. | Chemical Name<br>Structure | Analytical data<br>$^1$H NMR<br>LC-MS |
|---|---|---|
| Example 87 | Single enantiomer 1 of N-(1-(5-methyl-1,3,4-thiadiazol-2-yl)ethyl)-6-(5-methylpyridin-2-yl)pyrido[2,3-d]pyrimidin-4-amine<br>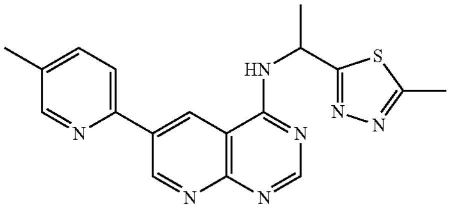 | $^1$H NMR (400 MHz, DMSO): δ 9.73 (d, J = 2.4 Hz, 1 H), 9.47 (d, J = 2.4 Hz, 1 H), 9.34 (d, J = 7.4 Hz, 1 H), 8.69 (s, 1 H), 8.63 (d, J = 1.9 Hz, 1 H), 8.11 (d, J = 8.2 Hz, 1 H), 7.86 (dd, J = 2.1, 8.2 Hz, 1 H), 6.02-5.96 (m, 1 H), 2.67 (s, 3 H), 2.41 (s, 3 H), 1.82 (d, J = 7.0 Hz, 3 H). LCMS (Method 3): [MH$^+$] = 364 at 3.59 min. Chiral analysis (Method 23) at 1.0 min. |
| Example 88 | Single enantiomer 2 of N-(1-(5-methyl-1,3,4-thiadiazol-2-yl)ethyl)-6-(5-methylpyridin-2-yl)pyrido[2,3-d]pyrimidin-4-amine<br>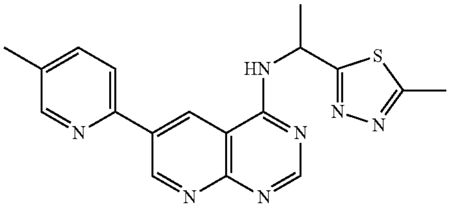 | $^1$H NMR (400 MHz, DMSO): δ 9.73 (d, J = 2.3 Hz, 1 H), 9.47 (d, J = 2.4 Hz, 1 H), 9.34 (d, J = 7.4 Hz, 1 H), 8.69 (s, 1 H), 8.63 (d, J = 1.9 Hz, 1 H), 8.11 (d, J = 8.2 Hz, 1 H), 7.86 (dd, J = 1.9, 8.2 Hz, 1 H), 6.02-5.96 (m, 1 H), 2.67 (s, 3 H), 2.41 (s, 3 H), 1.82 (d, J = 7.0 Hz, 3 H). LCMS (Method 3): [MH$^+$] = 364 at 3.59 min. Chiral analysis (Method 23) at 1.64 min. |

Example 91

6-(4-Fluorophenyl)-N-[(5-methyl-1,3,4-thiadiazol-2-yl)methyl]pyrido[2,3-d]pyrimidin-4-amine

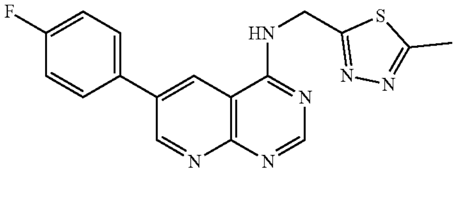 [SMILES: Cc1nnc(CNc2ncnc3ncc(-c4ccc(F)cc4)cc23)s1]

6-(4-Fluorophenyl)pyrido[2,3-d]pyrimidin-4(3H)-one (90 mg, 0.37 mmol) and DIPEA (0.32 ml, 1.87 mmol) were suspended in toluene (3.5 mL). The reaction mixture was heated at 95° C. and phosphorus(V) oxychloride (0.042 mL, 0.45 mmol) was added. The reaction was heated at 95° C. for 2 hours and then cooled to room temperature. The solvent was removed in vacuo and to the resulting residue was added (5-methyl-1,3,4-thiadiazol-2-yl)methanamine hydrochloride (93 mg, 0.56 mmol), DIPEA (0.32 mL, 1.87 mmol) and dioxane (3.5 mL). The reaction mixture was heated at 95° C. for an additional 5 hours. The reaction was diluted with water and the solid was collected. The precipitate was suspended in DMSO and filtered. The solid was washed with water, then with ethyl acetate and dried under vacuum to give the title compound (31 mg, 24%) as an off-white solid. $^1$H NMR (400 MHz, DMSO): δ 9.62-9.56 (m, 1H), 9.45 (d, J=1.7 Hz, 1H), 9.09 (s, 1H), 8.77 (s, 1H), 8.02-7.96 (m, 2H), 7.49 (t, J=8.6 Hz, 2H), 5.19 (d, J=5.2 Hz, 2H), 2.72 (s, 3H). LCMS (Method 4): [MH+]=353 at 2.78 min.

The following compounds were synthesised following the procedure described for the preparation of 6-(4-Fluorophenyl)-N-[(5-methyl-1,3,4-thiadiazol-2-yl)methyl]pyrido[2,3-d]pyrimidin-4-amine:

| Example No. | Chemical Name<br>Structure | Analytical data<br>$^1$H NMR<br>LC-MS |
|---|---|---|
| Example 92 | 6-(4-fluorophenyl)-N-[(3-methyl-1,2,4-oxadiazol-5-yl)methyl]pyrido[2,3-d]pyrimidin-4-amine<br>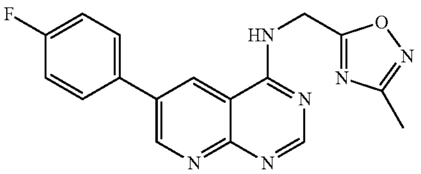 | $^1$H NMR (400 MHz, DMSO): δ 9.52 (t, J = 5.5 Hz, 1 H), 9.42 (d, J = 2.4 Hz, 1 H), 9.10 (d, J = 2.5 Hz, 1 H), 8.63 (s, 1 H), 8.00-7.94 (m, 2 H), 7.49-7.42 (m, 2 H), 5.07 (d, J = 5.6 Hz, 2 H), 2.33 (s, 3 H). LCMS (Method 3): [MH$^+$] = 337 at 3.36 min. |
| Example 93 | 6-(4-fluorophenyl)-N-[[3-(trifluoromethyl)-1,2,4-oxadiazol-5-yl]methyl]pyrido[2,3-d]pyrimidin-4-amine<br>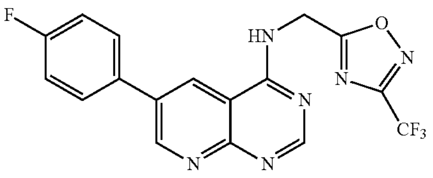 | $^1$H NMR (400 MHz, DMSO): δ 9.67-9.62 (m, 1 H), 9.44 (d, J = 2.4 Hz, 1 H), 9.11 (d, J = 2.5 Hz, 1 H), 8.63 (s, 1 H), 8.01-7.95 (m, 2 H), 7.49-7.42 (m, 2 H), 5.23 (d, J = 5.0 Hz, 2 H). LCMS (Method 4): [MH$^+$] = 391 at 3.84 min. |
| Example 94 | 6-(5-chloro-2-pyridyl)-N-[(1S)-1-[2-(trifluoromethyl)pyrimidin-5-yl]ethyl]pyrido[2,3-d]pyrimidin-4-amine<br>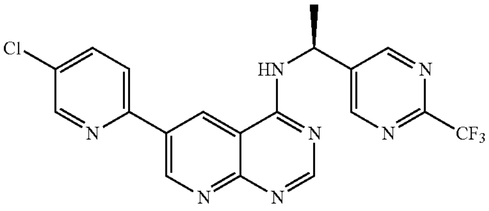 | $^1$H NMR (400 MHz, DMSO): δ 9.74 (d, J = 2.5 Hz, 1 H), 9.60 (d, J = 2.3 Hz, 1 H), 9.23 (d, J = 1 Hz, 1 H), 8.96 (d, J = 1.8 Hz, 1 H), 8.88 (d, J = 1.8 Hz, 1 H), 8.64 (s, 1 H), 8.27-8.18 (m, 2 H), 7.93 (d, J = 8.1 Hz, 1 H), 5.79-5.70 (m, 1 H), 1.76 (d, J = 7.1 Hz, 3 H). LCMS (Method 4): [MH+] = 432 at 3.73 min. Chiral analysis (Method 26) at 1.45 min. |
| Example 95 | 6-phenyl-N-[(1R)-1-[2-(trifluoromethyl)pyrimidin-5-yl]ethyl]pyrido[2,3-d]pyrimidin-4-amine<br>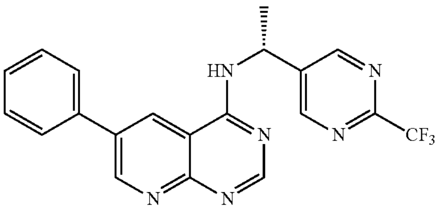 | $^1$H NMR (400 MHz, DMSO): δ 9.44 (d, J = 2.4 Hz, 1 H), 9.20 (s, 2 H), 9.18 (d, J = 2.4 Hz, 1 H), 9.01-8.98 (m, 1 H), 8.61 (s, 1 H), 7.97-7.95 (m, 2 H), 7.64-7.61 (m, 2 H), 7.51-7.48 (m, 1 H), 5.73-5.71 (m, 1 H), 1.74 (d, J = 7.1 Hz, 3 H). LCMS (Method 4): [MH+] = 397 at 3.57 min. Chiral analysis (Method 17) at 2.05 min. |

Intermediate 11

6-Chloro-N-((6-methylpyridazin-3-yl)methyl)pyrido[3,4-d]pyrimidin-4-amine

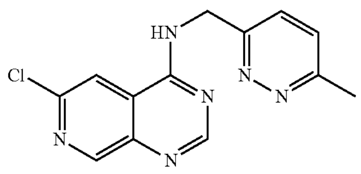 [SMILES: Cc1ccc(CNc2ncnc3cnc(Cl)cc23)nn1]

6-Chloropyrido[3,4-d]pyrimidin-4(3H)-one (50 mg, 0.27 mmol), (Benzotriazol-1-yloxy)tripyrrolidinophosphonium hexafluorophosphate (158 mg, 0.30 mmol) and (6-methylpyridazin-3-yl)methanamine hydrochloride salt (59 mg, 0.30 mmol) were dissolved in N,N-dimethylformamide (1 mL) and N,N-diisopropylethylamine (1.2 mL, 7 mmol). The reaction mixture was heated at 50° C. for 16 hours. After return to room temperature, brine (10 mL) was added and the mixture was extracted with ethyl acetate (3×15 mL). The combined organic phases were dried over $MgSO_4$, filtered and the solvent was removed in vacuo. The residue was purified by column chromatography on silica gel, eluting with 0-20% methanol in dichloromethane to give the title compound (50 mg, 65%).

LCMS (Method 4): [NM+]=288.0 at 2.33 min.

The following compound was prepared according to the same procedure described for the preparation of 6-Chloro-N-((6-methylpyridazin-3-yl)methyl)pyrido[3,4-d]pyrimidin-4-amine (Intermediate 11):

| Intermediate No. | Chemical Name<br>Structure | Analytical data<br>LC-MS |
|---|---|---|
| Intermediate 12 | 6-Chloro-N-((1R)-1-(2-(trifluoromethyl)pyrimidin-5-yl)ethyl)pyrido[3,4-d]pyrimidin-4-amine<br>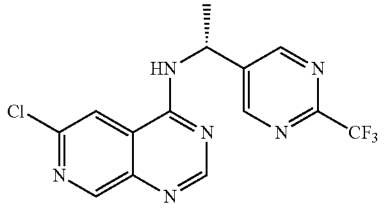 [SMILES: C[C@@H](Nc1ncnc2cnc(Cl)cc12)c1cnc(C(F)(F)F)nc1] | LCMS (Method 4): [MH+] = 355.0 at 2.76 min. |

Example 26

6-(4-Fluorophenyl)-N-((6-methylpyridazin-3-yl)methyl)pyrido[3,4-d]pyrimidin-4-amine

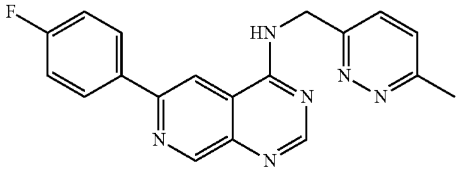 [SMILES: Cc1ccc(CNc2ncnc3cnc(-c4ccc(F)cc4)cc23)nn1]

6-Chloro-N-((6-methylpyridazin-3-yl)methyl)pyrido[3,4-d]pyrimidin-4-amine (50 mg, 0.17 mmol), potassium carbonate (96 mg, 0.70 mmol), 4-fluorophenylboronic acid (73 mg, 0.52 mmol) and tetrakis(triphenylphosphine)palladium (0) (30 mg, 0.026 mmol) were placed in a microwave vial. Dioxane (2 mL) and water (0.5 mL) were added and the solution was degassed with nitrogen for 10 minutes. The reaction mixture was heated to 110° C. for 20 minutes in a microwave reactor. After return to room temperature, water (2 mL) was added and the mixture was extracted with ethyl acetate (2×15 mL). The combined organic phase were dried over $MgSO_4$, filtered and the solvent was removed in vacuo. The residue was purified by column chromatography on silica gel, eluting with 0-20% methanol in dichloromethane to give the title compound (9 mg, 15%).

$^1H$ NMR (400 MHz, DMSO): δ 9.57 (t, J=5.1 Hz, 1H), 9.32 (s, 1H), 8.97 (s, 1H), 8.71 (s, 1H), 8.39 (dd, J=5.6, 8.6 Hz, 2H), 7.76 (d, J=8.6 Hz, 1H), 7.66 (d, J=8.6 Hz, 1H), 7.55 (dd, J=8.8, 8.8 Hz, 2H), 5.21 (d, J=5.6 Hz, 2H), 2.74 (s, 3H). LCMS (Method 4): [MH+]=347.0 at 3.18 min.

The following compound was prepared according to the same procedure described for the preparation of 6-(4-Fluorophenyl)-N-((6-methylpyridazin-3-yl)methyl)pyrido[3,4-d]pyrimidin-4-amine:

| Example No. | Chemical Name<br>Structure | Analytical data<br>$^1H$ NMR<br>LC-MS |
|---|---|---|
| Example 27 | 6-(4-Fluorophenyl)-N-[(1R)-1-[2-(trifluoromethyl)pyrimidin-5-yl]ethyl]pyrido[3,4-d]pyrimidin-4-amine<br>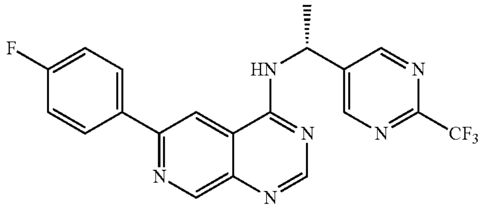 | $^1H$ NMR (400 MHz, DMSO): δ 9.19 (s, 2 H), 9.18 (s, 1 H), 9.04-9.01 (m, 1 H), 8.84 (s, 1 H), 8.56 (s, 1 H), 8.27 (ddd, J = 3.2, 5.3, 12.1 Hz, 2 H), 7.43 (dd, J = 8.8, 8.8 Hz, 2 H), 5.71-5.64 (m, 1 H), 1.77 (d, J = 7.2 Hz, 3 H). LCMS (Method 4): [MH+] = 415 at 4.66 min. |

Example 28

N-[(6-Methylpyridazin-3-yl)methyl]-6-(5-methylthiazol-2-yl)pyrido[3,4-d]pyrimidin-4-amine

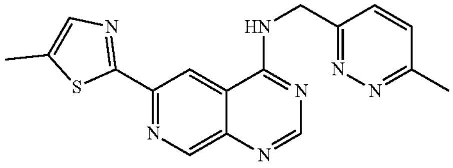

Nitrogen was bubbled for 5 min through a mixture of 6-chloro-N-((6-methylpyridazin-3-yl)methyl)pyrido[3,4-d]pyrimidin-4-amine (intermediate 11) (100 mg, 0.35 mmol), 5-methyl-2-(tributylstannyl)thiazole (271 mg, 0.7 mmol) and potassium carbonate (96 mg, 0.70 mmol) in N,N-dimethylformamide (2 mL), then [1,1'-bis(diphenylphosphino)ferrocene]dichloropalladium(II) complex with dichloromethane (57 mg, 0.07 mmol) and Cu(I)I (13 mg, 0.07 mmol) were added. The resulting mixture was heated to 100° C. for one hour. The reaction was cooled, diluted with ethyl acetate (30 mL) and washed with water (10 mL). The organic phase was filtered through Celite® and the solvent was removed in vacuo. The residue was purified by preparative HPLC to give the title compound (9 mg, 7%) as a brown solid.

$^1H$ NMR (400 MHz, DMSO): δ 9.72 (t, J=5.5 Hz, 1H), 9.13 (s, 1H), 8.99 (s, 1H), 8.59-8.57 (m, 1H), 7.75 (s, 1H), 7.62-7.58 (m, 1H), 7.53-7.49 (m, 1H), 5.05-5.01 (m, 2H), 2.60 (s, 3H), 2.55 (s, 3H). LCMS (Method 4): [MH+]=350 at 3.01 min.

The following compounds were prepared according to the same procedure described for the preparation of N-[(6-Methylpyridazin-3-yl)methyl]-6-(5-methylthiazol-2-yl)pyrido[3,4-d]pyrimidin-4-amine:

| Example No. | Chemical Name<br>Structure | Analytical data<br>$^1H$ NMR<br>LC-MS |
|---|---|---|
| Example 29 | N-[(6-methylpyridazin-3-yl)methyl]-6-(5-methyl-2-pyridyl)pyrido[3,4-d]pyrimidin-4-amine<br>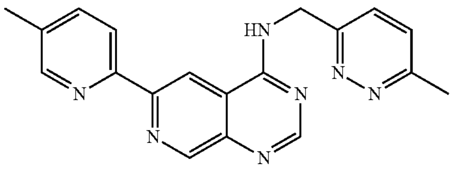 | $^1H$ NMR (400 MHz, DMSO): δ 9.71 (t, J = 5.1 Hz, 1 H), 9.23-9.17 (m, 2 H), 8.59 (d, J = 10.7 Hz, 2 H), 8.42-8.36 (m, 1 H), 7.86-7.79 (m, 1 H), 7.62-7.57 (m, 1 H), 7.53-7.48 (m, 1 H), 5.04 (d, J = 5.4 Hz, 2 H), 2.62-2.59 (m, 3 H), 2.42 (s, 3 H). LCMS (Method 4): [MH+] = 344 at 2.33 min. |

-continued

| Example No. | Chemical Name Structure | Analytical data $^1H$ NMR LC-MS |
|---|---|---|
| Example 30 | 6-(5-methylthiazol-2-yl)-N-[(1R)-1-[2-(trifluoromethyl)pyrimidin-5-yl]ethyl]pyrido[3,4-d]pyrimidin-4-amine 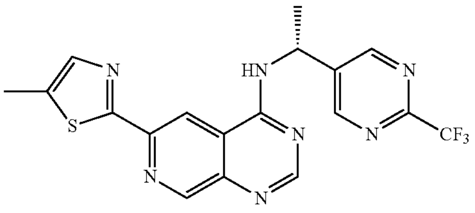 | $^1H$ NMR (400 MHz, DMSO): δ 9.34 (d, J = 7.0 Hz, 1 H), 9.19 (s, 2 H), 9.11 (s, 1 H), 9.05 (s, 1 H), 8.59 (s, 1 H), 7.76 (d, J = 1.1 Hz, 1 H), 5.72-5.64 (m, 1 H), 2.56 (s, 3 H), 1.75 (d, J = 7.0 Hz, 3 H). LCMS (Method 4): [MH+] = 418 at 4.66 min. |

Intermediate 13

6-Bromo-N-((6-methylpyridazin-3-yl)methyl)pyrido[3,2-d]pyrimidin-4-amine

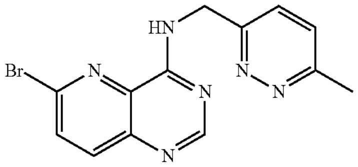

6-Bromopyrido[3,2-d]pyrimidin-4(3H)-one (150 mg, 0.66 mmol), (benzotriazol-1-yloxy)tripyrrolidinophosphonium hexafluorophosphate (380 mg, 0.73 mmol) and (6-methylpyridazin-3-yl)methanamine hydrochloride salt (143 mg, 0.73 mmol) were dissolved in N,N-dimethylformamide (1 mL) and N,N-diisopropylethylamine (2.9 mL, 16 mmol). The reaction mixture was heated to 50° C. for 6 hours. After return to room temperature, brine (10 mL) was added and the reaction was extracted with ethyl acetate (3×15 mL). The combined organic phases were dried over $MgSO_4$, filtered and the solvent was removed in vacuo. The residue was purified by column chromatography on silica gel, eluting with 0-20% methanol in dichloromethane to give the title compound (50 mg, 23%) as an off-white solid.

LCMS (Method 4): [MH+]=331.0 at 2.92 min.

The following compound was prepared according to the same procedure described for the preparation of 6-Bromo-N-((6-methylpyridazin-3-yl)methyl)pyrido[3,2-d]pyrimidin-4-amine (Intermediate 13):

| Intermediate No. | Chemical Name Structure | Analytical data $^1H$ NMR LC-MS |
|---|---|---|
| Intermediate 14 | (R)-6-Bromo-N-(1-(2-(trifluoromethyl)pyrimidin-5-yl)ethyl)pyrido[3,2-d]pyrimidin-4-amine 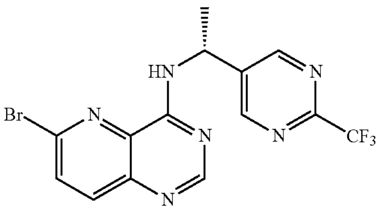 | LCMS (Method 4): [MH+] = 399.0 at 3.03 min. |

Example 31

6-(4-Fluorophenyl)-N-((6-methylpyridazin-3-yl)methyl)pyrido[3,2-d]pyrimidin-4-amine

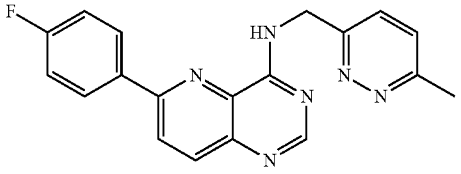 [SMILES: Cc1ccc(CNc2ncnc3ccc(-c4ccc(F)cc4)nc23)nn1]

6-Bromo-N-((6-methylpyridazin-3-yl)methyl)pyrido[3,2-d]pyrimidin-4-amine (Intermediate 13) (50 mg, 0.15 mmol), potassium carbonate (63 mg, 0.45 mmol), 4-fluorophenylboronic acid (23 mg, 0.16 mmol) and [1,1'-Bis(diphenylphosphino)ferrocene]dichloropalladium(II) (11 mg, 0.016 mmol) were placed in a microwave vial. 1.4-Dioxane (2 mL) and water (0.5 mL) were added and the solution was degassed with nitrogen for 10 minutes. The reaction mixture was heated to 110° C. for 20 minutes in a microwave reactor. After return to room temperature, water (2 mL) was added and the mixture was extracted with ethyl acetate (2×15 mL). The combined organic phases were dried over $MgSO_4$, filtered and the solvent was removed in vacuo. The residue was purified by column chromatography on silica gel, eluting with 0-20% methanol in dichloromethane to give the title compound (22 mg, 42%) as an off-white solid.

$^1$H NMR (400 MHz, $CDCl_3$): δ 8.65 (s, 1H), 8.22 (t, J=5.9 Hz, 1H), 8.19-8.08 (m, 4H), 7.54 (d, J=8.6 Hz, 1H), 7.33 (d, J=8.6 Hz, 1H), 7.23 (t, J=6.9 Hz, 2H), 5.19 (d, J=6.1 Hz, 2H), 2.73 (s, 3H). LCMS (Method 4): [MH+]=347.0 at 2.93 min.

Example 32

N-((6-methylpyridazin-3-yl)methyl)-6-(5-methylpyridin-2-yl)pyrido[3,2-d]-pyrimidin-4-amine

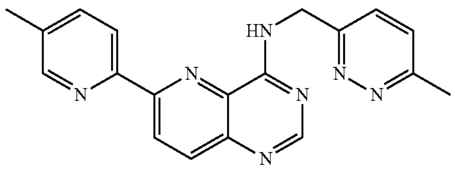

Nitrogen was bubbled for 5 min through a mixture of 6-chloro-N-((6-methylpyridazin-3-yl)methyl)pyrido[3,2-d]pyrimidin-4-amine (70 mg, 0.21 mmol), 5-methyl-2-(tributylstannyl)pyridine (0.15 mL, 0.42 mmol) and tetrakis(triphenylphosphine)palladium(0) (37 mg, 0.032 mmol) in N,N-dimethylformamide (2 mL). The reaction mixture was heated to 80° C. for 18 hours. The crude was cooled down to room temperature, diluted in methanol and loaded onto an SCX cartridge. The cartridge was washed with methanol and the filtrate was collected when eluting with a 7M solution of ammonia in methanol. The solvent was removed in vacuo and the residue was purified by preparative HPLC to give the title compound (19 mg, 26% yield).

$^1$H NMR (400 MHz, $CDCl_3$): δ 8.84 (d, J=8.8 Hz, 1H), 8.67 (s, 1H), 8.54 (d, J=1.8 Hz, 1H), 8.46 (d, J=8.0 Hz, 1H), 8.27 (dd, J=5.3, 5.3 Hz, 1H), 8.20 (d, J=8.9 Hz, 1H), 7.69 (dd, J=1.9, 8.2 Hz, 1H), 7.56 (d, J=8.5 Hz, 1H), 7.34 (d, J=8.7 Hz, 1H), 5.20 (d, J=5.9 Hz, 2H), 2.74 (s, 3H), 2.43 (s, 3H). LCMS (Method 3): [MH+]=344.2 at 3.34 min.

The following compounds were synthesised following the same procedure used for the preparation of N-((6-methylpyridazin-3-yl)methyl)-6-(5-methylpyridin-2-yl)pyrido[3,2-d]-pyrimidin-4-amine:

| Example No. | Chemical Name<br>Structure | Analytical data<br>$^1$H NMR<br>LC-MS |
|---|---|---|
| Example 33 | N-(1-(3-methyl-1,2,4-oxadiazol-5-yl)ethyl)-6-(5-methylpyridin-2-yl)pyrido[3,2-d]pyrimidin-4-amine 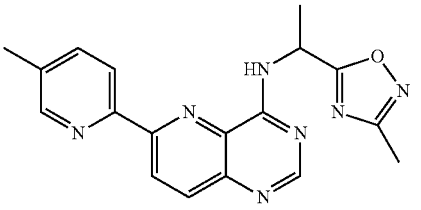 | $^1$H NMR (400 MHz, $CDCl_3$): δ 8.84 (d, J = 8.9 Hz, 1 H), 8.65 (s, 1 H), 8.56 (d, J = 1.8 Hz, 1 H), 8.43 (d, J = 8.2 Hz, 1 H), 8.22 (d, J = 8.9 Hz, 1 H), 7.71-7.63 (m, 2 H), 5.93-5.85 (m, 1 H), 2.44 (d, J = 11.0 Hz, 6H), 1.87 (d, J = 7.0 Hz, 3 H). LCMS (Method 4): [MH+] = 348.3 at 2.97 min. |

-continued

| Example No. | Chemical Name<br>Structure | Analytical data<br>$^1$H NMR<br>LC-MS |
|---|---|---|
| Example 34 | N-[(6-methylpyridazin-3-yl)methyl]-6-(5-methylthiazol-2-yl)pyrido[3,2-d]pyrimidin-4-amine<br>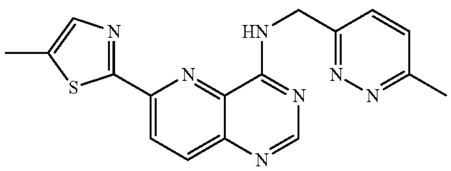 | $^1$H NMR (400 MHz, DMSO): δ 9.07 (dd, J = 6.0, 6.0 Hz, 1 H), 8.51-8.48 (m, 2 H), 8.24 (d, J = 8.8 Hz, 1 H), 7.79 (s, 1 H), 7.59 (d, J = 8.7 Hz, 1 H), 7.52 (d, J = 8.7 Hz, 1 H), 5.08 (d, J = 6.0 Hz, 2 H), 2.61 (s, 3 H), 2.58 (d, J = 1.1 Hz, 3 H). LCMS (Method 4): [MH+] = 350 at 2.68 min. |

Example 35

(R)-6-(5-Methylpyridin-2-yl)-N-(1-(2-(trifluoromethyl)pyrimidin-5-yl)ethyl)pyrido[3,2-d]pyrimidin-4-amine

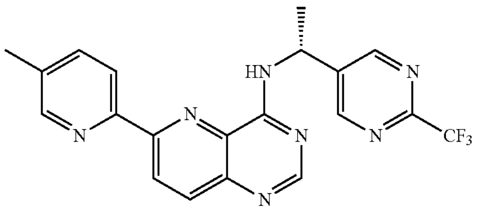 [SMILES: Cc1ccc(-c2ccc3ncnc(N[C@H](C)c4cnc(C(F)(F)F)nc4)c3n2)nc1]

To (R)-6-bromo-N-(1-(2-(trifluoromethyl)pyrimidin-5-yl)ethyl)pyrido[3,2-d]pyrimidin-4-amine (Intermediate 14) (210 mg, 0.53 mmol) in N,N-dimethylformamide (4.0 mL) was added potassium carbonate (145 mg, 1.05 mmol), [1,1'-bis(diphenylphosphino)ferrocene]dichloropalladium (II) (86 mg, 0.10 mmol), and copper iodide (20 mg). The mixture was stirred for 10 minutes and then 3-methyl-5-tributylstannylthiazole (402 mg, 1.05 mmol) was added. The reaction was heated to 100° C. for 16 hours. After return to room temperature, water (10 mL) was added and the reaction was extracted with dichloromethane (3×10 mL). Combined organic phases were filtered through a hydrophobic frit. The solvent was removed in vacuo. The residue was purified by preparative HPLC to give the title compound (7.1 mg, 33%) as an off-white solid.

$^1$H NMR (400 MHz, DMSO): δ 9.25 (s, 2H), 8.94 (d, J=8.0 Hz, 1H), 8.88 (d, J=8.2 Hz, 1H), 8.83 (d, J=8.8 Hz, 1H), 8.61 (d, J=1.4 Hz, 1H), 8.52 (s, 1H), 8.24 (d, J=8.8 Hz, 1H), 7.89 (dd, J=1.7, 8.1 Hz, 1H), 5.80 (d, J=7.3 Hz, 1H), 2.43 (s, 3H), 1.83 (d, J=7.2 Hz, 3H). LCMS (Method 3): [M+H]=412.2 at 4.60 min.

Example 36

(R)-6-(5-methylthiazol-2-yl)-N-(1-(2-(trifluoromethyl)pyrimidin-5-yl)ethyl)-pyrido[3,2-d]pyrimidin-4-amine

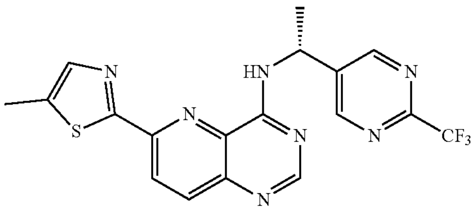 [SMILES: Cc1cnc(-c2ccc3ncnc(N[C@H](C)c4cnc(C(F)(F)F)nc4)c3n2)s1]

Nitrogen was bubbled for 5 min through a mixture of (R)-6-bromo-N-(1-(2-(trifluoromethyl)pyrimidin-5-yl) ethyl)pyrido[3,2-d]pyrimidin-4-amine (intermediate 14) (100 mg, 0.25 mmol), potassium carbonate (69 mg, 0.501 mmol), 3-methyl-5-tributylstannylthiazole (195 mg, 0.50 mmol) and copper iodide (9.5 mg, 0.05 mmol) in N,N-dimethylformamide (4.0 mL), then [1,1'-bis(diphenylphosphino)ferrocene]dichloropalladium(II) complex with dichloromethane (41 mg, 0.05 mmol) was added. The reaction was heated to 100° C. for one hour. After return to room temperature, water (10 mL) was added and the reaction was extracted with dichloromethane (3×10 mL). Combined organic phases were filtered through a hydrophobic frit. The solvent was removed in vacuo. The residue was purified by preparative HPLC to give the title compound (6.8 mg, 7%) as an off-white solid.

$^1$H NMR (400 MHz, DMSO): δ 9.24 (s, 2H), 8.59 (d, J=8.0 Hz, 1H), 8.53-8.48 (m, 2H), 8.24 (d, J=8.8 Hz, 1H), 7.79 (d, J=1.1 Hz, 1H), 5.76-5.71 (m, 1H), 2.58 (s, 3H), 1.82 (d, J=7.0 Hz, 3H). LCMS (Method 3): [M+H]=418.2 at 4.20 min.

Intermediate 15

6-(4-Fluorophenyl)pyrido[3,2-d]pyrimidin-4(3H)-one

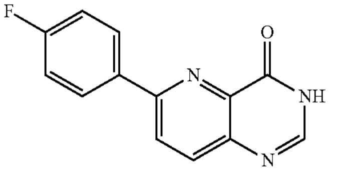

Nitrogen was bubbled for 15 minutes through a mixture of 6-bromopyrido[3,2-d]pyrimidin-4(3H)-one (286 mg, 1.27 mmol), potassium carbonate (252 mg, 3.80 mmol), 4-fluoro (phenyl boronic acid) (195 mg, 1.40 mmol) in 1,4-dioxane (5 mL) and water (0.5 mL), then [1,1'bis(diphenylphosphino)ferrocene]dichloropalladium(II) complex with dichloromethane (93 mg, 0.127 mmol) was added. The reaction was sealed and heated to 110° C. for 30 minutes in a microwave reactor. After return to room temperature, water (5 mL) was added and the reaction was extracted with ethyl acetate (3×5 mL). The combined organic phases were washed with brine (10 mL) and passed through a hydrophobic frit. The solvent was removed in vacuo. The residue was purified by column chromatography on silica gel, eluting with 0-15% methanol in dichloromethane to give the title compound (294 mg, 96%) as a red powder.

LCMS (Method 4): [M+H]=242.0 at 3.15 min.

Example 37

(R)-6-(4-fluorophenyl)-N-(1-(2-(trifluoromethyl)pyrimidin-5-yl)ethyl)pyrido[3,2-d]pyrimidin-4-amine

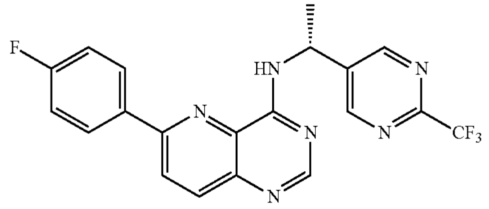

To a solution of 6-(4-fluorophenyl)pyrido[3,2-d]pyrimidin-4(3H)-one (intermediate 15) (150 mg, 0.62 mmol) in N,N-dimethylformamide (2 mL) was successively added (benzotriazol-1-yloxy)tripyrrolidinophosphonium hexafluorophosphate (356 mg, 0.68 mmol) and di-isopropylethylamine (2.7 mL, 15.6 mmol). The resulting mixture was heated to 50° C. for one hour then (R)-1-(2-(trifluoromethyl)pyrimidin-5-yl)ethan-1-amine hydrochloride (156 mg, 0.68 mmol) was added and the heating was maintained at 50° C. for 2 hours. After return to room temperature, the mixture was diluted with ethyl acetate (50 mL) and water (10 mL). The organic phase was washed with brine (2×20 mL), passed through a hydrophobic frit and the solvent was removed in vacuo. The residue was purified by preparative HPLC to give the title compound (13 mg, 5%) as an off-white solid.

$^1$H NMR (400 MHz, DMSO): δ 9.21 (s, 2H), 8.53-8.44 (m, 4H), 8.19 (d, J=8.8 Hz, 1H), 7.40 (dd, J=8.8, 8.8 Hz, 2H), 5.74 (q, J=6.9 Hz, 1H), 2.07 (s, 1H), 1.81 (d, J=7.0 Hz, 3H). LCMS (Method 3): [M+H]=414.4 at 4.96 min.

The following compound was synthesised following the same procedure described for the preparation of (R)-6-(4-fluorophenyl)-N-(1-(2-(trifluoromethyl)pyrimidin-5-yl)ethyl)pyrido[3,2-d]pyrimidin-4-amine:

| Example No. | Chemical Name Structure | Analytical data $^1$H NMR LC-MS |
|---|---|---|
| Example 38 | 6-(4-Fluorophenyl)-N-(1-(3-methyl-1,2,4-oxadiazol-5-yl)ethyl)pyrido[3,2-d]pyrimidin-4-amine 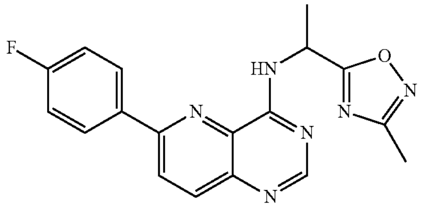 | $^1$H NMR (400 MHz, DMSO): δ 9.12 (d, J = 8.3 Hz, 1 H), 8.59-8.51 (m, 4 H), 8.23 (d, J = 8.9 Hz, 1 H), 7.41 (dd, J = 8.9, 8.9 Hz, 2 H), 5.92-5.84 (m, 1 H), 2.35 (s, 3 H), 1.81 (d, J = 7.2 Hz, 3 H). LCMS (Method 3): [M + H] = 351.3 at 3.92 min. |

Intermediate 16

6-Bromopteridin-4(3H)-one

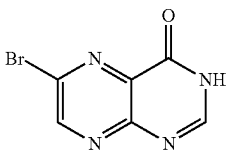 [SMILES: O=c1[nH]cnc2ncc(Br)nc12]

Acetic anhydride (10 mL, 105.79 mmol) was added to a suspension of 3-amino-6-bromopyrazine-2-carboxamide (2 g, 9.22 mmol) in triethyl orthoformate (20 mL, 120.24 mmol). The reaction mixture was heated to 120° C. for one hour and at 90° C. for 2 days. After return to room temperature, the reaction was concentrated in vacuo. The residue was triturated in IPA, filtered and dried to give the title compound (1.3 g, 62%) as a brown solid.

LCMS (Method 4): [MH+]=227.0 at 1.81 min.

Intermediate 17

6-(4-Fluorophenyl)pteridin-4(3H)-one

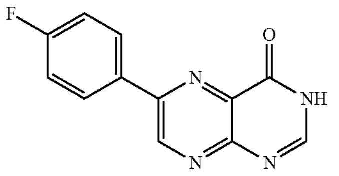 [SMILES: O=c1[nH]cnc2ncc(-c3ccc(F)cc3)nc12]

6-Bromopteridin-4(3H)-one (Intermediate 16) (300 mg, 1.32 mmol), potassium carbonate (548 mg, 3.96 mmol), 4-fluorophenylboronic acid (203 mg, 1.45 mmol) and [1,1'-Bis(diphenylphosphino)ferrocene]dichloropalladium(II) (97 mg, 0.132 mmol) were placed in a microwave vial. Dioxane (5 mL) and water (0.5 mL) were added and the solution was degassed with nitrogen for 10 minutes. The reaction mixture was heated to 110° C. for 35 minutes in a microwave reactor. After return to room temperature, water (5 mL) was added and the mixture was extracted with a mixture of $CHCl_3$/IPA (60:40) (3×20 mL). The combined organic phases were dried over $MgSO_4$, filtered and the solvent was removed in vacuo to give the title compound (280 mg, 88%) as a red solid.

LCMS (Method 4): [MH+]=243.0 at 2.93 min.

Example 39

6-(4-Fluorophenyl)-N-((6-methylpyridazin-3-yl)methyl)pteridin-4-amine

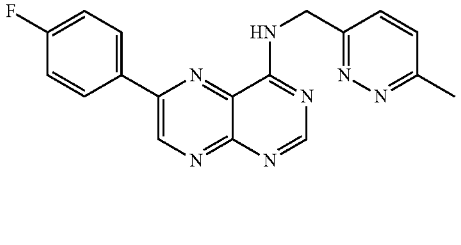

Step 1: Preparation of 4-chloro-6-(4-fluorophenyl)pteridine

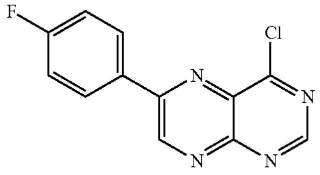 [SMILES: Fc1ccc(-c2cnc3ncnc(Cl)c3n2)cc1]

To a solution of 6-(4-fluorophenyl)pteridin-4(3H)-one (Intermediate 17) (280 mg, 1.16 mmol) in thionyl chloride (2.6 mL, 35.98 mmol) was added N,N-dimethylformamide (0.1 mL, 0.01 mmol) and the mixture was heated at reflux for three hours. After return to room temperature, toluene (5 mL) was added and the solvent was removed in vacuo. Toluene was added two more times and evaporated in vacuo to give the title compound which was taken on to the next step without further purification.

Step 2: Preparation of 6-(4-fluorophenyl)-N-((6-methylpyridazin-3-yl)methyl)pteridin-4-amine 4-Chloro-6-(4-fluorophenyl)pteridine (120 mg, 0.460 mmol), 6-methylpyridazin-3-yl)methanamine dihydrochloride (81 mg, 0.506 mmol) and triethylamine (0.19 mL, 1.38 mmol) were dissolved in isopropanol (2.0 mL) and heated to 70° C. for 3 hours. Then, the mixture was cooled down to room temperature and loaded onto an SCX cartridge. The cartridge was washed with methanol and the filtrate was collected when eluting with a 7M solution of ammonia in methanol. The solvent was removed in vacuo and the residue was purified by preparative HPLC to give the title compound (8.6 mg, 7% yield).

$^1$H NMR (400 MHz, $CDCl_3$): δ 9.48 (s, 1H), 8.81 (s, 1H), 8.36 (s, 1H), 8.16 (dd, J=5.3, 8.6 Hz, 2H), 7.53 (d, J=8.6 Hz, 1H), 7.36 (d, J=8.6 Hz, 1H), 7.25-7.22 (m, 2H), 5.18 (d, J=5.6 Hz, 2H), 2.75 (s, 3H). LCMS (Method 4): [MH+]=348.0 at 3.17 min.

Example 40

6-(4-Fluorophenyl)-N-(1-(3-methyl-1,2,4-oxadiazol-5-yl)ethyl)pteridin-4-amine

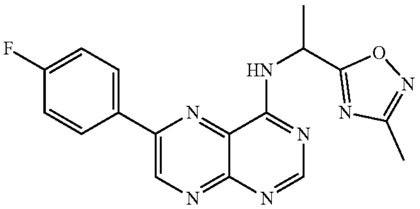 [SMILES: Cc1noc(C(C)Nc2ncnc3ncc(-c4ccc(F)cc4)nc23)n1]

To a solution of 6-(4-fluorophenyl)pteridin-4(3H)-one (Intermediate 17) (40 mg, 0.165 mmol) in N,N-dimethylformamide (4 mL) was successively added (benzotriazol-1-yloxy)tripyrrolidinophosphonium hexafluorophosphate (95 mg, 0.18 mmol), di-isopropylethylamine (0.71 mL, 4.1 mmol) and 1-(3-methyl-1,2,4-oxadiazol-5-yl)ethan-1-amine hydrochloride (36 mg, 0.18 mmol). The resulting mixture was heated to 50° C. for 2 hours. After return to room temperature, the mixture was diluted with water (10 mL) and extracted with ethyl acetate (3×10 mL). The combined organic phases were passed through a hydrophobic frit and the solvent was removed in vacuo. The residue was purified by preparative PLC to give the title compound (113 mg, 1200) as a yellow solid.

$^1$H NMR (400 MHz, DMSO): δ 9.81 (s, 1H), 9.46 (d, J=8.2 Hz, 1H), 8.67-8.60 (m, 3H), 7.47 (dd, J=8.9, 8.9 Hz, 2H), 5.94-5.88 (m, 1H), 2.35 (s, 3H), 1.81 (d, J=7.2 Hz, 3H). LCMS (Method 3): [MH+]=352.2 at 3.93 min.

The following compounds reported in the table below were prepared according to the same procedure described for the preparation of 6-(4-Fluorophenyl)-N-(1-(3-methyl-1,2,4-oxadiazol-5-yl)ethyl)pteridin-4-amine:

| Example No. | Chemical Name<br>Structure | Analytical data<br>$^1$H NMR LC-MS |
|---|---|---|
| Example 41 | (R)-6-(4-fluorophenyl)-N-(1-(2-(trifluoromethyl)pyrimidin-5-yl)ethyl)pteridin-4-amine<br>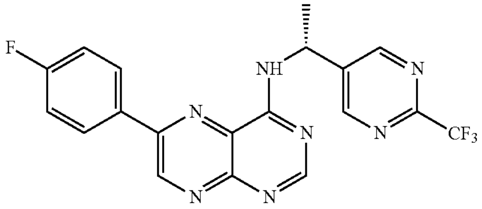 [SMILES: C[C@@H](Nc1ncnc2ncc(-c3ccc(F)cc3)nc12)c1cnc(C(F)(F)F)nc1] | $^1$H NMR (400 MHz, DMSO): δ 9.77 (s, 1 H), 9.23 (s, 2 H), 9.20 (d, J = 8.2 Hz, 1 H), 8.64-8.57 (m, 3 H), 7.47 (dd, J = 8.8, 8.8 Hz, 2 H), 5.82-5.76 (m, 1 H), 1.81 (d J = 7.0 Hz, 3 H). LCMS (Method 4): [M + H] = 416.2 at of 4.56 min. |
| Example 42 | 6-(4-Fluorophenyl)-N-((6-methylpyridin-3-yl)methyl)pteridin-4-amine<br>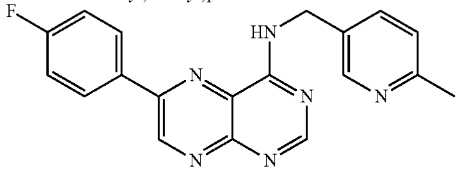 | $^1$H NMR (400 MHz, DMSO): δ 9.76 (s, 1 H), 9.53 (dd, J = 6.2, 6.2 Hz, 1 H), 8.63 (s, 1 H), 8.61-8.56 (m, 2 H), 8.53 (d, J = 2.0 Hz, 1 H), 7.72 (dd, J = 2.4, 7.9 Hz, 1 H), 7.45 (dd, J = 8.9, 8.9 Hz, 2 H), 7.22 (d, J = 8.0 Hz, 1 H), 4.83 (d, J = 6.4 Hz, 2 H), 2.44 (s, 3 H). LCMS (Method 3): [M + H] = 347.3 at 2.58 min. |

The following compounds reported in the table below were obtained as single isomers by chiral preparative SFC purification of the appropriate racemic mixture hereinabove described.

| Example No. | Chemical Name<br>Structure | Analytical data<br>$^1$H NMR<br>LC-MS |
|---|---|---|
| Example 43 | Single enantiomer 1 of N-(1-(3-Methyl-1,2,4-oxadiazol-5-yl)ethyl)-6-(5-methylpyridin-2-yl)pyrido[2,3-d]pyrimidin-4-amine<br>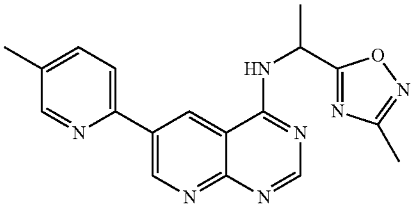 | $^1$H NMR (400 MHz, DMSO): δ 9.78 (d, J = 2.3 Hz, 1 H), 9.52 (d, J = 2.0 Hz, 1 H), 9.37 (d, J = 7.1 Hz, 1 H), 8.68 (s, 2 H), 8.16 (d, J = 8.1 Hz, 1 H), 7.90 (dd, J = 1.4, 8.0 Hz, 1 H), 5.90-5.83 (m, 1 H), 2.45 (s, 3 H), 2.38 (s, 3 H), 1.80 (d, J = 7.1 Hz, 3 H). LCMS (Method 4) [MH+] = 348 at 2.87 min. Chiral analysis (Method 10) at 1.60 min. |

-continued

| Example No. | Chemical Name<br>Structure | Analytical data<br>$^1H$ NMR<br>LC-MS |
|---|---|---|
| Example 44 | Single enantiomer 2 of N-(1-(3-Methyl-1,2,4-oxadiazol-5-yl)ethyl)-6-(5-methylpyridin-2-yl)pyrido[2,3-d]pyrimidin-4-amine<br>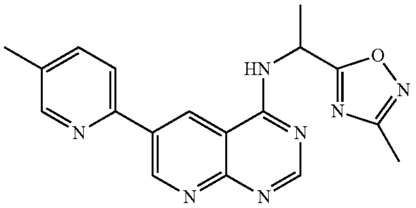 | $^1H$ NMR (400 MHz, DMSO): δ 9.78 (d, J = 2.3 Hz, 1 H), 9.52 (d, J = 2.0 Hz, 1 H), 9.37 (d, J = 7.1 Hz, 1 H), 8.68 (s, 2 H), 8.16 (d, J = 8.1 Hz, 1 H), 7.90 (dd, J = 1.4, 8.0 Hz, 1 H), 5.90-5.83 (m, 1 H), 2.45 (s, 3 H), 2.38 (s, 3 H), 1.80 (d, J = 7.1 Hz, 3 H). LCMS (Method 3) [MH+] = 348 at 3.49 min. Chiral analysis (Method 10) at 2.34 min. |
| Example 45 | Single enantiomer 1 of 6-(4-fluorophenyl)-N-[1-(3-methyl-1,2,4-oxadiazol-5-yl)ethyl]pyrido[2,3-d]pyrimidin-4-amine<br>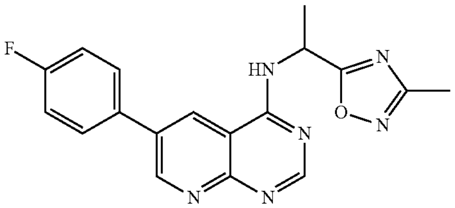 | $^1H$ NMR (400 MHz, DMSO): δ 9.45 (d, J = 2.3 Hz, 1 H), 9.23-9.18 (m, 2 H), 8.68 (s, 1 H), 8.04-7.99 (m, 2 H), 7.49 (dd, J = 8.8, 8.8 Hz, 2 H), 5.87 (d, J = 6.8 Hz, 1 H), 2.38 (s, 3 H), 1.80 (d, J = 7.1 Hz, 3 H). LCMS (Method 4): [MH+] = 351 at 3.21 min. Chiral analysis (Method 10) at 1.09 min. |
| Example 46 | Single enantiomer 2 of 6-(4-fluorophenyl)-N-[1-(3-methyl-1,2,4-oxadiazol-5-yl)ethyl]pyrido[2,3-d]pyrimidin-4-amine<br>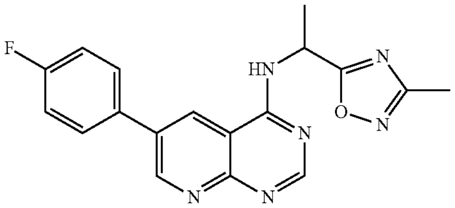 | $^1H$ NMR (400 MHz, DMSO): δ 9.45 (d, J = 2.5 Hz, 1 H), 9.22-9.18 (m, 2 H), 8.68 (s, 1 H), 8.04-7.99 (m, 2 H), 7.49 (dd, J = 8.8, 8.8 Hz, 2 H), 5.89-5.83 (m, 1 H), 2.38 (s, 3 H), 1.79 (d, J = 7.1 Hz, 3 H). LCMS (Method 4): [MH+] = 351 at 3.18 min. Chiral analysis (Method 10) at 1.45 min. |
| Example 47 | Single enantiomer 1 of N-(1-(3-methyl-1,2,4-oxadiazol-5-yl)ethyl)-6-(5-methylthiazol-2-yl)pyrido[2,3-d]pyrimidin-4-amine<br>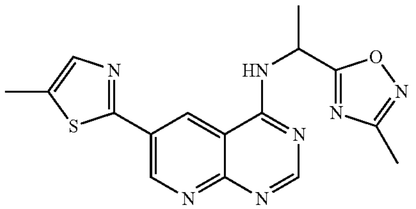 | $^1H$ NMR (400 MHz, DMSO): δ 9.57 (d, J = 2.0 Hz, 1 H), 9.47 (d, J = 4.3 Hz, 1 H), 9.37 (d, J = 2.0 Hz, 1 H), 8.69 (s, 1 H), 7.82 (s, 1 H), 5.90-5.84 (m, 1 H), 2.62 (s, 3 H), 2.38 (s, 3 H), 1.79 (d, J = 7.1 Hz, 3 H). LCMS (Method 3) [MH+] = 354 at 3.31 min. Chiral analysis (Method 5) at 1.21 min. |

-continued

| Example No. | Chemical Name Structure | Analytical data $^1$H NMR LC-MS |
|---|---|---|
| Example 48 | Single enantiomer 2 of N-(1-(3-methyl-1,2,4-oxadiazol-5-yl)ethyl)-6-(5-methylthiazol-2-yl)pyrido[2,3-d]pyrimidin-4-amine 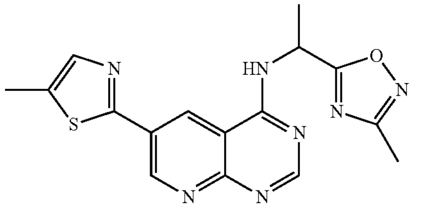 | $^1$H NMR (400 MHz, DMSO): δ 9.57 (d, J = 2.0 Hz, 1 H), 9.47 (d, J = 4.3 Hz, 1 H), 9.37 (d, J = 2.0 Hz, 1 H), 8.69 (s, 1 H), 7.82 (s, 1 H), 5.90-5.84 (m, 1 H), 2.62 (s, 3 H), 2.38 (s, 3 H), 1.79 (d, J = 7.1 Hz, 3 H). LCMS (Method 3) [MH+] = 354 at 3.31 min. Chiral analysis (Method 5) at 1.52 min. |
| Example 102 | Single enantiomer 1 of 6-(4-fluorophenyl)-N-[1-[3-(trifluoromethyl)-1,2,4-oxadiazol-5-yl]ethyl]pyrido[2,3-d]pyrimidin-4-amine 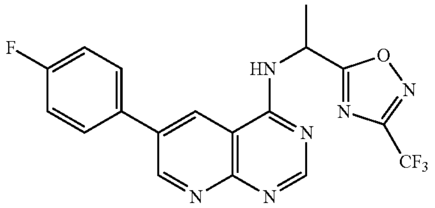 | $^1$H NMR (400 MHz, DMSO): δ 9.43 (d, J = 2.5 Hz, 1 H), 9.28 (d, J = 6.7 Hz, 1 H), 9.11 (d, J = 2.4 Hz, 1 H), 8.64 (s, 1 H), 8.00-7.95 (m, 2 H), 7.49-7.42 (m, 2 H), 5.94 (dq, J = 7.0, 7.0 Hz, 1 H), 1.83 (d, J = 7.1 Hz, 3 H). LCMS (Method 4): [MH$^+$] = 405 at 4.12 min. Chiral analysis (Method 24) at 1.02 min. |
| Example 103 | Single enantiomer 1 of 6-(4-fluorophenyl)-N-(1-(5-methyl-1,3,4-thiadiazol-2-yl)ethyl)pyrido[2,3-d]pyrimidin-4-amine (Isomer 1) 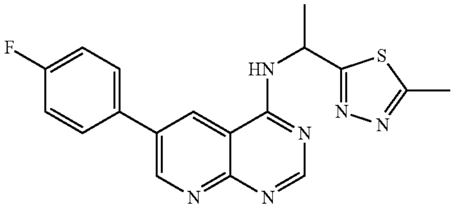 | $^1$H NMR (400 MHz, DMSO): δ 9.40 (d, J = 2.5 Hz, 1 H), 9.20-9.13 (m, 2 H), 8.69 (s, 1 H), 7.99-7.94 (m, 2 H), 7.45 (dd, J = 8.9, 8.9 Hz, 2 H), 6.01-5.96 (m, 1 H), 2.67 (s, 3 H), 1.82 (d, J = 7.0 Hz, 3 H). LCMS (Method 4): [MH+] = 367 at 2.96 min. Chiral analysis (Method 10) at 2.73 min. |
| Example 104 | Single enantiomer 2 of 6-(4-fluorophenyl)-N-(1-(5-methyl-1,3,4-thiadiazol-2-yl)ethyl)pyrido[2,3-d]pyrimidin-4-amine (Isomer 2) 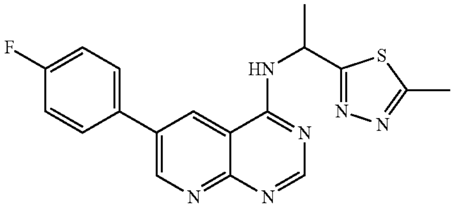 | $^1$H NMR (400 MHz, DMSO): δ 9.40 (d, J = 2.5 Hz, 1 H), 9.20-9.13 (m, 2 H), 8.69 (s, 1 H), 7.99-7.94 (m, 2 H), 7.45 (dd, J = 8.9, 8.9 Hz, 2 H), 6.01-5.96 (m, 1 H), 2.67 (s, 3 H), 1.82 (d, J = 7.0 Hz, 3 H). LCMS (Method 4): [MH+] = 367 at 2.95 min. Chiral analysis (Method 10) at 3.86 min. |

-continued

| Example No. | Chemical Name Structure | Analytical data $^1H$ NMR LC-MS |
|---|---|---|
| Example 105 | Single enantiomer 1 of N-[1-(3,5-difluoro-2-pyridyl)ethyl]-6-(4-fluorophenyl)pyrido[2,3-d]pyrimidin-4-amine 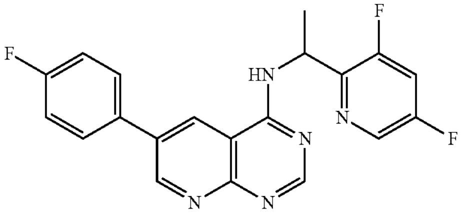 | $^1H$ NMR (400 MHz, DMSO): δ 9.36 (d, J = 2.4 Hz, 1 H), 9.24 (d, J = 2.4 Hz, 1 H), 9.00-8.98 (m, 1 H), 8.57 (s, 1 H), 8.47 (d, J = 2.4 Hz, 1 H), 8.00-7.92 (m, 3 H), 7.47-7.41 (m, 2 H), 5.90-5.84 (m, 1 H), 1.65 (d, J = 6.8 Hz, 3 H). LCMS (Method 4): [MH+] = 382 at 4.3 min. Chiral analysis (Method 31) at 1.41 min. |
| Example 106 | Single enantiomer 2 of N-[1-(3,5-difluoro-2-pyridyl)ethyl]-6-(4-fluorophenyl)pyrido[2,3-d]pyrimidin-4-amine 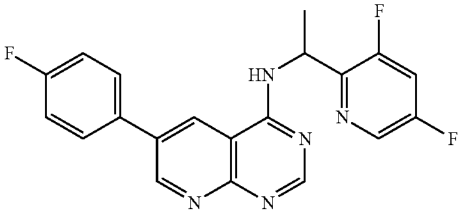 | $^1H$ NMR (400 MHz, DMSO): δ 9.35 (d, J = 2.4 Hz, 1 H), 9.24 (d, J = 2.4 Hz, 1 H), 9.00-8.98 (m, 1 H), 8.55 (s, 1 H), 8.47 (d, J = 2.4 Hz, 1 H), 8.00-7.94 (m, 3 H), 7.46-7.42 (m, 2 H), 5.90-5.84 (m, 1 H), 1.65 (d, J = 6.8 Hz, 3 H). LCMS (Method 4): [MH+] = 382 at 4.3 min. Chiral analysis (Method 31) at 2.11 min. |

Pharmacological Activity of the Compounds of the Invention.

In Vitro Electrophysiology Assay for $P2X_3$

Cells expressing $P2X_3$ receptors were grown according to standard practice and maintained at 37° C. in a 5% humidified CO2 atmosphere. The cells were seeded into T175 flask 2 days prior to the day of the assay and dissociated from the flasks using TrypLE when grown to confluence of 80-90%. The dissociated cells were resuspended in serum free media at a cell density of $3\times10^6$ cells/ml and loaded onto the Sophion Qube automated patch-clamp system. The extracellular assay buffer contained 145 mM NaCl, 4 mM KCl, 2 mM $CaCl_2$), 1 mM $MgCl_2$, 10 mM HEPES, and 10 mM glucose at pH 7.4. The intracellular assay solution contained 140 mM CsF, 10 mM NaCl, 10 mM EGTA, 10 mM HEPES at pH 7.2. Agonist stock solutions were prepared in $H_2O$ and diluted in bath solution prior to use. All antagonists were prepared as 10 mM stock solutions in DMSO and diluted in bath solution prior to use. All experiments were performed under the whole-cell patch clamp configuration at room temperature with 384 individual cells being voltage clamped at −60 mV simultaneously on the Sophion Qube instrument. Two baseline responses were established with the application of α,β-MeATP (800 nM), with the subsequent agonist applications being washed out using extracellular assay buffer containing 0.5 U/ml apyrase. Following the second agonist application, antagonist was incubated in the absence of α,β-MeATP for 10 minutes. After antagonist preincubation, 800 nM α,β-MeATP and antagonist were co-administered to determine the inhibitory effect of the antagonist. One concentration of an antagonist was assessed against a single cell, with different concentrations of the antagonist applied to other cells on the 384 recording substrate. The control $P2X_3$ current amplitude was taken from the peak current amplitude from the second agonist response prior to preincubation with antagonist. The peak $P2X_3$ current amplitude in the presence of antagonist was used to calculate the inhibitory effect at each concentration of the antagonist according to the following equation:

Percentage inhibition of $P2X_3$=($P2X_3$ control peak amplitude-$P2X_3$ antagonist peak amplitude)/$P2X_3$ control peak amplitude)*100.

Concentration-response curves were constructed from ten different concentrations with each concentration of antagonist tested on at least two individual cells. The concentration of the antagonist to inhibit $P2X_3$ current by 50% ($IC_{50}$) was determined by fitting the data with the following equation:

$$Y=a+[(b-a)/(1+10\^((\log c-x)d)]$$

Where 'a' is minimum response, 'b' is maximum response, 'c' is $IC_{50}$ and 'd' is Hill slope.

The results for individual compounds are provided below in Table 8 and are expressed as range of activity.

TABLE 8

| Example No. | h $P2X_3$ |
|---|---|
| 1 | +++ |
| 2 | +++ |
| 3 | ++ |
| 4 | ++ |
| 5 | + |

TABLE 8-continued

| Example No. | h $P2X_3$ |
|---|---|
| 6 | +++ |
| 7 | +++ |
| 8 | ++ |
| 9 | +++ |
| 10 | +++ |
| 11 | +++ |
| 12 | ++ |
| 13 | +++ |
| 14 | +++ |
| 15 | +++ |
| 16 | +++ |
| 17 | ++ |
| 18 | + |
| 19 | +++ |
| 20 | +++ |
| 21 | + |
| 22 | + |
| 23 | + |
| 24 | + |
| 25 | + |
| 26 | +++ |
| 27 | +++ |
| 28 | +++ |
| 29 | ++ |
| 30 | +++ |
| 31 | ++ |
| 32 | +++ |
| 33 | ++ |
| 34 | ++ |
| 35 | +++ |
| 36 | +++ |
| 37 | ++ |
| 38 | + |
| 39 | ++ |
| 40 | ++ |
| 41 | ++ |
| 42 | +++ |
| 43 | + |
| 44 | +++ |
| 45 | + |
| 46 | +++ |
| 47 | ++ |
| 48 | ++ |
| 49 | +++ |
| 50 | +++ |
| 51 | ++ |
| 52 | +++ |
| 54 | ++ |
| 55 | ++ |
| 56 | ++ |
| 58 | +++ |
| 59 | + |
| 60 | ++ |
| 63 | ++ |
| 63a | ++ |
| 65 | + |
| 66 | ++ |
| 67 | ++ |
| 68 | ++ |
| 69 | +++ |
| 70 | ++ |
| 71 | ++ |
| 72 | ++ |
| 73 | ++ |
| 75 | ++ |
| 76 | +++ |
| 77 | ++ |
| 78 | ++ |
| 79 | ++ |
| 80 | ++ |
| 82 | ++ |
| 83 | ++ |
| 84 | ++ |
| 87 | + |
| 88 | +++ |
| 91 | ++ |
| 92 | ++ |
| 93 | ++ |

TABLE 8-continued

| Example No. | h $P2X_3$ |
|---|---|
| 94 | + |
| 95 | +++ |
| 102 | ++ |
| 103 | + |
| 104 | ++ |
| 105 | ++ |
| 106 | + |
| 107 | +++ |

wherein the compounds are classified in term of potency with respect to their inhibitory activity on $P2X_3$ isoform according to the following classification criterion:

$$+++: pIC_{50}hP2X_3 > 6.5$$

$$++: 6.5 < pIC_{50}hP2X_3 > 5.5$$

$$+: 5.5 < pIC_{50}hP2X_3 > 4.5$$

In Vitro Electrophysiology Assay for $P2X_2$/3

The same assay protocol was used for the $P2X_{2/3}$ assay as the $P2X_3$ assay with two modifications: 1) 10 μM ATP was used as the agonist; and 2) the mean current amplitude was measured seven seconds after the application of agonist.

The results of Table 9 indicate that representative compounds of the present invention are selective $P2X_3$ antagonist.

TABLE 9

| Example No. | $hP2X_3$ | $hP2X_{2/3}$ |
|---|---|---|
| 3 | ++ | + |
| 7 | +++ | + |
| 9 | +++ | ++ |
| 11 | +++ | + |
| 13 | +++ | + |
| 14 | +++ | ++ |
| 15 | +++ | ++ |
| 19 | +++ | + |
| 27 | +++ | + |
| 32 | +++ | + |
| 34 | ++ | + |
| 42 | +++ | + |
| 46 | +++ | + |
| 49 | +++ | + |
| 51 | ++ | + |
| 52 | +++ | + |
| 55 | ++ | + |
| 67 | ++ | + |
| 68 | ++ | + |
| 69 | +++ | + |
| 78 | ++ | + |
| 88 | +++ | + |
| 92 | ++ | + |
| 102 | ++ | + |
| 104 | ++ | + |
| 107 | +++ | + |

wherein the compounds are classified in term of potency with respect to their inhibitory activity on $P2X_3$ and $P2X_{2/3}$ isoforms according to the following classification criterion:

+++: $pIC_{50}hP2X_3$ or $hP2X_{2/3} > 6.5$

++: $6.5 < pIC_{50}hP2X_3$ or $hP2X_{2/3} > 5.5$

+: $5.5 < pIC_{50}hP2X_3$ or $hP2X_{2/3} > 4.5$

Comparative Example A

6-(4-fluorophenyl)-4-[(6-methyl-3-pyridyl)methoxy]pyrido[2,3-d]pyrimidine

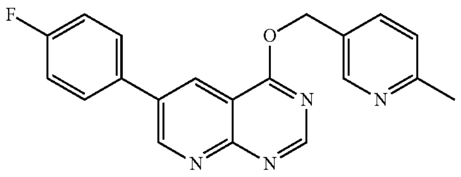 [SMILES: Cc1ccc(COc2ncnc3ncc(-c4ccc(F)cc4)cc23)cn1]

Step 1: Synthesis of 6-bromo-4-((6-methylpyridin-3-yl)methoxy)pyrido[2,3-d]pyrimidine

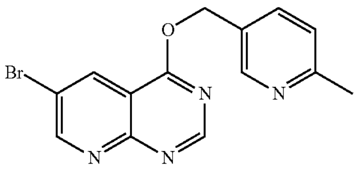

6-Bromopyrido[2,3-d]pyrimidin-4(3H)-one (202 mg, 0.89 mmol) (Intermediate 1), 5-hydroxymethyl-2-methylpyridine (110 mg, 0.89 mmol) and triphenylphosphine (328 mg, 1.25 mmol) were stirred in dry THE (7 mL) and a solution of diisopropyl azodicarboxylate (229 L, 1.16 mmol) in dry THE (3 mL) was added dropwise and stirred at room temperature for 6 hours. The reaction was filtered and the precipitate was washed with (2:1) DCM/MeOH (20 mL). The filtrates were combined and the solvent was removed in vacuo. The residue was purified by chromatography on silica gel eluting with 0-100% EtOAc in DCM to give 6-bromo-4-((6-methylpyridin-3-yl)methoxy)pyrido[2,3-d]pyrimidine (164 mg, 55%).

$^1H$ NMR (400 MHz, DMSO): δ 9.08 (d, J=2.6 Hz, 1H), 8.89 (s, 1H), 8.67 (d, J=2.6 Hz, 1H), 8.55 (d, J=2.1 Hz, 1H), 7.72 (dd, J=2.4, 8.0 Hz, 1H), 7.24 (d, J=8.0 Hz, 1H), 5.20 (s, 2H), 2.44 (s, 3H).

Step 2: Synthesis of 6-(4-fluorophenyl)-4-[(6-methyl-3-pyridyl)methoxy]pyrido[2,3-d]pyrimidine

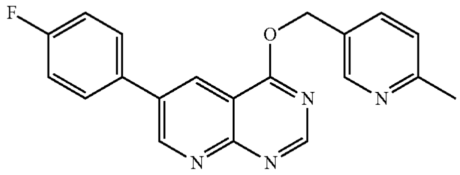

Nitrogen gas was bubbled through a mixture of 6-bromo-4-((6-methylpyridin-3-yl)methoxy)pyrido[2,3-d]pyrimidine (84 mg, 0.254 mmol), 4-fluorophenylboronic acid, pinacol ester (76 mg, 0.342 mmol) and cesium fluoride (116 mg, 0.761 mmol) in DMF (1 mL) and water (0.3 mL). After 5 min, tetrakis(triphenylphosphine)palladium(0) (29 mg, 0.025 mmol) was added and the resulting mixture was heated at 95° C. for 16 hours. The reaction was diluted with water (6 mL) and EtOAc (3 mL). The aqueous phase was extracted EtOAc (2×10 mL). The combined organic phases were passed through a hydrophobic frit, combined and the solvent was removed in vacuo. Purification by reverse phase preparative HPLC afforded 6-(4-fluorophenyl)-4-[(6-methyl-3-pyridyl)methoxy]pyrido[2,3-d]pyrimidine (52 mg, 59%) as a 0.5 eq formate salt.

$^1H$ NMR (400 MHz, DMSO): δ 9.35 (d, J=2.8 Hz, 1H), 8.92 (s, 1H), 8.73 (d, J=2.5 Hz, 1H), 8.61 (d, J=1.5 Hz, 1H), 8.32 (s, 0.5H), 7.97 (dd, J=5.3, 8.6 Hz, 2H), 7.77 (dd, J=2.1, 8.0 Hz, 1H), 7.42 (dd, J=8.8, 8.8 Hz, 2H), 7.29 (d, J=8.1 Hz, 1H), 5.27 (s, 2H), 2.49 (s, 3H).

LCMS (Method 4): [MH+]=347 at 2.82 min.

The following compound reported in the table below was prepared according to the same procedure described for the preparation of 6-(4-fluorophenyl)-4-[(6-methyl-3-pyridyl)methoxy]pyrido[2,3-d]pyrimidine.

| Comparative Example No. | Chemical name Structure | Analytical data $^1H$ NMR LC-MS |
|---|---|---|
| Comparative Example B | 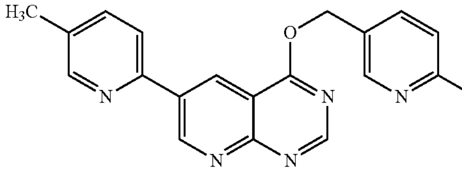 6-(5-methylpyridin-2-yl)-4-((6-methylpyridin-3-yl)methoxy)pyrido[2,3-d]pyrimidine | $^1H$ NMR (400 MHz, DMSO): δ 9.70 (d, J = 2.3 Hz, 1 H), 9.14 (d, J = 2.3 Hz, 1 H), 8.92 (s, 1 H), 8.66-8.60 (m, 2 H), 8.18 (d, J = 8.1 Hz, 1 H), 7.83 (d, J = 6.8 Hz, 1 H), 7.78 (dd, J = 1.9, 8.0 Hz, 1 H), 7.29 (d, J = 8.1 Hz, 1 H), 5.27 (s, 2 H), 2.49 (s, 3 H), 2.42 (s, 3 H). LCMS (Method 3): [MH+] = 344 at 3.31 m |

The activity of the comparative examples A and B have been tested in the in vitro Electrophysiology Assay for $P2X_3$ as described above.

Results for individual compounds are provided below in Table 10 and are expressed as range of activity.

TABLE 10

| Comparative Example No. | h $P2X_3$ |
|---|---|
| A | inactive |
| B | inactive |

Inactive: $pIC_{50}$ h $P2X_3$ < 4.5.

The invention claimed is:

1. A compound of formula (I)

(I)

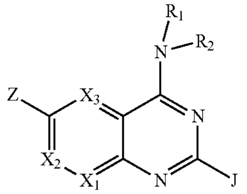

wherein $X_1$, $X_2$ and $X_3$ are independently CH or N, wherein at least one of $X_1$, $X_2$, and $X_3$ is N, and wherein $X_1$ is N when $X_3$ is N, Z is selected from the group consisting of heteroaryl, and aryl, wherein heteroaryl is selected from the group consisting of thienyl, furyl, pyrrolyl, imidazolyl, thiazolyl, isothiazolyl, oxazolyl, isoxazolyl, isothiazolyl, triazolyl, thiadiazolyl, oxadiazolyl, pyridinyl, pyridazinyl, pyrimidinyl, pyrazinyl, tetrazolyl, and triazinyl, and wherein any of such heteroaryl and aryl may be optionally substituted by one or more groups selected from $(C_1$-$C_3)$alkyl, halo, CN, and $(R^AR^B)NC(O)$—;

$R_1$ is H;

$R_2$ is selected from the group consisting of heteroaryl$(C_1$-$C_4)$alkyl-, and $(C_3$-$C_8)$heterocycloalkyl-$(C_1$-$C_6)$alkyl-, wherein any of such alkyl, heteroaryl and heterocycloalkyl may be optionally substituted by one or more groups selected from $(C_1$-$C_3)$alkyl, halo, $R^AO(C_1$-$C_4)$ alkylene-, $(C_1$-$C_6)$ haloalkyl, and $R^AO$—;

$R^A$ and $R^B$ are at each occurrence independently H or $(C_1$-$C_4)$alkyl-, or $R^A$ and $R^B$ may form together with the nitrogen atom to which they are attached a 6-membered saturated heterocyclic monocyclic ring system optionally containing a further heteroatom which is nitrogen, which may be optionally substituted by $R^C(O)C$—;

$R^C$ is $(C_1$-$C_6)$alkyl; and

J is H or $(R^AR^B)N$—.

2. The compound according to claim 1, selected from the group consisting of:

(R)-6-(4-fluorophenyl)-N-(1-(6-methylpyridazin-3-yl)ethyl)pyrido[2,3-d]pyrimidin-4-amine, N-((6-Methylpyridazin-3-yl)methyl)-6-(5-methylpyridin-2-yl)pyrido[2,3-d]pyrimidin-4-amine, (R)-6-(5-Methylpyridin-2-yl)-N-(1-(2-(trifluoromethyl)pyrimidin-5-yl)ethyl)pyrido[2,3-d]pyrimidin-4-amine, (R)-6-(5-Chloropyridin-2-yl)-N-(1-(2-(trifluoromethyl)pyrimidin-5-yl)ethyl)pyrido[2,3-d]pyrimidin-4-amine, (R)-6-(4-Fluorophenyl)-N-(1-(2-(trifluoromethyl)pyrimidin-5-yl)ethyl)pyrido[2,3-d]pyrimidin-4-amine, N-((6-methylpyridin-3-yl)methyl)-6-(p-tolyl)pyrido[2,3-d]pyrimidin-4-amine, N-((6-methylpyridin-3-yl)methyl)-6-(5-methylthiophen-2-yl)pyrido[2,3-d]pyrimidin-4-amine, N-((3,5-difluoropyridin-2-yl)methyl)-6-(4-fluorophenyl)pyrido[2,3-d]pyrimidin-4-amine, 6-(4-Fluorophenyl)-N-[(1R)-1-[2-(trifluoromethyl)pyrimidin-5-yl]ethyl]pyrido[3,4-d]pyrimidin-4-amine, 6-(4-Fluorophenyl)-N-((6-methylpyridin-3-yl)methyl)pteridin-4-amine, 6-(4-fluorophenyl)-N-[1-(3-methyl-1,2,4-oxadiazol-5-yl)ethyl]pyrido[2,3-d]pyrimidin-4-amine, Single enantiomer 1 of 6-(4-fluorophenyl)-N-[1-(3-methyl-1,2,4-oxadiazol-5-yl)ethyl]pyrido[2,3-d]pyrimidin-4-amine, Single enantiomer 2 of 6-(4-fluorophenyl)-N-[1-(3-methyl-1,2,4-oxadiazol-5-yl)ethyl]pyrido[2,3-d]pyrimidin-4-amine, 6-(5-methylthiazol-2-yl)-N-[[3-(trifluoromethyl)-1,2,4-oxadiazol-5-yl]methyl]pyrido[2,3-d]pyrimidin-4-amine, 6-(5-methylthiazol-2-yl)-N-[[2-(trifluoromethyl)pyrimidin-5-yl]methyl]pyrido[2,3-d]pyrimidin-4-amine,N-[(3-methyl-1,2,4-oxadiazol-5-yl)methyl]-6-(5-methylthiazol-2-yl)pyrido[2,3-d]pyrimidin-4-amine, N-[(6-methylpyridazin-3-yl)methyl]-6-(5-methylthiazol-2-yl)pyrido[2,3-d]pyrimidin-4-amine, 6-(4-fluorophenyl)-N-(2-(3-methyl-1,2,4-oxadiazol-5-yl)ethyl)pyrido[2,3-d]pyrimidin-4-amine, 6-(5-methylpyridin-2-yl)-N-((3-(trifluoromethyl)-1,2,4-oxadiazol-5-yl)methyl)pyrido[2,3-d]pyrimidin-4-amine, (6-(5-Fluoro-2-pyridyl)-N-[(1R)-1-(3-methyl-1,2,4-oxadiazol-5-yl)ethyl]pyrido[2,3-d]pyrimidin-4-amine, (R)-6-(5-fluoropyridin-2-yl)-N-(1-(2-(trifluoromethyl)pyrimidin-5-yl)ethyl)pyrido[2,3-d]pyrimidin-4-amine, N-[(1R)-1-(3-methyl-1,2,4-oxadiazol-5-yl)ethyl]-6-(5-methylpyrimidin-2-yl)pyrido[2,3-d]pyrimidin-4-amine, 6-(4-fluorophenyl)-N-[(1R)-1-[6-(trifluoromethyl)pyridazin-3-yl]ethyl]pyrido[2,3-d]pyrimidin-4-amine, 6-(5-fluoropyridin-2-yl)-N-((3-(trifluoromethyl)-1,2,4-oxadiazol-5-yl)methyl)pyrido[2,3-d]pyrimidin-4-amine, N-[(5-methyl-1,2,4-oxadiazol-3-yl)methyl]-6-(5-methylthiazol-2-yl)pyrido[2,3-d]pyrimidin-4-amine, N-[(5-methyl-1,3,4-oxadiazol-2-yl)methyl]-6-(5-methylthiazol-2-yl)pyrido[2,3-d]pyrimidin-4-amine, 6-(4-fluorophenyl)-N-[(5-methyl-1,3,4-oxadiazol-2-yl)methyl]pyrido[2,3-d]pyrimidin-4-amine, 6-(5-methylthiazol-2-yl)-N-[(2-methylthiazol-4-yl)methyl]pyrido[2,3-d]pyrimidin-4-amine, 6-(4-fluorophenyl)-N-[1-[3-(trifluoromethyl)-1,2,4-oxadiazol-5-yl]ethyl]pyrido[2,3-d]pyrimidin-4-amine, 6-(4-fluorophenyl)-N-[(3-methylisoxazol-5-yl)methyl]pyrido[2,3-d]pyrimidin-4-amine, N-[(5-methyl-1,3,4-thiadiazol-2-yl)methyl]-6-(5-methylthiazol-2-yl)pyrido[2,3-d]pyrimidin-4-amine, 6-(4-fluorophenyl)-N-[(2-methylthiazol-4-yl)methyl]pyrido[2,3-d]pyrimidin-4-amine, 6-(4-fluorophenyl)-N-[(5-methyl-1,2,4-oxadiazol-3-yl)methyl]pyrido[2,3-d]pyrimidin-4-amine, N-[(3-methylisoxazol-5-yl)methyl]-6-(5-methylthiazol-2-yl)pyrido[2,3-d]pyrimidin-4-amine, Single enantiomer 1 of 6-(5-fluoro-2-pyridyl)-N-[1-(5-methyl-1,3,4-thiadiazol-2-yl)ethyl]pyrido[2,3-d]pyrimidin-4-amine, Single enantiomer 2 of 6-(5-fluoro-2-pyridyl)-N-[1-(5-methyl-1,3,4-thiadiazol-2-yl)ethyl]pyrido[2,3-d]pyrimidin-4-amine, Single enantiomer 1 of N-(1-(5-methyl-1,3,4-thiadiazol-2-yl)ethyl)-6-(5-methylpyridin-2-yl)pyrido[2,3-d]pyrimidin-4-amine, Single enantiomer 2 of N-(1-(5-methyl-1,3,4-thiadiazol-2-yl)ethyl)-6-(5-methylpyridin-2-yl)pyrido[2,3-d]pyrimidin-4-amine, 6-(4-Fluorophenyl)-N-[(5-methyl-1,3,4-thiadiazol-2-yl)methyl]pyrido[2,3-d]pyrimidin-4-amine, 6-(4-fluorophenyl)-N-[(3-methyl-1,2,4-oxadiazol-5-yl)methyl]pyrido[2,3-d]pyrimidin-4-amine, 6-(4-fluorophenyl)-N-[[3-(trifluoromethyl)-1,2,4-oxadiazol-5-yl]methyl]pyrido[2,3-d]pyrimidin-4-amine, 6-(5-chloro-2-pyridyl)-N-[(1S)-1-[2-(trifluoromethyl)pyrimidin-5-yl]ethyl]pyrido[2,3-d]pyrimidin-4-amine, 6-phenyl-N-[(1R)-1-[2-(trifluoromethyl)pyrimidin-5-yl]ethyl]pyrido[2,3-d]pyrimidin-4-amine, Single enantiomer 1 of 6-(4-fluorophenyl)-N-[1-[3-(trifluoromethyl)-1,2,4-oxadiazol-5-yl]ethyl]pyrido[2,3-d]pyrimidin-4-amine, Single enantiomer 1 of 6-(4-fluorophenyl)-N-(1-(5-methyl-1,3,4-thiadiazol-2-yl)ethyl)pyrido[2,3-d]pyrimidin-4-amine, Single enantiomer 2 of 6-(4-fluorophenyl)-N-(1-(5-methyl-1,3,4-thiadiazol-2-yl)ethyl)pyrido[2,3-d]pyrimidin-4-amine, Single enantiomer 1 of N-[1-(3,5-difluoro-2-pyridyl)ethyl]-6-(4-fluorophenyl)pyrido[2,3-d]pyrimidin-4-amine, Single enantiomer 2 of N-[1-(3,5-difluoro-2-pyridyl)ethyl]-6-(4-fluorophenyl)pyrido[2,3-d]pyrimidin-4-amine, N-[1-(3,5-difluoro-2-pyridyl)ethyl]-6-(4-fluorophenyl)pyrido[2,3-d]pyrimidin-4-amine, and 6-(5-methylthiazol-2-yl)-N-[(1R)-1-[2-(trifluoromethyl)pyrimidin-5-yl]ethyl]pyrido[2,3-d]pyrimidin-4-amine.

3. The compound of formula (I) according to claim 1, wherein $X_1$ is N, $X_2$ and $X_3$ are CH, represented by the formula (Ia)

(Ia)

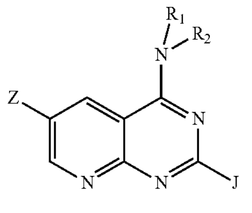

wherein

Z is selected from the group consisting of heteroaryl, and aryl, wherein any of such heteroaryl and aryl may be optionally substituted by one or more groups selected from $(C_1\text{-}C_3)$alkyl, halo, CN, and $(R^AR^B)$NC(O)—;

$R_1$ is H;

$R_2$ is selected from the group consisting of heteroaryl $(C_1\text{-}C_4)$alkyl-, and $(C_3\text{-}C_8)$heterocycloalkyl-$(C_1\text{-}C_6)$ alkyl, wherein any of such alkyl, and heteroaryl may be optionally substituted by one or more groups selected from $(C_1\text{-}C_3)$alkyl, halo, $R^AO(C_1\text{-}C_4)$alkylene-, $(C_1\text{-}C_6)$ haloalkyl, and $R^AO$—;

$R^A$ and $R^B$ are at each occurrence independently H or $(C_1\text{-}C_4)$alkyl-, or $R^A$ and $R^B$ may form together with the nitrogen atom to which they are attached a 6 membered saturated heterocyclic monocyclic ring system optionally containing a further heteroatom which is nitrogen, which may be optionally substituted by $R^C$(O)C—;

$R^C$ is $(C_1\text{-}C_6)$alkyl; and

J is H or $(R^AR^B)$N—.

4. The compound according to claim 3, selected from the group consisting of:

6-(4-fluorophenyl)-N-[1-(3-methyl-1,2,4-oxadiazol-5-yl)ethyl]pyrido[2,3-d]pyrimidin-4-amine, Single enantiomer 1 of 6-(4-fluorophenyl)-N-[1-(3-methyl-1,2,4-oxadiazol-5-yl)ethyl]pyrido[2,3-d]pyrimidin-4-amine, Single enantiomer 2 of 6-(4-Fluorophenyl)-N-[1-(3-methyl-1,2,4-oxadiazol-5-yl)ethyl]pyrido[2,3-d]pyrimidin-4-amine;

(R)-5-(1-((6-(4-fluorophenyl)pyrido[2,3-d]pyrimidin-4-yl)amino)ethyl)-2-(trifluoromethyl)pyridine 1-oxide;

(R)-6-(4-fluorophenyl)-N-(1-(6-methylpyridazin-3-yl)ethyl)pyrido[2,3-d]pyrimidin-4-amine;

(S)-2-((6-(4-fluorophenyl)pyrido[2,3-d]pyrimidin-4-yl)amino)-2-(6-methoxypyridin-3-yl)ethan-1-ol;

6-(4-fluorophenyl)-N-(2-morpholinoethyl)pyrido[2,3-d]pyrimidin-4-amine formate;

N-(1-(3-Methyl-1,2,4-oxadiazol-5-yl)ethyl)-6-(5-methylthiazol-2-yl)pyrido[2,3-d]-pyrimidin-4-amine;

N-((6-Methylpyridazin-3-yl)methyl)-6-(5-methylpyridin-2-yl)pyrido[2,3-d]pyrimidin-4-amine;

6-(5-Chloropyridin-2-yl)-N-((6-methylpyridazin-3-yl)methyl)pyrido[2,3-d]pyrimidin-4-amine;

(R)-6-(5-Methylpyridin-2-yl)-N-(1-(2-(trifluoromethyl)pyrimidin-5-yl)ethyl)pyrido[2,3-d]pyrimidin-4-amine;

6-(5-methylpyridin-2-yl)-N-((6-methylpyridin-3-yl)methyl)pyrido[2,3-d]pyrimidin-4-amine;

(R)-6-(5-Chloropyridin-2-yl)-N-(1-(2-(trifluoromethyl)pyrimidin-5-yl)ethyl)pyrido[2,3-d]pyrimidin-4-amine;

6-(5-Chloropyridin-2-yl)-N-(1-(3-methyl-1,2,4-oxadiazol-5-yl)ethyl)pyrido[2,3-d]pyrimidin-4-amine;

(R)-6-(4-Fluorophenyl)-N-(1-(2-(trifluoromethyl)pyrimidin-5-yl)ethyl)pyrido[2,3-d]pyrimidin-4-amine;

N-((6-methylpyridin-3-yl)methyl)-6-(p-tolyl)pyrido[2,3-d]pyrimidin-4-amine;

N-((6-methylpyridin-3-yl)methyl)-6-(5-methylthiophen-2-yl)pyrido[2,3-d]pyrimidin-4-amine;

6-(4-fluorophenyl)-N-((6-methylpyridin-3-yl)methyl)pyrido[2,3-d]pyrimidin-4-amine;

2-(4-(((6-methylpyridin-3-yl)methyl)amino)pyrido[2,3-d]pyrimidin-6-yl)benzonitrile;

2-(4-(((6-methylpyridin-3-yl)methyl)amino)pyrido[2,3-d]pyrimidin-6-yl)benzamide;

N-((3,5-difluoropyridin-2-yl)methyl)-6-(4-fluorophenyl)pyrido[2,3-d]pyrimidin-4-amine;

6-(4-fluorophenyl)-N-((6-methylpyridazin-3-yl)methyl)pyrido[2,3-d]pyrimidin-4-amine;

1-(4-(6-(4-fluorophenyl)-4-(((6-methylpyridazin-3-yl)methyl)amino)pyrido[2,3-d]pyrimidin-2-yl)piperazin-1-yl)ethan-1-one;

1-(4-(4-(((6-Methylpyridazin-3-yl)methyl)amino)-6-(5-methylthiazol-2-yl)pyrido[2,3-d]pyrimidin-2-yl)piperazin-1-yl)ethan-1-one;

1-(4-(4-(((6-Methylpyridazin-3-yl)methyl)amino)-6-(5-methylpyridin-2-yl)pyrido[2,3-d]pyrimidin-2-yl)piperazin-1-yl)ethan-1-one;

6-(5-methylthiazol-2-yl)-N-[[3-(trifluoromethyl)-1,2,4-oxadiazol-5-yl]methyl]pyrido[2,3-d]pyrimidin-4-amine, 6-(5-methylthiazol-2-yl)-N-[[2-(trifluoromethyl)pyrimidin-5-yl]methyl]pyrido[2,3-d]pyrimidin-4-amine, N-[(3-methyl-1,2,4-oxadiazol-5-yl)methyl]-6-(5-methylthiazol-2-yl)pyrido[2,3-d]pyrimidin-4-amine, N-[(6-methylpyridazin-3-yl)methyl]-6-(5-methylthiazol-2-yl)pyrido[2,3-d]pyrimidin-4-amine, 2-((6-(4-fluorophenyl)pyrido[2,3-d]pyrimidin-4-yl)amino)-2-(5-methyl-1,2,4-oxadiazol-3-yl)ethan-1-ol, (R)-6-(4-fluorophenyl)-N-(1-(5-methyl-1,3,4-oxadiazol-2-yl)ethyl)pyrido[2,3-d]pyrimidin-4-amine, 6-(4-fluorophenyl)-N-(1-(5-methyl-1,3,4-thiadiazol-2-yl)ethyl)pyrido[2,3-d]pyrimidin-4-amine, (R)-6-(4-fluorophenyl)-N-(1-(5-methyl-1,2,4-oxadiazol-3-yl)ethyl)pyrido[2,3-d]pyrimidin-4-amine, 6-(4-fluorophenyl)-N-(2-(3-methyl-1,2,4-oxadiazol-5-yl)propan-2-yl)pyrido[2,3-d]pyrimidin-4-amine, N-(1-(3,5-difluoropyridin-2-yl)ethyl)-6-(4-fluorophenyl)pyrido[2,3-d]pyrimidin-4-amine, 6-(4-fluorophenyl)-N-(2-(3-methyl-1,2,4-oxadiazol-5-yl)ethyl)pyrido[2,3-d]pyrimidin-4-amine, 6-(5-methylpyridin-2-yl)-N-((3-(trifluoromethyl)-1,2,4-oxadiazol-5-yl)methyl)pyrido[2,3-d]pyrimidin-4-amine, (6-(5-Fluoro-2-pyridyl)-N-[(1R)-1-(3-methyl-1,2,4-oxadiazol-5-yl)ethyl]pyrido[2,3-d]pyrimidin-4-amine, (R)-6-(5-fluoropyridin-2-yl)-N-(1-(2-(trifluoromethyl)pyrimidin-5-yl)ethyl)pyrido[2,3-d]pyrimidin-4-amine, N-[(1R)-1-(3-methyl-1,2,4-oxadiazol-5-yl)ethyl]-6-(5-methylpyrimidin-2-yl)pyrido[2,3-d]pyrimidin-4-amine, 6-(4-fluorophenyl)-N-[(1R)-1-[6-(trifluoromethyl)pyridazin-3-yl]ethyl]pyrido[2,3-d]pyrimidin-4-amine, 6-(5-fluoropyridin-2-yl)-N-((3-(trifluoromethyl)-1,2,4-oxadiazol-5-yl)methyl)pyrido[2,3-d]pyrimidin-4-amine, N-[(5-methyl-1,2,4-oxadiazol-3-yl)methyl]-6-(5-methylthiazol-2-yl)pyrido[2,3-d]pyrimidin-4-amine, N-[(5-methyl-1,3,4-oxadiazol-2-yl)methyl]-6-(5-methylthiazol-2-yl)pyrido[2,3-d]pyrimidin-4-amine, 6-(4-fluorophenyl)-N-[(5-methyl-1,3,4-oxadiazol-2-yl)methyl]pyrido[2,3-d]pyrimidin-4-amine, 6-(5-methylthiazol-2-yl)-N-[(2-methylthiazol-4-yl)methyl]pyrido[2,3-d]pyrimidin-4-amine, 6-(4-fluorophenyl)-N-[1-[3-(trifluoromethyl)-1,2,4-oxadiazol-5-yl]ethyl]pyrido[2,3-d]pyrimidin-4-amine, 6-(4-fluorophenyl)-N-[(3-methylisoxazol-5-yl)methyl]pyrido[2,3-d]pyrimidin-4-amine, N-[(5-methyl-1,3,4-thiadiazol-2-yl)methyl]-6-(5-methylthiazol-2-yl)pyrido[2,3-d]pyrimidin-4-amine, 6-(4-fluorophenyl)-N-[(2-methylthiazol-4-yl)methyl]pyrido[2,3-d]pyrimidin-4-amine, 6-(4-fluorophenyl)-N-[(5-methyl-1,2,4-oxadiazol-3-yl)methyl]pyrido[2,3-d]pyrimidin-4-amine, N-[(3-methylisoxazol-5-yl)methyl]-6-(5-methylthiazol-2-yl)pyrido[2,3-d]pyrimidin-4-amine, Single enantiomer 1 of 6-(5-fluoro-2-pyridyl)-N-[1-(5-methyl-1,3,4-thiadiazol-2-yl)ethyl]pyrido[2,3-d]pyrimidin-4-amine, Single enantiomer 2 of 6-(5-fluoro-2-pyridyl)-N-[1-(5-methyl-1,3,4-thiadiazol-2-yl)ethyl]pyrido[2,3-d]pyrimidin-4-amine, Single enantiomer 1 of N-(1-(5-methyl-1,3,4-thiadiazol-2-yl)ethyl)-6-(5-methylpyridin-2-yl)pyrido[2,3-d]pyrimidin-4-amine, Single enantiomer 2 of N-(1-(5-methyl-1,3,4-thiadiazol-2-yl)ethyl)-6-(5-methylpyridin-2-yl)pyrido[2,3-d]pyrimidin-4-amine, 6-(4-Fluorophenyl)-N-[(5-methyl-1,3,4-thiadiazol-2-yl)methyl]pyrido[2,3-d]pyrimidin-4-amine, 6-(4-fluorophenyl)-N-[(3-methyl-1,2,4-oxadiazol-5-yl)methyl]pyrido[2,3-d]pyrimidin-4-amine, 6-(4-fluorophenyl)-N-[[3-(trifluoromethyl)-1,2,4-oxadiazol-5-yl]methyl]pyrido[2,3-d]pyrimidin-4-amine, 6-(5-chloro-2-pyridyl)-N-[(1S)-1-[2-(trifluoromethyl)pyrimidin-5-yl]ethyl]pyrido[2,3-d]pyrimidin-4-amine, 6-phenyl-N-[(1R)-1-[2-(trifluoromethyl)pyrimidin-5-yl]ethyl]pyrido[2,3-d]pyrimidin-4-amine, Single enantiomer 1 of 6-(4-fluorophenyl)-N-[1-[3-(trifluoromethyl)-1,2,4-oxadiazol-5-yl]ethyl]pyrido[2,3-d]pyrimidin-4-amine, Single enantiomer 1 of 6-(4-fluorophenyl)-N-(1-(5-methyl-1,3,4-thiadiazol-2-yl)ethyl)pyrido[2,3-d]pyrimidin-4-amine, Single enantiomer 2 of 6-(4-fluorophenyl)-N-(1-(5-methyl-1,3,4-thiadiazol-2-yl)ethyl)pyrido[2,3-d]pyrimidin-4-amine, Single enantiomer 1 of N-[1-(3,5-difluoro-2-pyridyl)ethyl]-6-(4-fluorophenyl)pyrido[2,3-d]pyrimidin-4-amine, Single enantiomer 2 of N-[1-(3,5-difluoro-2-pyridyl)ethyl]-6-(4-fluorophenyl)pyrido[2,3-d]pyrimidin-4-amine, N-[1-(3,5-difluoro-2-pyridyl)ethyl]-6-(4-fluorophenyl)pyrido[2,3-d]pyrimidin-4-amine, and 6-(5-methylthiazol-2-yl)-N-[(1R)-1-[2-(trifluoromethyl)pyrimidin-5-yl]ethyl]pyrido[2,3-d]pyrimidin-4-amine.

5. The compound of formula (I) according to claim 1, wherein $X_1$ is CH, represented by the formula Ib (Ib)

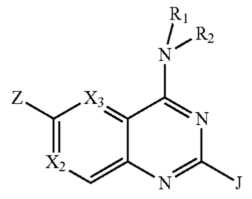

wherein

Z is selected from the group consisting of heteroaryl and aryl wherein any of such aryl and heteroaryl may be optionally substituted by one or more groups selected from $(C_1\text{-}C_3)$alkyl, and halo;

$R_1$ is H;

$R_2$ is heteroaryl$(C_1\text{-}C_4)$alkyl-, wherein any of such alkyl and heteroaryl may be optionally substituted by one or more groups selected from $(C_1\text{-}C_3)$alkyl, and $(C_1\text{-}C_6)$ haloalkyl; and J is H.

6. The compound according to claim 5, selected from the group consisting of:

6-(4-Fluorophenyl)-N-((6-methylpyridazin-3-yl)methyl)pyrido[3,4-d]pyrimidin-4-amine;

6-(4-Fluorophenyl)-N-[(1R)-1-[2-(trifluoromethyl)pyrimidin-5-yl]ethyl]pyrido[3,4-d]pyrimidin-4-amine;

N-[(6-Methylpyridazin-3-yl)methyl]-6-(5-methylthiazol-2-yl)pyrido[3,4-d]pyrimidin-4-amine;

N-[(6-methylpyridazin-3-yl)methyl]-6-(5-methyl-2-pyridyl)pyrido[3,4-d]pyrimidin-4-amine; and 6-(5-methylthiazol-2-yl)-N-[(1R)-1-[2-(trifluoromethyl) pyrimidin-5-yl]ethyl]pyrido[3,4-d]pyrimidin-4-amine.

7. The compound of formula (I) according to claim 1, wherein $X_1$ and $X_3$ are N and $X_2$ is CH, represented by the formula Ic (Ic)

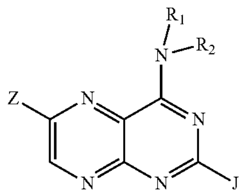

wherein

Z is selected from the group consisting of aryl and heteroaryl wherein any of such aryl and heteroaryl may be optionally substituted by one or more groups selected from halo and $(C_1-C_3)$alkyl;

$R_1$ is H;

$R_2$ is heteroaryl$(C_1-C_4)$alkyl-, wherein the heteroaryl may be optionally substituted by one or more groups selected from $(C_1-C_3)$alkyl, and $(C_1-C_6)$ haloalkyl; and J is H.

8. The compound according to claim 7, selected from the group consisting of:

6-(4-Fluorophenyl)-N-((6-methylpyridazin-3-yl)methyl) pteridin-4-amine 6-(4-Fluorophenyl)-N-(1-(3-methyl-1,2,4-oxadiazol-5-yl)ethyl)pteridin-4-amine (R)-6-(4-fluorophenyl)-N-(1-(2-(trifluoromethyl)pyrimidin-5-yl)ethyl)pteridin-4-amine, and 6-(4-Fluorophenyl)-N-((6-methylpyridin-3-yl)methyl) pteridin-4-amine.

9. A pharmaceutical composition comprising a compound as defined in claim 1, or a pharmaceutically acceptable salt thereof, either alone or in combination with another one or more active ingredient, in admixture with one or more pharmaceutically acceptable carrier or excipient.

10. The pharmaceutical composition according to claim 9 for oral administration.

11. A method for treatment of disorders associated with $P2X_3$ receptors mechanisms, comprising administering to a patient in need of such treatment a therapeutically effective amount of compound according to claim 1.

12. A method for the treatment of respiratory diseases selected from cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD), cough associated with respiratory diseases and bronchospasm, comprising administering to a patient in need of such treatment a therapeutically effective amount of a compound according to claim 1.

13. A method according to claim 12, wherein the respiratory disease is chronic cough.

14. A compound selected from the group consisting of:

6-(4-Fluorophenyl)-N-((6-methylpyridazin-3-yl)methyl) pyrido[3,2-d]pyrimidin-4-amine;

N-((6-methylpyridazin-3-yl)methyl)-6-(5-methylpyridin-2-yl)pyrido[3,2-d]-pyrimidin-4-amine;

N-(1-(3-methyl-1,2,4-oxadiazol-5-yl)ethyl)-6-(5-methylpyridin-2-yl)pyrido[3,2-d]pyrimidin-4-amine;

N-[(6-methylpyridazin-3-yl)methyl]-6-(5-methylthiazol-2-yl)pyrido[3,2-d]pyrimidin-4-amine;

(R)-6-(5-Methylpyridin-2-yl)-N-(1-(2-(trifluoromethyl) pyrimidin-5-yl)ethyl)pyrido[3,2-d]pyrimidin-4-amine;

(R)-6-(5-methylthiazol-2-yl)-N-(1-(2-(trifluoromethyl) pyrimidin-5-yl)ethyl)-pyrido[3,2-d]pyrimidin-4-amine;

(R)-6-(4-fluorophenyl)-N-(1-(2-(trifluoromethyl)pyrimidin-5-yl)ethyl)pyrido[3,2-d]pyrimidin-4-amine; and 6-(4-Fluorophenyl)-N-(1-(3-methyl-1,2,4-oxadiazol-5-yl)ethyl)pyrido[3,2-d]pyrimidin-4-amine.

* * * * *